(12) United States Patent
Vukicevic et al.

(10) Patent No.: US 11,596,712 B2
(45) Date of Patent: *Mar. 7, 2023

(54) AUTOLOGOUS BONE GRAFT SUBSTITUTE COMPOSITION

(71) Applicant: Perform Biologies, Inc., Holliston, MA (US)

(72) Inventors: Slobodan Vukicevic, Zagreb (HR); Kuber T. Sampath, Holliston, MA (US); Lovorka Grgurevic, Zagreb (HR); Charles Cohen, Weston, MA (US); Hermann Oppermann, Medway, MA (US)

(73) Assignee: Genera Istrazivanja d.o.o.

( * ) Notice: Subject to any disclaimer, the term of this patent is extended or adjusted under 35 U.S.C. 154(b) by 0 days.

This patent is subject to a terminal disclaimer.

(21) Appl. No.: 17/215,843

(22) Filed: Mar. 29, 2021

(65) Prior Publication Data

US 2021/0213165 A1    Jul. 15, 2021

Related U.S. Application Data

(63) Continuation-in-part of application No. 16/756,783, filed as application No. PCT/EP2018/025270 on Oct. 19, 2018, now Pat. No. 10,960,109.

(Continued)

(51) Int. Cl.
*A61L 27/36* (2006.01)
*A61L 27/26* (2006.01)
(Continued)

(52) U.S. Cl.
CPC .......... *A61L 27/365* (2013.01); *A61L 27/025* (2013.01); *A61L 27/12* (2013.01); *A61L 27/26* (2013.01);
(Continued)

(58) Field of Classification Search
CPC .......... A61L 27/54; A61L 27/46; A61L 27/26; A61L 27/025; A61L 27/3608;
(Continued)

(56) References Cited

U.S. PATENT DOCUMENTS

| 3,740,421 A | 6/1973 | Schmolka et al. |
| 4,968,590 A | 11/1990 | Kuberasampath et al. |

(Continued)

FOREIGN PATENT DOCUMENTS

| WO | 9119510 A1 | 12/1991 |
| WO | 2008011192 A2 | 1/2008 |
| WO | 2009129631 A1 | 10/2009 |

OTHER PUBLICATIONS

Carragee, E. J., Hurwitz, E. L., Weiner, B. K. (2011) A critical review of recombinant human bone morphogenetic protein-2 trials in spinal surgery: emerging safety concerns and lessons learned. Spine J 11:471-491.

(Continued)

*Primary Examiner* — Blessing M Fubara
(74) *Attorney, Agent, or Firm* — St Onge Steward Johnston and Reens LLC

(57) ABSTRACT

An autologous bone graft substitute composition for inducing new bone formation, promoting bone growth and treating bone defects, a method of preparation thereof, and a method of inducing or promoting bone growth by treatment of a bone with an autologous bone graft substitute composition. The composition includes autologous blood; one or more analogs of an osteogenic bone morphogenetic protein selected from BMP-6, BMP-2, BMP-7, BMP-4, BMP-5, BMP-8, BMP-9, BMP-12, and BMP-13, and combinations thereof; and a compression resistant matrix selected from the group consisting of a bone autograft, bone allograft, hydroxyapatite, tri-calcium phosphate, and combinations thereof. The autologous blood forms a coagulum gel com- (Continued)

prising a fibrin-meshwork reinforced with the compression resistant matrix and containing the osteogenic bone morphogenetic protein which is released over a sustained period.

28 Claims, 29 Drawing Sheets

Related U.S. Application Data

(60) Provisional application No. 62/574,656, filed on Oct. 19, 2017.

(51) Int. Cl.
*A61L 27/12* (2006.01)
*A61L 27/54* (2006.01)
*A61L 27/02* (2006.01)
*A61L 27/46* (2006.01)
*A61L 27/44* (2006.01)

(52) U.S. Cl.
CPC ....... *A61L 27/3608* (2013.01); *A61L 27/3616* (2013.01); *A61L 27/3691* (2013.01); *A61L 27/44* (2013.01); *A61L 27/46* (2013.01); *A61L 27/54* (2013.01); *A61L 2300/102* (2013.01); *A61L 2300/252* (2013.01); *A61L 2300/414* (2013.01); *A61L 2300/418* (2013.01); *A61L 2400/06* (2013.01); *A61L 2400/12* (2013.01); *A61L 2430/02* (2013.01); *A61L 2430/12* (2013.01); *A61L 2430/38* (2013.01)

(58) Field of Classification Search
CPC ...... A61L 27/3691; A61L 27/12; A61L 27/44; A61L 27/365; A61L 27/3616; A61L 2400/06; A61L 2300/414; A61L 2300/418; A61L 2400/12; A61L 2430/12; A61L 2300/252; A61L 2300/102; A61L 2430/38

See application file for complete search history.

(56) References Cited

U.S. PATENT DOCUMENTS

| | | | |
|---|---|---|---|
| 5,011,691 | A | 4/1991 | Oppermann et al. |
| 5,674,844 | A | 10/1997 | Kuberasampath et al. |
| 6,190,880 | B1 | 2/2001 | Israel et al. |
| 6,333,312 | B1 | 12/2001 | Kuberasampath et al. |
| 6,593,109 | B1 | 7/2003 | Israel et al. |
| 7,678,885 | B2 | 3/2010 | Israel et al. |
| 7,786,080 | B2 | 8/2010 | Muller et al. |
| 8,197,840 | B2 * | 6/2012 | Vukicevic .......... A61K 38/1875 424/426 |
| 8,828,937 | B2 | 9/2014 | Seemann et al. |
| 10,960,109 | B2 * | 3/2021 | Vukicevic ............. A61L 27/365 |

OTHER PUBLICATIONS

Gupta S, M. V., Gupta MC (2017) Biology of spine fusion and application of osteobiologies in spine surgery. In: Vukicevic S, Sampath, et al (ed) Bone Morphogenetic Proteins: Systems Biology Regulators. Springer International Publishing pp. 229-247 "Progress in Inflammation Research".

Vukicevic S, Sampath TK, editors. Bone Morphogenetic Proteins: from Laboratory to Clinical Practice. Basel: Birkhauser Verlag, 2002.

Vukicevic S, Sampath, et al., editors, Bone Morphogenetic Proteins: Systems Biology Regulators. Springer International Publishing; 2017.

Sampath, T.K., Coughlin, J.E., Whetstone, R.M., Banach, D., Corbett, C., Ridge, R.J., Ozkaynak, E., Oppermann, H. and Rueger, D.C. 1990. Bovine osteogenic protein is composed of dimers of OP-1 and BMP-2A, two members of the Transforming Growth Factor—β superfamily. J. Biol. Chem. 265: 13198-13205.

Griffith, D.L., Oppermann, H., Rueger, D.C., Sampath, et al., Tucker, R.F. and Carlson, W.D. (1994). Crystallization and preliminary crystallographic data of recombinant human Osteogenic Protein-1 (hOP-1). J. Mol. Biol. 244: 657 658.

Sampath TK, Reddi AH. Dissociative extraction and reconstitution of extracellular matrix components involved in local bone differentiation. Proc Natl Acad Sci U S A. 1981;78(12):7599-7603.

Sampath TK, Rashka KE, Doctor JS, Tucker RF, Hoffmann FM (1993) Drosophila transforming growth factor superfamily proteins induce endochondral bone formation in mammals. Proc Natl Acad Sci USA 90:6004 6008.

Executive Summary for P050036 Medtronic's AMPLIFY™ rhBMP-2 and analogs Matrix Orthopedic and Rehabilitation Devices Advisory Panel (2010) Food and Drug Administration.

Asahina, I., Sampath, T.K., Nishimura, I. and Hauschka, P.V. (1993). Human Osteogenic Protein-1 induces both chondroblastic and osteoblastic differentiation of osteoprogenitor cells derived from newborn rat calvaria. J. Cell. Biol. 123:921-933.

Asahina et al., Human Osteogenic Protien-1 Induces Chroblastic, Osteoblastic, and/or Adipocytic Differentiation of Clonal Murine Target Cells, Exp. Cell. Res., 222: 38-47 (1996).

Song K, Krause C, Shi S, Patterson M, Suto R, Grgurevic L, et al. (2010) Identification of a key residue mediating bone morphogenetic protein (BMP)-6 resistance to noggin inhibition allows for engineered BMPs with superior agonist activity. J Biol Chem. 285(16):12169-80.

Medtronic Sofamor Danek USA, Inc. INFUSE Bone Graft product information: Oral/Facial. Memphis, TN; 2006. Available online at www.accessdata.fda.gov/cdrh_docs/pdf5/P050 053c.pdf. Last accessed Feb. 2010.

Sampath, T.K., Muthukumaran, N. and Reddi, A.H. 1987. Isolation of osteogenin, an extracellular matrix-associated, bone-inductive protein, by heparin affinity chromatography. Proc. Natl. Acad. Sci. USA 84: 7109-7113.

Mobbs, R. J. et al. Lumbar interbody fusion: techniques, indications and comparison of interbody fusion options including PLIF, TLIF, MI-TLIF, OLIF/ATP, LLIF and ALIF. J Spine Surg 1:2-18 (2015).

Massagué J (1998) TGF-β Signal Transduction. Annu Rev Biochem 67: 753-791.

Wozney JM, Rosen V, Celeste AJ, Mitsock LM, Whitters MJ, Kriz RW, et al. (1988) Novel regulators of bone formation: molecular clones and activities. Science. 242(4885):1528-34.

Vukicevic, S., Basic, V., Rogic, D., Basic, N., Shih, M-S., Shepard, A., Jin, D., Dattatreyamurty, B., Jones, W., Dorai, H., Ryan, S., Griffiths, D., Maliakal, J., Jelic, M., Pastorcic, M., Stavljenic, A. and Sampath, T.K. (1998). Osteogenic Protein-1 reduces severity of injury in ischemic acute renal failure in rat. J. Clin. Invest. 102: 202-214.

Cahill, K. S., Chi, J. H., Day, A., Claus, E. B. (2009) Prevalence, complications, and hospital charges associated with use of bone-morphogenetic proteins in spinal fusion procedures. JAMA 302:58-66.

Kim DH, Rhim R, Li L, Martha J, Swaim BH, Banco RJ, et al. Prospective study of iliac crest bone graft harvest site pain and morbidity. Spine J. 9:886-92, (2009).

Wang EA, Rosen V, D'Alessandro JS, Bauduy M, Cordes P, Harada T, et al. (1990) Recombinant human bone morphogenetic protein induces bone formation. Proc Natl Acad Sci U S A. 87(6):2220-4.

Sampath TK, Maliakal JC, Hauschka PV, Jones WK, Sasak H, Tucker RF, et al. (1992) Recombinant human osteogenic protein-1 (hOP-1) induces new bone formation in vivo with a specific activity comparable with natural bovine osteogenic protein and stimulates osteoblast proliferation and differentiation in vitro. J Biol Chem. 267 (28):20352-62.

Sampath TK, Rueger DC (1994) Structure, function and orthopedic application of osteogenic protein-1 (OP-1) Complications in Orthopedics 9:101-107.

Stryker Biotech: OP-1 Implant® product information (2009).

Sampath TK. The Systems Biology of Bone Morphogenetic Proteins. In: Vukicevic S, Sampath, KT, editor. Bone Morphogenetic

(56) References Cited

OTHER PUBLICATIONS

Proteins: Systems Biology Regulators. Springer International Publishing; 2017. pp. 15-38 "Progress in Inflammation Research"—see item 5).

* cited by examiner

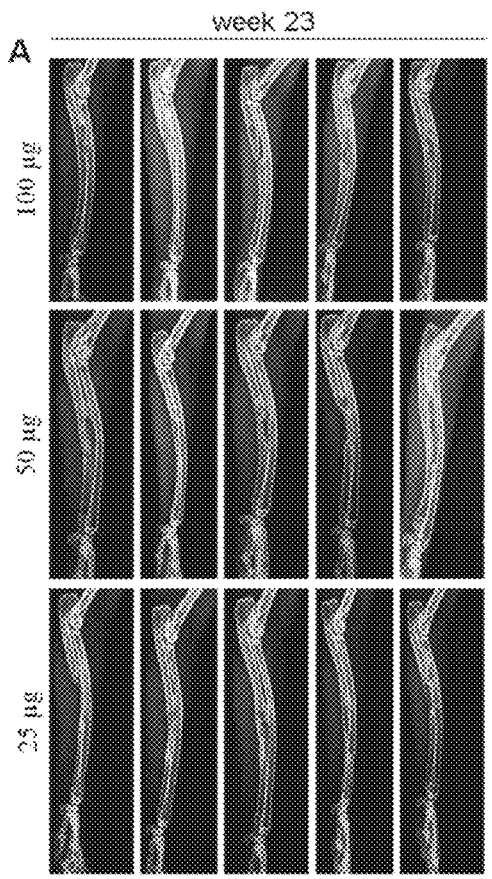
FIG. 6A
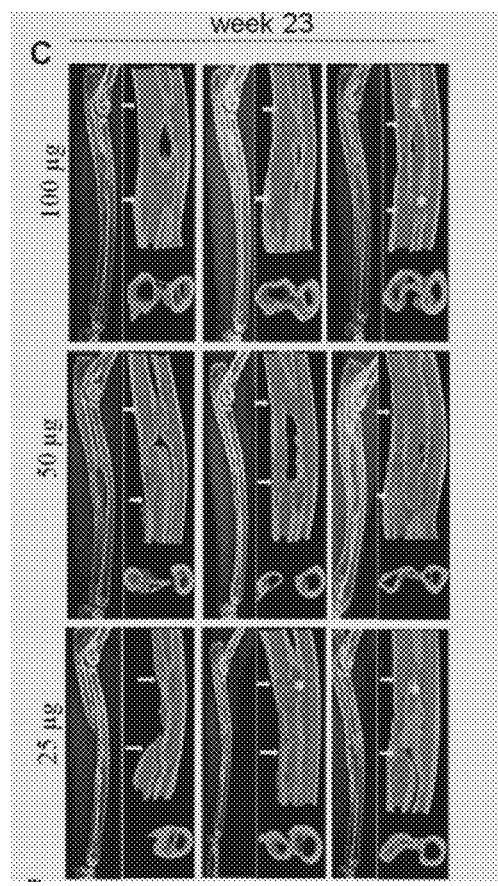
FIG. 6C
| Radiographic scoring | | | | | |
|---|---|---|---|---|---|
| | Animal No. | 1 | 2 | 3 | 4 | 5 |
| 100 µg | Score | 6 | 6 | 3 | 5 | 5 |
| | Animal No. | 6 | 7 | 8 | 9 | 10 |
| 50 µg | Score | 4 | 4 | 3 | 3 | 6 |
| | Animal No. | 11 | 12 | 13 | 14 | 15 |
| 25 µg | Score | 1 | 5 | 4 | 3 | 2 |
FIG. 6B
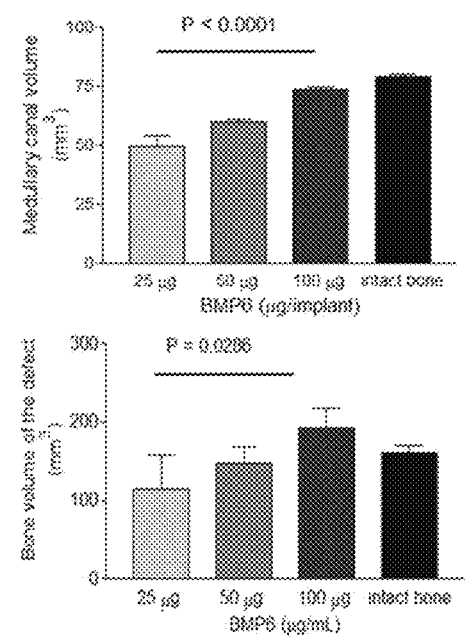
FIG. 6D FIG. 8B
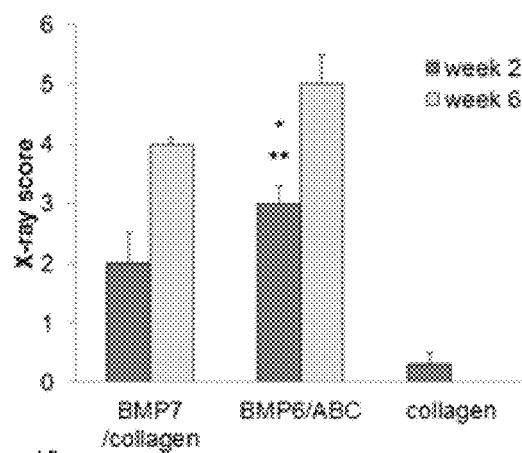
FIG. 8C
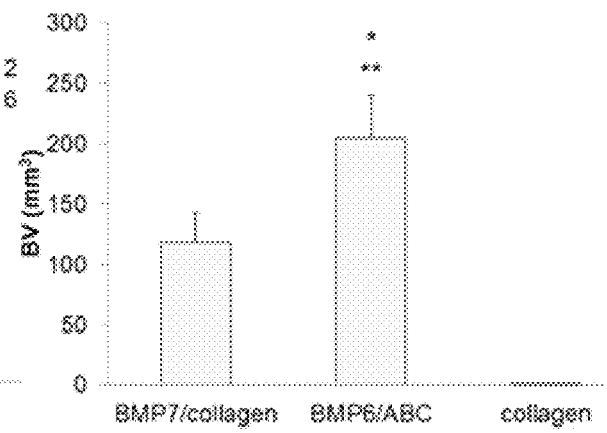
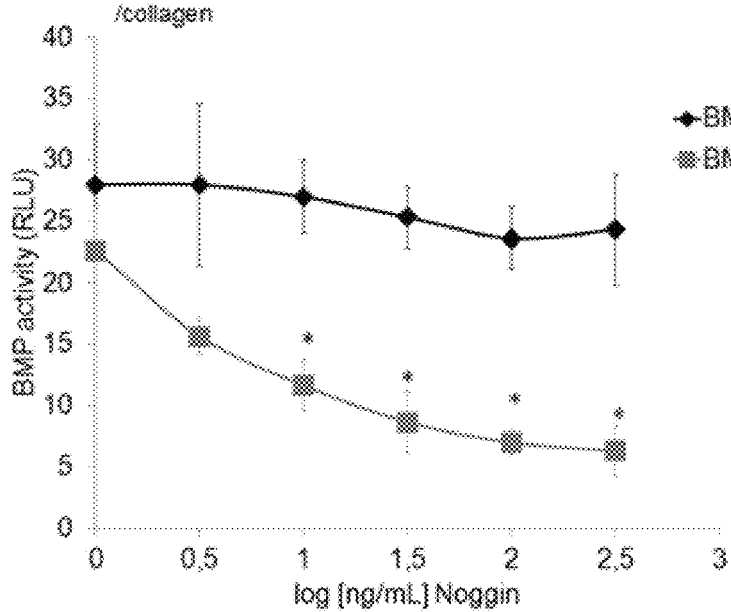
FIG. 8D

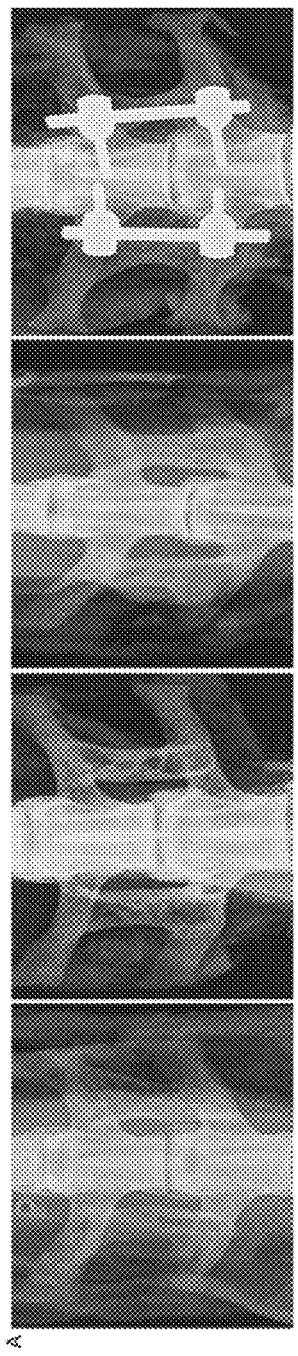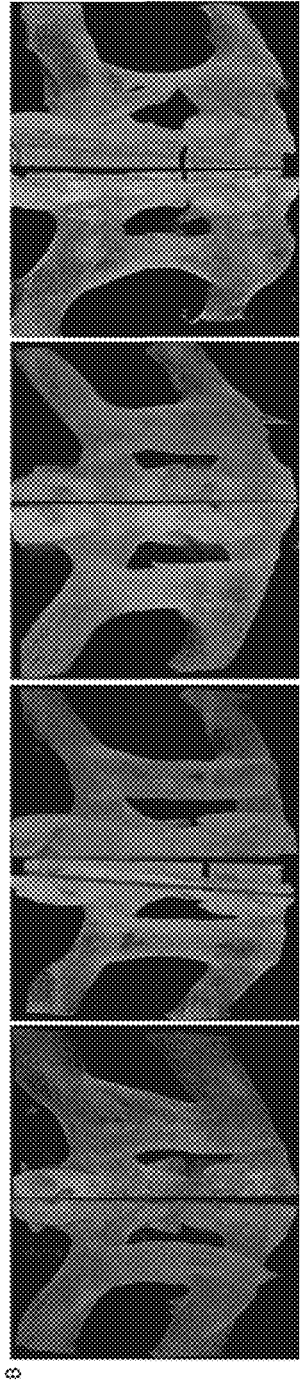
FIG. 12A
FIG. 12B

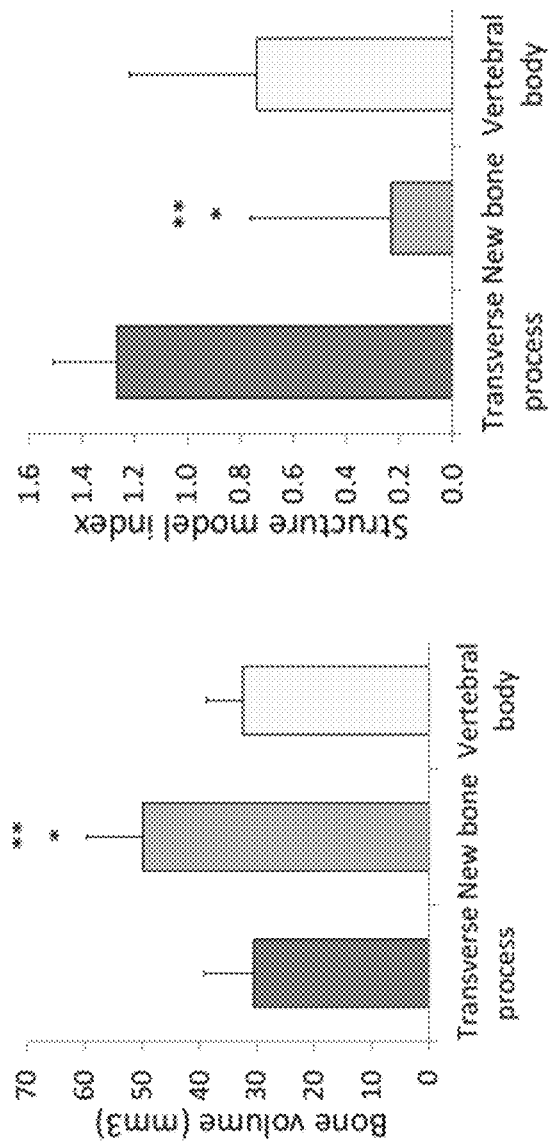
FIG. 13C
FIG. 13D
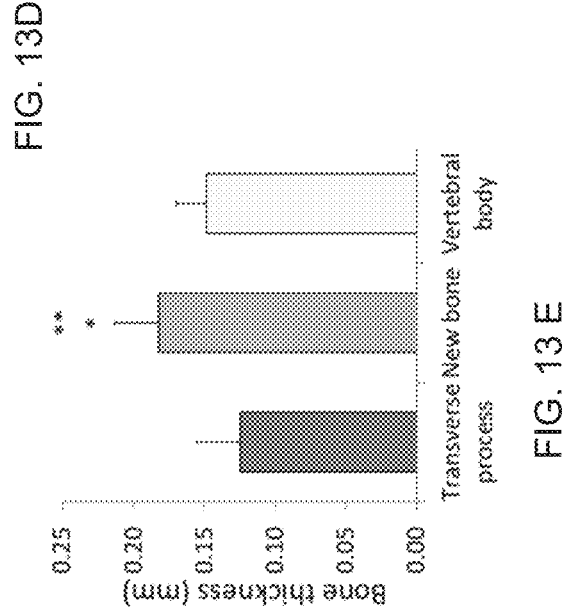
FIG. 13E

AUTOLOGOUS BONE GRAFT SUBSTITUTE COMPOSITION

FIELD OF THE INVENTION

The present invention relates to a composition, a preparation method of the composition, said composition capable of imitating "Live Autograft" for use in treating bone defects, inducing new bone formation and promoting bone growth. In a particular aspect, the invention relates to an injectable/extrudable/implantable autologous bone graft substitute composition (hereinafter referred to by abbreviation ABGS) for use in treatment of bone defects, inducing new bone formation and promoting bone growth for bone fracture healing, spinal fusions and to repair bone defects in bone reconstructive procedures of orthopedic and oral maxillofacial-dental surgeries.

BACKGROUND OF THE INVENTION

Bone grafts are employed in a variety of surgical procedures designed to promote growth of new bone to repair a bone defect, augment the bone growth at a particular site, promote fusion of adjacent bones to restore, enhance the stability of a skeletal structure and reduce back and leg pain suffered by an affected individual. In many situations, a surgical procedure employs a bone graft in conjunction with any of a variety of instrumentations, such as pedicle screws and rods, to secure the implanted bone graft and enhance stability while new bone grows to correct the defect.

Spinal fusion is a surgical procedure employed primarily to relieve the source of back and leg pain in an individual in which vertebral segments (vertebra-disc-vertebra) are damaged or inflamed. During a spinal fusion, two or more adjacent vertebral segments are fused to restrict motion and compression between the segments and thereby end or substantially mitigate pain and further degeneration that results from the motion or compression of damaged adjacent segments. Thus, the desired outcome of a spinal fusion procedure is to replace the original arrangement of two vertebrae separated by articular fibro-cartilage disc with a stable, continuous, load-bearing segment of bone, which in turn relieves pain and moderates further segmental degeneration (e.g., Anterior Lumbar Inter-body Fusion, ALIF).

In addition to relieve pain and further stabilize the spine in order to avoid compression, the two transverse processes at both sides in a given segment (level) are fused by forming new functional bone at ectopic sites using autograft or devitalized allograft segments or devitalized allograft particles enriched with the patient's bone marrow or allogenic demineralized bone matrix containing the patient's bone marrow (e.g., Posterolateral Lumbar Fusion, PLF). Surgeons use metal instruments like cages, screws and rods in order to help in fusing both the anterior (vertebral bodies) and posterior (vertebral processes) lumbar spine segments since immobilization (arthrodesis) of movement minimizes compression on the spinal cord nerves passing between the two lumbar vertebrae. To increase the rate of fusion, the instrumentation is supplemented by bone grafting to stimulate osteogenesis at either intervertebral (Anterior Lumber Inter-body Fusion, ALIF) or ectopic sites in between transverse processes (Posterolateral Lumbar Fusion, PLF), or both (Posterolateral Lumbar Inter-body Fusion, PLIF). See, for example, Mobbs, R. J. et al. Lumbar interbody fusion: techniques, indications and comparison of interbody fusion options including PLIF, TLIF, MI-TLIF, OLIF/ATP, LLIF and ALIF. J Spine Surg 1:2-18 (2015). A variety of disorders may be treated with spinal fusion including, but not limited to, degenerative disc disease (DDD), spondylolisthesis, spinal stenosis, scoliosis, infections, fractures, spinal dystrophy and various tumors.

Spinal fusion requires a material that serves to promote new bone growth to fuse adjacent vertebrae. For decades, the standard spinal fusion procedure has entailed a second incision into a patient to harvest autogenous bone chips (autograft) from the patient's iliac crest of the hip. The harvested bone chips are inserted into the area between the affected vertebrae and stabilized by appropriate instrumentation, such as pedicle screws and rods. This spinal fusion procedure employing autograft from the patient is also referred to as iliac crest bone graft (hereinafter referred to by abbreviation ICBG). The advantage of using ICBG is that the harvested bone chips have live bone marrow cells and immunologically compatible extracellular matrix with the patient's body and contain functional bone marrow elements including red and white blood cells and megakaryocytes. However, use of an ICBG requires the patient to sustain a second incision. The second incision to harvest bone for use as the autograft has been a concern in the field as it lengthens the surgical procedure and, therefore, the time the patient is under anesthesia, it provides another site for post-operative pain (see for example, Kim et al., Spine J. 9:886-92; 2009), and, as another incision in the patient, it increases the risk for infection. Furthermore, the amount of IGBG that could be harvested is limited.

To reduce such additional risks to the patient, a number of alternative implantable compositions have been developed and tested in an effort to replace the need for an autograft during the surgical procedure. Such alternative compositions may comprise allograft (for example, cadaver bone from a bone bank), demineralized bone matrix (DBM), various ceramics (calcium-based compounds), synthetic polymers, bone morphogenetic proteins (BMPs) and their analogs in conjunction with animal derived collagen scaffold, and various combinations thereof. See, for details, Gupta S, M. V., Gupta M C (2017) Biology of spine fusion and application of osteobiologics in spine surgery. In: Vukicevic S, Sampath. KT. (ed) Bone Morphogenetic Proteins: Systems Biology Regulators. Springer International Publishing. However, attempts to develop alternatives to autograft for spinal fusion have been met with their own particular challenges to achieve regulatory approval.

The INFUSE® Bone Graft/LT-CAGE lumbar tapered fusion device (Medtronic Sofamor Danek, Memphis, Tenn., USA) was approved in 2002 as a substitute for ICBG for treating DDD at one level (vertebra-disc-vertebra, ALIF) from L2 to S1 using an anterior approach in skeletally mature patients. The INFUSE® Bone Graft component consists of human bone morphogenetic protein-2 (rhBMP-2) applied to an absorbable, Bovine-Achilles Tendon derived, collagen sponge carrier that is used to fill a Lordotic Threaded (LT) cage component. Each device contains 12 milligrams of rhBMP-2 (in total), a sheet of collagen sheet soaked with 6 mg and filled separately in 2-LT cages that be inserted into intervertebral disc space. See, for details, INFUSE Bone Graft product information: Lumbar. (2002) Medtronic Sofamor Danek USA, Inc. In the approved surgical procedure, a device is implanted on each side of the affected vertebral level to promote stabilizing fusion on each side of the segment. The ability of the device to promote spinal fusion in various off-label posterior approaches has also been the subject of a number of studies. See, for example, Cahill et al., JAMA 302:58-66 (2009); Carragee, et al., Spine J 11:471-491 (2011). However, the off-label use produced unwanted safety concerns that led to a congressional hearing and FDA monitoring.

The AMPLIFY® bone graft substitute product (Medtronic) was originally designed and tested as an ICBG substitute for spinal fusion using a posterolateral approach (PLF). This ICBG substitute product delivered 40 mg of rhBMP-2 in a porous synthetic Slab that is composed of Bovine-Achilles Tendon derived collagen sponge impregnated with ceramic granules of hydroxyl apatite (HA) and tri-calcium phosphate (TCP) composite. Although the AMPLIFY® bone graft substitute product provided moderate spinal fusion in treating DDD, the United States Food and Drug Agency (FDA) refused to approve the product citing that a significant number of patients continue to experience low back pain and leg pain and concerns of possible cancer risks associated with the relatively high dose of rhBMP-2 and unwanted ectopic bone formation at sites away from the implant attributed to the larger amount of BMP-2 used in the device. See, for example, Executive Summary for P050036 Medtronic's AMPLIFY™ rhBMP-2 Matrix Orthopedic and Rehabilitation Devices Advisory Panel (2010) Food and Drug Administration.

The OP-1® Implant (Olympus/Stryker) is an implantable device for regenerating bone. The device contains recombinant human BMP-7 (rhBMP-7) dispersed within a bovine bone derived type I collagen. Owing to a failure to achieve a statistical difference in new bone formation over autograft, the OP-1® Implant received FDA approval only for humanitarian device exemption (HDE) use as an alternative to autograft in recalcitrant long bone non-union defects where the use of autograft is unfeasible and alternative treatments have failed. See, for example, Stryker Biotech OP-1 Implant® product information (2009).

An OP-1 Putty® is a composition that combines rhBMP-7, a bovine bone collagen, and a putty additive (carboxymethyl-cellulose). The OP-1 Putty® device was evaluated in a posterolateral fusion (PLF) clinical study but also did not achieve a statistical difference compared to autograft. The OP-1 Putty® has therefore been approved for HDE use in spinal fusion. See, for example, Stryker Biotech OP-1 Putty® product information (2009).

WO 2008/011192 A2 discloses a whole blood-derived coagulum device for treating a bone defect in an individual prepared by the steps comprising: (a) combining: (1) whole blood, (2) an osteogenic protein, (3) exogenously provided calcium ion, and (4) an exogenously provided fibrin-thrombin mixture, and (b) incubating the ingredients combined in step (a) until a gel-like stable coagulum is formed, wherein the exogenously provided calcium ion is present at a concentration that is effective to provide a homogeneous, cohesive, syringeable, injectable, and malleable coagulum gel. The coagulum gel of WO 2008/011192 A2 promotes the spreading of a bone morphogenetic protein or another osteogenic protein and triggering new bone formation distantly from the implant site, since the semi-solid jelly-like material quickly undergoes dissolution. Additionally, the whole blood-derived coagulum device disclosed in WO 2008/011192 A2 causes a shortfall of BMP at the implant site, which can lead to insufficient amount of BMP to promote new bone formation readily at the implant site.

WO 2009/129631 A1 discloses a biocompatible implant for bone repair comprising a flexible membrane with a biocompatible material having an inner and an outer surface fitted around the bone defect to create an enclosed void space, and a platelet-rich plasma (PRP) gel composition contained within the void space created by the membrane. The PRP gel composition of WO 2009/129631 A1 does not contain BMP for promotion of bone formation and is not concerned with using a "therapeutically effective amount" of the osteogenic BMP protein in the PRP gel composition that promotes bone growth at a desired location.

In addition to the use of autograft in spinal fusion, there are a variety of other orthopedic and dental indications that are treated using autograft. Such indications include various defects and fractures, such as diaphysis, distal radius fractures, tibial non-union fractures, high tibial osteotomy, osteoporotic fractures (vertebral compression fractures, atypical femoral fracture), defects from bone cysts, and defects from bone tumors, and also various oral, periodontal, and maxillofacial defects and anomalies. In addition, autograft is also in use to treat pseudo-arthrosis and pseudo-fractures associated with in rare musculoskeletal disorders like Hypophosphatasia (mutation in Tissue Non-Specific Alkaline Phosphatase gene), Neurofibromatosis Type I (mutation in Neurofibromin gene), Osteogenesis Imperfecta (mutation in Type I collagen gene). Depending on the severity of bone loss in such conditions, the amount of autograft that can be safely obtained from a patient may not be sufficient or may lack in bone quality (in compromised smokers, diabetic, steroid-users and osteoporotic patients) to provide the desired treatment. In such cases, biological bone graft substitutes that are safe and capable of inducing a robust bone formation that is restricted to the defect sites are much in demand. For comprehensive reading, Vukicevic S, Sampath T K, editors. Bone Morphogenetic Proteins: from Laboratory to Clinical Practice. Basel: Birkhauser Verlag, 2002; Vukicevic S, Sampath, K T, editor. Bone Morphogenetic Proteins: Systems Biology Regulators. Springer International Publishing; 2017.

To date, patients are limited to only a few products as possible alternatives to undergoing an autograft procedure for spinal fusion and other orthopedic procedures. Clearly, needs remain for improved compositions that can promote the level and quality of new bone growth required for successful repair of bone defects and for spinal fusion without the need for subjecting patients to the additional risks, pain, and limitations associated with autograft procedures.

In the present invention, autologous blood forms a coagulum gel comprising a fibrin-meshwork reinforced with a compression resistant matrix and containing an osteogenic bone morphogenetic protein, whereby the coagulum gel provides a sustained release of the osteogenic bone morphogenetic protein. The feature of the sustained release of the osteogenic bone morphogenetic protein from the autologous blood coagulum gel in combination with the compression resistant matrix is an essential feature resulting in new bone formation and creeping substitution of the compression resistant matrix via bone remodeling, and at the same time preventing the spreading of the BMP and new bone formation distant from the implant site.

SUMMARY OF THE INVENTION

The invention solves the problems illustrated in the background art by providing an autologous bone graft substitute composition (ABGS) that would serve as a mimetic to ICBG for use in promoting new bone growth at a site in an individual in need of treatment thereof. In a particular aspect, the invention relates to an injectable/extrudable/implantable autologous bone graft substitute composition for use in treating bone defects, inducing new bone formation and promoting bone growth for bone fracture healing, spinal fusions and to repair bone defects in bone reconstructive procedures of orthopedic and oral maxillofacial-dental surgeries.

In one embodiment the invention provides an autologous bone graft substitute composition for inducing new bone formation, promoting bone growth and treating of bone defect, wherein the composition comprises:
1) autologous blood (AB),
2) an osteogenic bone morphogenetic protein (BMP), and
3) a blood clotting agent selected from pharmacologically acceptable calcium, strontium or magnesium salts in ionic solution or nanoparticles and Ca++microsphere conjugates, and
4) a compression resistant matrix (CRM),
wherein the autologous blood forms a coagulum gel comprising osteogenic bone morphogenetic protein, calcium, strontium or magnesium salts and the compression resistant matrix (hereinafter referred to by abbreviation CRM).

Suitably, the blood clotting agent is present in a range from above 15 to 50 mm per ml of autologous blood.

The osteogenic bone morphogenetic protein is selected from BMP-6, BMP-2, BMP-7, BMP-4, BMP-5, BMP-6, BMP-9, BMP-12, and BMP-13, analogs thereof or, heterodimers thereof, and combinations thereof, in a range of from 0.002 mg per ml to 1 mg per ml of autologous blood.

In a preferred embodiment, osteogenic bone morphogenetic proteins are BMP-6 or BMP-7, preferably BMP-6.

The autologous blood (hereinafter referred to by abbreviation AB) in addition may comprise an autologous or allogenic platelet-rich plasma (hereinafter referred to by abbreviation PRP) or autologous blood (AB) may be substituted with Platelet-Rich Plasma (PRP).

A compression resistant matrix (CRM) is selected from the group consisting of: a bone allograft, bone autograft, a calcium phosphate-carbonate composite, a bioresorbable polymer or copolymer, calcium sulfate, a bioresorbable hydrogels, and combinations thereof.

In another embodiment of the invention, an autologous bone graft substitute composition for treating bone defects, inducing new bone formation and promoting bone growth comprises:
1) autologous blood,
2) an osteogenic bone morphogenetic protein selected from BMP-6, BMP-2, BMP-7, BMP-4, BMP-2, BMP-5, BMP-8, BMP-9, BMP-12, and BMP-13, analogs thereof or, heterodimers thereof, and combinations thereof, in a range of from 0.002 mg per ml to 1 mg per ml of autologous blood; and
3) a blood clotting agent selected from pharmacologically acceptable calcium, strontium or magnesium salts in ionic solution or nanoparticles and Ca++microsphere conjugates;
wherein the autologous blood forms a coagulum gel comprising osteogenic bone morphogenetic protein and calcium, strontium or magnesium salts.

Suitably the blood clotting agent is present in a range from above 15 to 50 mM per ml of autologous blood.

Suitably osteogenic bone morphogenetic protein is BMP-6 or BMP-7, preferably it is BMP-6.

The autologous blood (AB) in addition may comprise an autologous or allogenic platelet-rich plasma (PRP) or autologous blood (AB) is substituted with autologous Platelet-Rich Plasma (PRP).

In another embodiment of the invention, an autologous bone graft substitute composition of implant for inducing new bone formation, promoting bone growth and treating bone defect comprises:
1) autologous blood;
2) an osteogenic bone morphogenetic protein selected from BMP-6, BMP-2, BMP-7, BMP-4, BMP-5, BMP-8, BMP-9, BMP-12, and BMP-13, analogs thereof or, heterodimers thereof, and combinations thereof, in a range of from 0.002 mg per ml to 1 mg per ml of autologous blood; and
3) a compression resistant matrix (CRM) selected from the group consisting of a bone autograft, bone allograft, hydroxyapatite, tri-calcium phosphate, and combinations thereof;
wherein the autologous blood forms a coagulum gel comprising a fibrin-meshwork reinforced with the compression resistant matrix, the coagulum gel containing the osteogenic bone morphogenetic protein, whereby the coagulum gel provides a sustained release of the osteogenic bone morphogenetic protein.

Suitably osteogenic bone morphogenetic protein is BMP-6. Instead of the osteogenic bone morphogenetic protein BMP-6, osteogenic bone morphogenetic protein selected from BMP-6, BMP-2, BMP-7, BMP-4, BMP-5, BMP-8, BMP-9, BMP-12, BMP-13, analogs thereof or, heterodimers thereof and combinations thereof can be used.

Preferably, the compression resistant matrix (CRM) is selected from the group consisting of a bone autograft, bone allograft and/or a calcium phosphate-carbonate composite.

In another preferred embodiment, an osteogenic bone morphogenetic protein is BMP-6 in a range of 2 to 200 μg per ml of autologous blood.

In another preferred embodiment, an osteogenic bone morphogenetic protein is BMP-6 in an amount of 100 μg per ml of autologous blood.

In another preferred embodiment, a solubilized osteogenic bone morphogenetic protein is contained in a lyophilized form in a compression resistant matrix.

In another embodiment, an autologous bone graft substitute composition described herein may further comprise an exogenously provided population of patient's bone marrow aspirate that contains osteoprogenitor cells.

In another embodiment, an autologous bone graft substitute composition described herein may further comprise an exogenously provided population of ex vivo expanded mesenchymal stem cells (osteoprogenitor cells) from patients' bone marrow.

In another embodiment, an autologous bone graft substitute composition described herein may further comprise an exogenously provided population of ex vivo expanded mesenchymal stem cells (osteoprogenitor cells) from patients' adipose tissue.

In another embodiment, an autologous bone graft substitute composition described herein may further comprise an exogenously provided population of ex vivo expanded mesenchymal stem cells (osteoprogenitor cells) from patients' periosteal layer (periosteum).

In another embodiment, an autologous bone graft substitute composition described herein may further comprise an exogenously provided minced tissue fragments prepared from patient's adjacent local bone, suitable skeletal muscle and/or fascia.

In another embodiment, an autologous bone graft substitute composition described herein may further comprise an exogenously provided population of ex vivo expanded mesenchymal stem cells (osteoprogenitor cells) derived from allogenic bone marrow or adipose tissue or periosteum from patients' immune-matched individuals.

In another embodiment, an autologous bone graft substitute composition described herein may further comprise an exogenously provided population of ex vivo expanded mesenchymal stem cells (osteoprogenitor cells) derived from allogenic umbilical cord.

In another embodiment, an autologous bone graft substitute composition described herein may further comprise an allogenic or exogenously provided patient's Platelet-Rich Plasma (PRP), a source for fibrin-mesh work and growth factors (e.g., PDGF, IGF, VEGF and TGF-beta).

In another embodiment, an autologous bone graft substitute composition described herein as a compression resistant matrix is selected from the group consisting of bone autograft, bone allograft (for example prepared from cortical bone or trabecular bone or both), a calcium phosphate-carbonate composite (hereinafter referred to by abbreviation as ceramics), a thermosensitive bioresorbable polymers or copolymers (e.g., polymers and co-polymers of lactide or glycolide and combinations thereof), calcium sulfate, bioresorbable hydrogels and combinations thereof. Said calcium phosphate-carbonate composite is selected from the group consisting of: hydroxyapatite (HA), tri-calcium phosphate (TCP), and TCP/HA conjugates.

In yet another embodiment, an autologous bone graft substitute composition described herein may further comprise allogenic demineralized bone matrix.

In another embodiment of the invention, an autologous bone graft substitute composition described herein may further comprise a bone graft substitute that may further comprise a reverse phase thermosensitive bioresorbable polymer. Said reverse phase thermosensitive bioresorbable polymer may be mixed in autologous blood (AB) that assumes the rheology of the composition comprising the AB, BMP and the CRM so that it can be injected at room temperature in liquid phase, and as temperature increases to body temperature (37° C.) it forms a biocompatible gel at the delivery/implant site. Therefore, the composition provides a non-invasive injectable composition that contains a BMP, a CRM and a reverse phase thermosensitive bioresorbable polymer within Autologous Blood. This formulation can be administered non-invasively, e.g., by injection, thus overcoming the limitations associated with currently marketed solid bone graft substitute. The injectable ABGS effectively induces new bone formation, in a standard rat model of ectopic bone formation. This injectable composition enables new bone formation at relatively low BMP concentrations as it binds tightly to plasma proteins being retained by the reverse phase thermosensitive bioresorbable polymer at body temperature for sustainable duration.

In another embodiment, the invention provides a method of preparation of an autologous bone graft substitute composition for treating a bone defect, inducing new bone formation and promoting a bone growth, the method comprising steps of:
1 mixing:
  a. autologous blood (AB), or the autologous blood and a Platelet-Rich Plasma (PRP) or a Platelet-Rich Plasma (PRP)
  b. an osteogenic bone morphogenetic protein selected from BMP-6, BMP-2, BMP-7, BMP-4, BMP-5, BMP-9, BMP-12, and BMP-13, analogs thereof or, heterodimers thereof, and combinations thereof, in a range of from 0.002 mg per ml to 1 mg per ml of autologous blood; and c. a compression resistant matrix selected from the group consisting of a bone autograft, bone allograft, hydroxyapatite (HA), tri-calcium phosphate (TCP), and combinations thereof;
2) incubating components of step (1) for a period sufficient to form a coagulum gel comprising a fibrin-meshwork reinforced with the compression resistant matrix, the coagulum gel containing the osteogenic bone morphogenetic protein, whereby the coagulum gel and the compression resistant matrix provide a sustained release of the osteogenic bone morphogenetic protein.

In a further embodiment, a method of preparation of an autologous bone graft substitute composition for treating a bone defect, inducing new bone formation and promoting a bone growth further comprising adding in step (1) a blood clotting agent, the blood clotting agent is selected from the group consisting of pharmacologically acceptable calcium, strontium or magnesium salts in ionic solution or nanoparticles and Ca++ microsphere conjugates; wherein the blood clotting agent is added in a range from above 15 to 50 mM per ml of autologous blood.

In another embodiment, the invention provides a preparation method of an autologous bone graft substitute composition for treating a bone defect, inducing new bone formation and promoting bone growth, wherein the ABGS is prepared by the steps comprising:
1) combining:
  a. autologous blood,
  b. an osteogenic bone morphogenetic protein selected from BMP-6, BMP-2, BMP-7, BMP-2, BMP-9, BMP-12, and BMP-13, analogs thereof or, heterodimers thereof, and combinations thereof,
  c. a blood clotting agent selected from pharmacologically acceptable calcium, strontium or magnesium salts in ionic solution or nanoparticles and Ca++ microsphere conjugates;
  d. a compression resistant matrix (CRM),
  e. optionally an exogenously provided population of ex vivo expanded autologous or allogenic mesenchymal cells (osteoprogenitor cells) from bone marrow, adipose tissue, periosteal layer and/or umbilical cord; and/or
  f. optionally a demineralized bone matrix;
2) incubating the components of step (1) for a period sufficient to form a coagulum gel.

In another embodiment, the invention provides a preparation method of an autologous bone graft substitute composition for treating a bone defect, inducing new bone formation and promoting bone growth, wherein the ABGS is prepared by the steps comprising:
1) combining
  a. autologous blood,
  b. an osteogenic bone morphogenetic,
  c. a blood clotting agent selected from pharmacologically acceptable calcium, strontium or magnesium salts in ionic solution or nanoparticles and Ca++ microsphere conjugates;
  d. a compression resistant matrix (CRM),
  e. a reverse phase thermosensitive bioresorbable polymer,
  f. optionally an exogenously provided population of ex vivo expanded autologous or allogenic mesenchymal cells (osteoprogenitor cells) from bone marrow, adipose tissue, periosteal layer or umbilical cord, and/or
  g. optionally a demineralized bone matrix; and 2) incubating the components of step (1) for a period sufficient to form a coagulum gel having the rheology so that it can be injected at room temperature in liquid phase, and as temperature increases to body temperature (37° C.) forms a biocompatible gel at the delivery/implant site.

An autologous bone graft substitute composition described herein may be extruded, implanted or injected (for example, using a syringe) into a site of a bone defect or a site requiring new bone growth (for example, spinal fusion, skeletal augmentations).

Preferably, an osteogenic BMP useful in an ABGS composition described herein is selected from the group consisting of BMP-2, BMP-4, BMP-5, BMP-6, BMP-7, BMP-8, BMP-9, BMP-12, BMP-13, analogs thereof or, heterodimers thereof, and combinations thereof. More preferably, the osteogenic BMP is BMP-6.

In another embodiment, an osteogenic BMP is present in an ABGS described herein in an amount ranging from 0.002 mg to 1 mg of osteogenic protein BMP (preferably BMP-6) per milliliter (ml) of autologous blood.

In another embodiment, an autologous bone graft substitute composition described herein comprises a compression resistant matrix selected from the group consisting of bone autograft, bone allograft, calcium phosphate-carbonate composite, a bioresorbable polymer or copolymer, and combinations thereof. Preferably, Calcium-phosphate-carbonate composition is selected from the group consisting of: hydroxyapatite (HA), tri-calcium phosphate (TCP), and combinations thereof.

In another embodiment, the invention provides a kit for preparing an autologous bone graft substitute implant for inducing new bone formation comprising:
 a butterfly needle set for autologous blood collection;
 a lyophilization container holder comprising a needle protected with a rubber sleeve;
 a sterile tubing connecting the butterfly needle and the lyophilization container holder;
 a tubing clamp for releasing vacuum or to stop flow of blood;
 a lyophilization container with a rubber stopper containing lyophilized osteogenic bone morphogenic protein BMP mixed with compression resistant matrix;
 wherein the compression resistant matrix is selected from the group consisting of bone allograft, bone autograft, hydroxyapatite, tri-calcium phosphate, and combinations thereof, an osteogenic bone morphogenetic protein is selected from BMP-6, BMP-2, BMP-7, BMP-4, BMP-5, BMP-8, BMP-9, BMP-12, BMP-13, analogs thereof, heterodimers thereof, and combinations thereof. Preferably, the osteogenic bone morphogenic protein is BMP-6.

In another embodiment, the invention provides a method of preparation of an autologous bone graft substitute composition, comprising the steps of:
 1) mixing:
  a. autologous blood;
  b. an osteogenic bone morphogenetic protein selected from BMP-6, BMP-2, BMP-7, BMP-4, BMP-5, BMP-8, BMP-9, BMP-12, BMP-13, analogs thereof or, heterodimers thereof, and combinations thereof, in a range of from 0.002 mg per ml to 1 mg per ml of autologous blood;
  c. a compression resistant matrix selected from the group consisting of bone autograft, bone allograft, hydroxyapatite, tri-calcium phosphate, and combinations thereof;

2) incubating components of step (1) for a period sufficient to form a coagulum gel comprising a fibrin-meshwork reinforced with the compression resistant matrix, the coagulum gel containing the osteogenic bone morphogenetic protein, whereby the coagulum gel and the compression resistant matrix provide a sustained release of the osteogenic bone morphogenetic protein;

The method of preparation of an autologous bone graft substitute composition further comprising:
 a. mixing the osteogenic bone morphogenic protein in aqueous solution with the compression resistant matrix in a sterile lyophilization vial wherein a volume of osteogenic bone morphogenic protein aqueous solution added to the compression resistant matrix is optimized for complete wetting of the compression resistant matrix;
 b. lyophilization of the osteogenic bone morphogenic protein in aqueous solution and the compression resistant matrix;
 c. adding autologous blood; and
 d. incubating the lyophilized osteogenic bone morphogenic protein and the compression resistant matrix composite in autologous blood for a period sufficient to form a biomechanically stable blood clot around the lyophilized osteogenic bone morphogenic protein and the compression resistant matrix.

In a further embodiment, a method of preparation of an autologous bone graft substitute composition for treating a bone defect, inducing new bone formation and promoting a bone growth further comprising adding in step (1) a blood clotting agent, the blood clotting agent is selected from the group consisting of pharmacologically acceptable calcium, strontium or magnesium salts in ionic solution or nanoparticles and Ca++microsphere conjugates; wherein the blood clotting agent is added in a range from above 15 to 50 mM per ml of autologous blood.

Preferably, an osteogenic bone morphogenetic protein is BMP-6 in a range 2 µg per ml to 200 µg per ml of autologous blood.

Yet in a further embodiment, an osteogenic bone morphogenetic protein is BMP-6 in an amount of 100 µg per ml of autologous blood.

The present invention also provides an autologous bone graft substitute composition for inducing new bone formation, promoting bone growth and treating of bone defect, wherein the composition comprises:
 (i) autologous blood;
 (ii) an osteogenic bone morphogenetic protein selected from BMP-6, BMP-2, BMP-7, BMP-4, BMP-5, BMP-8, BMP-9, BMP-12, and BMP-13, analogs thereof or, heterodimers thereof, and combinations thereof, in a range of from 0.002 mg per ml to 1 mg per ml of autologous blood;
 (iii) a compression resistant matrix selected from the group consisting of a bone autograft, bone allograft, hydroxyapatite, tri-calcium phosphate, and combinations thereof; and
 (iv) a blood clotting agent in a range from above 15 mM to 50 mM per ml of autologous blood; the blood clotting agent being selected from the group consisting of: pharmacologically acceptable calcium, strontium or magnesium salts in ionic solution or nanoparticles and Ca++microsphere conjugates;
wherein the autologous blood forms a coagulum gel comprising osteogenic bone morphogenetic protein and the autologous blood clotting agent, said coagulum gel having a structure and rheological properties that provide a sustained release of the osteogenic bone morphogenetic protein.

In a preferred embodiment, the osteogenic bone morphogenetic protein is BMP-6 in the range of 25 to 100 μg per 1.5 ml of autologous blood coagulum gel.

The present invention also provides a method of preparation of an autologous bone graft substitute composition.

The present invention also provides a method of inducing or promoting bone growth by treatment of a bone with an autologous bone graft substitute composition.

An autologous bone graft substitute composition described herein may also be used in treatment any of a variety of bone defects in which new bone formation or growth is required. Such bone defects that may be treated by using the autologous bone graft substitute composition described herein include, but are not limited to, a diaphysis fracture, a distal radius fracture, a tibial non-union, an osteoporotic fracture, a bone cyst defect (for example, where new bone must be generated to fill a void formerly occupied by the cyst), a bone tumor defect (for example, where new bone must be generated to replace bone that has been lost by cancer or that has been removed by surgery), pseudoarthrosis and pseudo-fractures associated with congenital skeletal disorders (example Hypophosphatasia, Neurofibromatosis Type I, Osteogenesis Imperfecta) an osteoporotic fracture (for example, a vertebral compression fracture or an atypical diaphysis fracture), an oral bone defect (for example, various defects of the teeth), a periodontal defect, and a maxillofacial defect or anomaly (including augmentations to bone in the jaw, face, and head).

The autologous bone graft substitute composition (ABGS) described herein may also be used to promote new bone growth in any of a variety of orthopedic and dental indications including, but not limited to, spinal fusion, high tibial osteotomy, and maxillofacial augmentations. In the ABGS, BMP is combined with autologous blood coagulum which is then reinforced with a compression resistant matrix to guide the formation of new bone tissue. BMP-6 is a preferred BMP as it does not bind avidly to the BMP antagonist, Noggin (Song et al., J Biol Chem.; 285(16): 12169-80 (2010), which is abundant in bone, and also binds to most of the BMP-6 type I and type II receptors (unlike BMP2 and BMP7) for signaling. An autologous blood coagulum (ABC) is a preferred substrate for the delivery of BMP as a number of plasma proteins bind tightly to BMP6 resulting in the sustained and linear release of BMP6 over seven to ten days. The ABC also provides a permissive environment for osteogenesis in the presence of a compression resistant matrix (CRM) without provoking inflammation and immune responses, in sharp contrast to the inflammation seen when BMPs are implanted with animal-derived collagen as substratum. Furthermore, autologous blood contains osteoprogenitors cells (mesenchymal stem cells) which can readily respond to BMP-6 during the formation of coagulum to initiate new bone formation at the implant site.

The autologous bone graft substitute composition (ABGS) as described above may also be used to enhance bone mineral density of the femoral head and vertebral body in severe osteopenia patients suffering from postmenopausal or senile or steroid induced osteopenia. These severe osteopenia patients may suffer hip and vertebral fractures upon falling down. In these patients, small volumes of the ABGS may be injected into trabecular bone at multiple sites with small volume to promote bone growth and enhance bone mineral density of femoral head and vertebral body.

BRIEF DESCRIPTION OF THE DRAWINGS

FIGS. 6A and 6C show roentgenogram and respectively Micro CT rabbit ulna analyses illustrating a dose-dependent response;

FIG. 6B shows radiographic scoring of X-rays of FIG. 6A;

FIG. 6D shows morphometric analysis of medullary canal and bone volume of the defect;

FIG. 8B shows a graph illustrating X-ray score of rabbit ulna treated with rhBMP7 in collagen and rhBMP6 in an Autologous Blood Coagulum (ABC) and only with collagen as represented at weeks 6 and 2;

FIG. 8C shows a graph illustrating bone volume (BV) of rabbit ulna treated with rhBMP7 in collagen and rhBMP6 in an Autologous Blood Coagulum (ABC) and only with collagen as represented at weeks 6 and 2;

FIG. 8D shows a graph illustrating activity of BMP6 and BMP7 in dependence of Noggin;

FIG. 12A shows x-rays of spinal fusion in sheep treated with 62.5 µg/ml rhBMP6 and 187.5 µg/ml rhBMP6 with allograft bone, and allograft bone and instrumentation.

FIG. 12B shows the same sheep specimen following µCT scanning;

FIGS. 13C to 13E show µCT quantitative analysis of bone volume
(C), structure model index (D), and bone thickness (E);

DETAILED DESCRIPTION OF THE INVENTION

Figure 1:
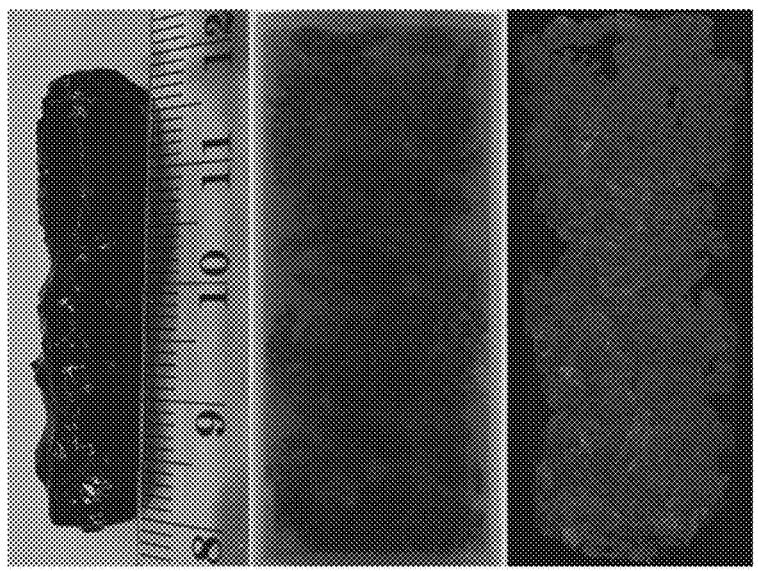
FIG. 1A shows a photomicrograph of an ABGS prepared by method #2 or #3 and a CRM from human blood from a volunteer. Human allograft from tissue bone bank is used as a CRM; left is a gross-picture, the center is x-ray and right is micro-CT scan.
FIG. 1B illustrates a cutting test of the ABGS of FIG. 1A.
FIG. 1C is a graph illustrating rheological properties of ABGS of FIG. 1A determined by stiffness, elasticity and strain.
Figure 1A:
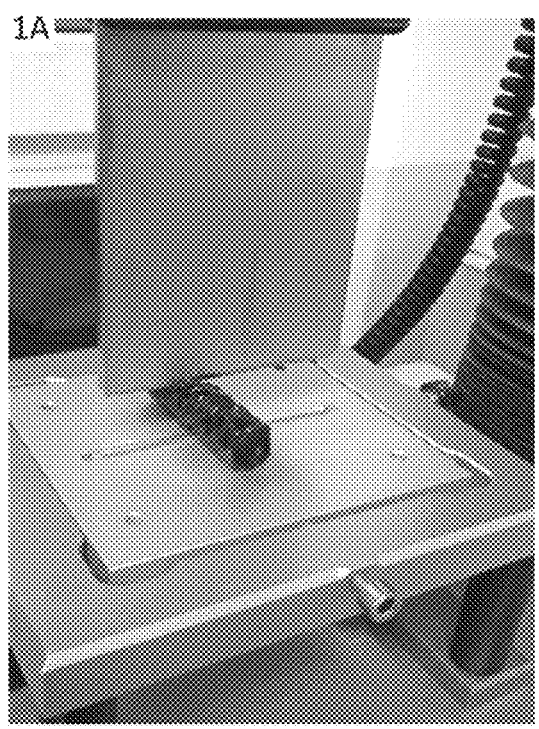
Figure 1B:
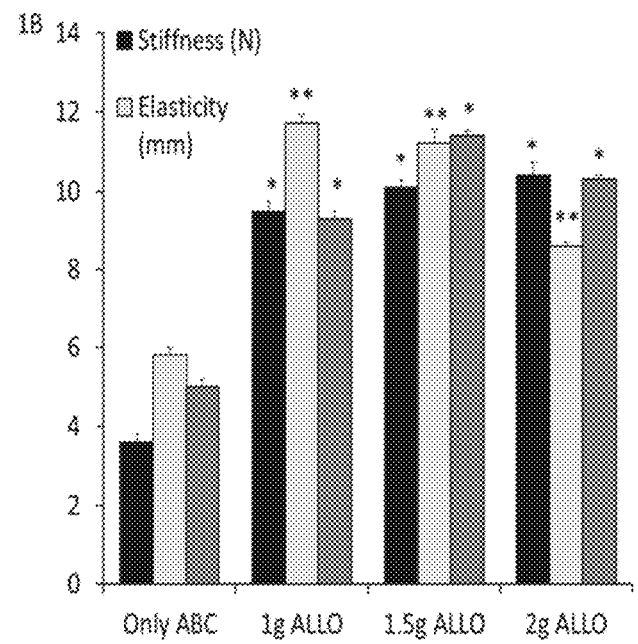

The invention provides an autologous bone graft substitute composition (ABGS) for use in treating bone defects, inducing new bone formation and promoting new bone growth at a desired site. The autologous bone graft substitute composition according to the invention may advantageously be used in place of autograft in procedures for generating or restoring bone at a particular site in an individual in need of treatment thereof.

The autologous bone graft substitute composition according to one embodiment of the invention is formed by combining (mixing) a set of components comprising a sample of autologous blood, an osteogenic bone morphogenetic protein (preferably BMP-6), and a compression resistant matrix (CRM). Said components are incubated for a period sufficient to form a coagulum gel, said coagulum gel comprising a fibrin-meshwork reinforced with the compression resistant matrix, the coagulum gel containing the osteogenic bone morphogenetic protein, whereby the coagulum gel and the compression resistant matrix provides a sustained release of the osteogenic bone morphogenetic protein. The autologous bone graft substitute composition according to another embodiment of the invention may be formulated by first precipitating or lyophilizing an osteogenic bone morphogenetic protein (preferably BMP-6) on to a compression resistant matrix in a specific geometrical shape (e.g., particulate, cylinder or slab) and then adding autologous blood and incubating for a period sufficient to form a biomechanically stable blood clot around the lyophilized combination of osteogenic bone morphogenetic protein and the compression resistant matrix.

The autologous bone graft substitute composition according to further embodiment of the invention is formed by combining (mixing) a set of components comprising a sample of autologous blood, an osteogenic bone morphogenetic protein (preferably BMP-6), and a blood clotting agent. The blood clotting agent is selected from the group consisting of pharmacologically acceptable calcium, strontium or magnesium salts in ionic solution or nanoparticles and Ca++microsphere conjugates, and wherein the blood clotting agent is present in a range from above 15 to 50 mM per ml of autologous blood.

According to the invention, the autologous bone graft substitute composition described herein can be readily implanted or injected or otherwise applied to a site in which there is a need or desire for a new bone growth.

The autologous bone graft substitute composition essentially mimics the "Live Autograft" in a way:
1) it employs autologous blood which does not provoke inflammatory cytokine storm and foreign-body reaction because it is masking the surface of compression resistant matrix (either as particles, cylinders or slabs) to mask T-cells recognition as foreign material (e.g., high mineral content ceramics at ectopic site),
2) it provides circulating osteoprogenitors trapped in the blood coagulum which immediately respond BMP,
3) it does not cause immune responses with generation of antibodies unlike conventional animal derived collagen that may act as an adjuvant for immune reaction to recombinant BMP, 4) it allows BMP to bind tightly to plasma proteins within fibrin mesh-work whereby the BMP remains locally available or is slowly released at the implant site over several days to activate the BMP receptors on recruited mesenchymal stem cells for osteogenic responses.
5) The compression resistant matrix particles in the graft are biocompatible and also provide good handing properties. Furthermore, the mineral content (hydroxyapatite) undergoes a creeping substitution as it is replaced with newly formed bone.
6) BMP-6 is preferred BMP as it does not bind avidly to Noggin (Song et al., J Biol Chem.; 285(16):12169-80 (2010), a natural BMP antagonist abundant in bone, therefore it allows the use of lower dose as compared to BMP-2 or BMP-7 which lowers the safety concerns and avoids the use of excessive doses of BMP in the clinic.

An autologous bone graft substitute composition according to another embodiment of the invention may be formulated by combining (mixing) a set of components comprising a sample of autologous blood, an osteogenic bone morphogenetic protein (BMP), a compression resistant matrix (CRM), and a reverse phase thermosensitive bioresorbable polymer; and incubating the components for a period sufficient to form a coagulum gel having the rheology so the composition can be injected at room temperature in a liquid phase, and as temperature increases to body temperature (suitably 37° C.) forms a biocompatible gel at the delivery/implant site.

In order that the invention may be more clearly understood, the following terms are defined. The terms "bone morphogenetic protein", "BMP", "osteogenic BMP", and "morphogen" are synonymous and refer to any member of a particular subclass (i.e., the BMP family) of the transforming growth factor-beta (TGF-ß) super family of proteins (see, e.g., Massagué J (1998) TGF-β signal transduction. Annu Rev Biochem 67: 753-791; Sampath T K, Rueger D C (1994) Structure, function and orthopedic application of osteogenic protein-1 (OP-1). Complications in Orthopedics 9:101-107 (1994); U.S. Pat. Nos. 4,968,590; 5,011,691; 5,674,844; 6,333,312). All such BMPs have a signal peptide, pro-domain, and a carboxy-terminal (mature) domain. The carboxyl-terminal domain is the mature form of the BMP monomer and contains a highly conserved region characterized by seven cysteines, called "7-Cysteine Domain" a hall mark of BMP-Family proteins that form a cysteine knot (see, Griffith et al., Proc. Natl. Acad. Sci. USA., 93: 878-883 (1996).

BMPs were originally isolated from mammalian bone using protein purification methods (see, e.g., Sampath, et al., Proc. Natl. Acad. Sci. USA 84: 7109-7113 (1987);
Wang et al., Proc. Natl. Acad. Sci. USA 85: 9484-9488 (1988); Sampath, et al., J. Biol. Chem. 265: 13198-13205 (1990); U.S. Pat. No. 5,496,552). However, BMPs have also been detected in or isolated from other mammalian tissues and organs including kidney, liver, lung, brain, muscle, teeth, and gut. BMPs may also be produced using standard in vitro recombinant DNA technology for expression in prokaryotic or eukaryotic cell cultures (see, e.g., Wang et al., Proc. Natl. Acad. Sci. USA, 87: 2220-2224 (1990); Wozney et al., Science, 242: 1528-1534 (1988)). Some BMPs are commercially available for local use as well (e.g., BMP-7 is manufactured and distributed for treatment of long bone non-union fractures by Stryker (Kalamazoo, Mich., U.S.). BMP-2 is manufactured and distributed for long bone acute fractures by Wyeth (Madison, N.J., U.S.) and also for spinal fusions in the InFUSE® bone graft that employs a processed bovine Type I collagen sponge carrier in combination with an implantable lordotic threaded cage (LT/CAGE® Lumbar Tapered Fusion Device by Medtronic Sofamor Danek USA, Inc.; Memphis, Tenn., U.S.).

BMPs normally exist as dimers of the same monomeric polypeptides (homodimers) held together by hydrophobic interactions and at least one inter-chain (between monomers) disulfide bond. BMPs useful in the compositions and methods described herein are those that have osteogenic activity, i.e., the ability to stimulate bone formation. Osteogenic (or "osteoinductive") activity may be detected using any of a variety of standard assays. Such osteogenic assays include ectopic bone formation assays in which a carrier matrix comprising collagen and a BMP is implanted at an ectopic site in a rodent and then monitored for bone formation (Sampath T K and Reddi A H Proc. Natl. Acad. Sci. USA, 78: 7599-7603 (1981). In a variation of such an assay, the matrix may be implanted at an ectopic site and the BMP administered to the site, e.g., by intravenous injection into the rodent. Another way to assay for BMP osteogenic activity is to incubate cultured mesenchymal progenitor cells with a BMP and then monitor the cells for differentiation into chondrocytes and/or osteoblasts (see, e.g., Asahina et al., Exp. Cell. Res., 222: 38-47 (1996)). BMPs that have osteogenic activity and that are therefore useful in the compositions and methods described herein include, but are not limited to, BMP-2, BMP-4, BMP-6, BMP-7, BMP-9, BMP-12, BMP-13, analogs thereof or, heterodimers thereof, whether purified from a natural source if any, produced recombinant by eukaryotic (e.g., mammalian, yeasts, insects, fish) or prokaryotic (e.g., bacterial) cells, or produced in whole or in part by in vitro protein synthesis methods. A BMP that has an osteogenic activity may also possess one or more other beneficial pharmacological activities, such as the ability to restore or regenerate damaged soft tissues or organs, e.g., ischemic kidneys (Vukicevic et al., J. Clin. Invest., 102: 202-214 (1998).

The term "pharmaceutically acceptable" refers to a material that is not biologically, chemically, or in any other way incompatible with body chemistry and metabolisms and also does not adversely affect the desired, effective activity of an osteogenic BMP or any other component in a composition that may be administered to an individual to promote bone growth according to the invention. one or more named elements or steps also describes the corresponding, more limited, composition or method "consisting essentially of" (or "which consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and close-ended composition or method "consisting of" (or "which consists of") the named elements or steps to the exclusion of any other unnamed element or step. In any composition or method disclosed herein, known or disclosed equivalents of any named essential element or step may be substituted for that element or step. Unless indicated otherwise, the meaning of other terms is the same as understood and used by persons skilled in the art, including the fields of orthopedic surgeries, medicine, immunology, biochemistry, molecular biology, and tissue regeneration.

The BMP present in a bone graft substitute described herein promotes new bone growth from progenitor cells that are present in, or migrate into the defect site where the bone graft substitute is implanted. Any osteogenic bone morphogenetic protein (BMP) may be used in the compositions and methods described herein, including analogs thereof, heterodimers of two BMPs, and combinations (mixtures) of two or more BMPs. Preferred osteogenic BMPs useful in a bone graft substitute described herein include, without limitation, BMP-2, BMP-4, BMP-5, BMP-6, BMP-7, BMP-9, BMP-12, BMP-13, analogs thereof or, heterodimers thereof, and combinations thereof. Even more preferred for use in a bone graft substitute described herein is an osteogenic BMP selected from BMP-2, BMP-4, BMP-6, BMP-7, analogs thereof or, heterodimers thereof, and combinations thereof. Most preferably, the BMP used in the autologous bone graft substitute composition described herein is BMP-6.

Bone morphogenetic proteins (BMPs) are used clinically to induce new bone formation in spinal fusions and long bone nonunion fractures. However, large amounts of BMPs are needed to achieve these effects. BMPs were also found to increase the expression of naturally occurring BMP antagonists (e.g., Noggin), which potentially limit their therapeutic efficacy. It has been shown that BMP-6 is more resistant to Noggin inhibition and more potent in promoting osteoblast differentiation in vitro and inducing bone regeneration in vivo when compared with its closely related BMP-7 paralog. Article by Song K, Krause C, Shi S, Patterson M, Suto R, Grgurevic L, et al. (2010) "Identification of a key residue mediating bone morphogenetic protein (BMP)-6 resistance to Noggin inhibition allows for engineered BMPs with superior agonist activity", J Biol Chem. 285(16):12169-80 discloses a single amino acid in BMP-6 that modulates its susceptibility to Noggin inhibition, BMP-2 and BMP-7 variant and BMP resistance to Noggin inhibition and the presence of a lysine residue at position 60 of the mature domain. By using BMP-6/7 chimeras, it has been identified lysine 60 as a key residue conferring Noggin resistance within the BMP-6 protein. Introduction of a lysine residue at the corresponding positions of BMP-2 and BMP-7 allowed for molecular engineering of recombinant BMPs with increased resistance to Noggin antagonism. Mutation of BMP-2 at a Position Analogous to BMP-7 Glu$^{60}$ yields a BMP-2 variant/analogue with increased resistance to Noggin. Sequence alignment of BMP-2, 4, 5, 6, 7, and 9 revealed that only BMP-6 and BMP-9 have a lysine residue at the position corresponding to BMP-6 Lys$^{60}$. A proline to lysine mutation at this position in BMP-2 (BMP-2 P36K) yield a BMP-2 variant with increased Noggin resistance. Such a mutant BMP-2 was generated and tested for noggin resistance. This BMP-2 variant/analogue demonstrated a significant increase in Noggin resistance compared with its wild type counterpart. In conclusion, identification of $Lys^{60}$ in BMP-6 that confers noggin resistance allowing generating BMPs with superior agonistic activity.

U.S. Pat. No. 8,828,937, the disclosure of which is incorporated herein in its entirety, discloses bone morphogenetic protein 2 (BMP2) variants with reduced BMP antagonist sensitivity, more particularly it has been disclosed an isolated peptide comprising or consisting of an amino acid sequence with an amino acid identity of at least 90% compared to mature human BMP2 with SEQ ID No. 1, wherein said amino acid sequence comprises at least two amino acid substitutions characterized in that a first amino acid substitution occurs at a position corresponding to N59, S88, E94, V99, K101 and/or N102 of SEQ ID No. 1 and to uses thereof. Therefore, U.S. Pat. No. 8,828,937 B2 discloses substituted one amino acid at the Noggin binding region, this way it has become more active in inducing osteoblast differentiation. In examples of said patent, for functional characterization of the BMP2 variants, the chicken micromass culture system was used. A proof of concept was achieved using the chicken limb bud micromass system to analyze the functional abilities of the hBMP2 variants to induce cartilage production in a well-defined in vitro system. It has been found that the isolated peptide of the invention exhibits BMP2 activity while being essentially resistant to inhibition by the natural antagonist of BMP2, Noggin. The isolated peptide of the invention is characterized by reduced susceptibility to inhibition by Noggin, is more stable in an organism, preferably in a human, than naturally occurring BMP2 and/or elicits improved or altered biological activity. It has been found that substitution of at least two amino acids in the C-terminal region of BMP2 leads to an isolated peptide that is essentially resistant to inhibition by Noggin while the biological BMP2 activity is basically maintained.

U.S. Pat. No. 7,459,527, the disclosure of which is incorporated herein in its entirety, discloses BMP-7 variants with improved properties, wherein variant BMP-7 proteins have altered receptor binding affinity compared to wild-type BMP-7 (SEQ ID NO:5), the variant BMP-7 protein comprising one or more substitutions selected from the group consisting of: M23N, Q53G, Q53H and I86D. Table 21 of U.S. Pat. No. 7,459,527 shows EC50 of wild type human BMP-7 (R&D Systems) and BMP-7 variants 504, 526, and 565 for the BMP receptors BMPRIb, ActRIIa, and BMPRII and the BMP inhibitor noggin, as determined using AlphaScreen™ assays. Overall, these three variants have binding affinities that are similar to wild type. Potentially significant differences include, but are not limited to, decreased noggin affinity of v526 and increased noggin affinity of v565. Table 23 of summaries specific variant BMP-7 proteins created to have listed properties, and in addition to variant BMP-7 proteins of table 23, the variants listed in table 24 are also preferred variants.

U.S. Pat. No. 7,786,080, the disclosure of which is incorporated herein in its entirety, discloses a mutein of a bone morphogenetic protein, whereby the mutein comprises an amino acid substitution compared to the wildtype of the bone morphogenetic protein at the amino acid position corresponding to amino acid position 51 of human BMP-2 and for the treatment of a disease selected from the group consisting of fibrotic diseases, wound healing, hypervascularization, vascular diseases, fractures, and osteoporosis. Muteins according to U.S. Pat. No. 7,786,080 are capable of inhibiting the activity of modulator proteins such as those of the noggin family, the DAN family and the chordin protein family while not interacting with the receptor of the corresponding bone morphogenetic protein, which is the bone morphogenetic protein based on which the proteins are generated by substituting at least one amino acid, more particularly the BMP-2-like protein receptor.

U.S. Pat. Nos. 7,678,885, 6,593,109, 6,190,880 and 5,866,364 disclose recombinant heterodimeric BMP proteins useful in the field of treating bone defects, healing bone injury and in wound healing in general.

All the above BMP Variants/Analogues/Muteins and BMP Heterodimers are capable of inducing osteoblast differentiation and bone formation in rat implant assays, therefore these BMP variants and heterodimers are also osteogenic BMPs.

Osteogenic BMPs are defined by their ability to induce new bone in vivo when implanted with an appropriate carrier (example rat allogenic inactive bone collagen) in rat subcutaneous site. These active BMPs are dimers and have the hall mark of "TGF-beta Domain" composed of 7 cysteines and an inter disulfide bridge at the $4^{th}$ cysteine. In addition, they have at least 60 to 70% identity in their primary amino acid sequences to that of BM2 and BMP7. For example, highly osteogenic BMP4 and BMP6 have about 90% identity with BMP2 and BMP7 respectively. *Drosophila* proteins DPP (BMP2 human orthologue) and 60A (BMP7 human orthologue) are capable of inducing new bone in rat subcutaneous assays although *Drosophila* does not have bone (Sampath, T K et al, PNAS 90:6004-6008). On the other hand, other BMP-like proteins BMP3, BMP10, Activin and Inhibin and GDF-8/Myostatin are not capable of inducing new bone formation although they all have structurally a "TGF-beta domain" and contain an inter-disulfide bond at the 4-cysteine but have less than 40% identity in the primary amino acid sequences at the TGF-beta domain.

Collectively, what we claim here are all osteogenic BMP analogs/muteins/variants that have a common structural determinant, a close identity with BMP2 and BMP7 and are capable of inducing new bone formation in rat subcutaneous implant assays in vivo. These osteogenic analogs/muteins/variants are modified such that they lack affinity for naturally occurring BMP antagonist, Noggin or introducing amino acid at the N-terminal for proper processing and improve purification processes during the manufacturing or facilitate non-covalent affinity to specific substratum/scaffold.

A compression resistant matrix (CRM) present in a bone graft substitute described herein provides a biocompatible scaffold that both structurally supports and is progressively replaced by new bone growth stimulated by the osteogenic BMP component of the implanted autologous bone graft substitute. The compression resistant matrix useful in an autologous bone graft substitute described herein includes any of the compression resistant matrices that are currently employed in devices that have been approved for use in spinal fusion. A feature of compression resistant matrixes currently approved spinal fusion devices is that they are able to withstand the local forces that are applied to an implanted bone graft substitute by the local spinal musculature and vertebrae. The compression resistant matrix useful in the autologous bone graft substitute described herein includes a bone allograft (bone graft prepared from the bone of individuals other than the individual in need of treatment), a bioresorbable polymer or copolymer (e.g., polylactide, polyglycolide, etc.), synthetic calcium phosphate-carbonate composite such as hydroxyapatite (HA), tri-calcium phosphate (TCP), and combinations thereof. The compression resistant matrix useful in the autologous bone graft substitute composition described herein may also comprise an allograft, bone autograft and one or more calcium phosphate-carbonate composites and/or a bioresorbable polymer or copolymer, or combinations thereof. The compression resistant matrix granules for use in a bone graft substitute according to the invention may have a granule size of 74 μm to 8 mm, obtained using a sieve for such granule sizes.

The compression resistant matrix granule size for use in the autologous bone graft substitute described herein in a range 74 μm to 8 mm. A preferred compression resistant matrix geometry or shape include cylinders, slabs, sheets or mesh of specific dimensions depending on bone defect. The compression resistant matrix geometry or shape may have a shape of any one selected from cylinder, slab, sheet, mesh, or any other shape depending on a bone defect.

The geometrical shape of the compression resistant matrix is dictated by the medical indication. A compression resistant matrix particle and pore size in the autologous bone graft substitute composition with autologous blood coagulum (ABC) containing the osteogenic bone morphogenetic protein should preferably be compatible with the bone defect size. For example, in dental applications for filling the bone defect following tooth extraction the compression resistant matrix particle size should be in the range of 72 to 420 μm in an amount covering around 30 percent of the entire autologous bone graft substitute volume. For alveolar ridge augmentation in dental medicine which will allow insertion of more dental implants ceramics, the compression resistant matrix particle size may preferably be in the range of 0.5 to 4 mm. For bone defects of long bones, like non-unions of the tibia the defect of 1 to 3 cm in length can be filled with the compression resistant matrix having particle size of 3 to 8 mm. For long bone defects larger than 3 cm up to 10 cm in length the compression resistant matrix in a form of cylinders or slabs can be used in combination with the ABC and BMP6. The pore size of the compression resistant matrix particles should be large enough to allow blood vessel ingrowth which will further facilitate the formation of new bone in an orthotopic (between bone ends) or ectopic site (away from the skeleton).

As well, for bone defects of long bones, like non-unions of the tibia the defect of 1 to 3 cm in length can be filled with the compression resistant matrix consisting of synthetic calcium phosphate-carbonate (ceramics) or an allograft having particle size of 3 to 8 mm. For long bone defects larger than 3 cm up to 10 cm in length ceramics in a form of cylinders or slabs can be used in combination with ABC and BMP6. Preferably, cylinders or slabs will be made of 20% hydrohylapatite (HA) and 80% of tricalcium phosphate (TCP), lyophilized with the BMP, preferably BMP6, in a sterile lyophilization container connected to the blood collection unit which will allow a proper amount of blood to cover the cylinder or slab to be subsequently inserted in between large bone defects or between the transverse processes of spine vertebrae, preferably of the lumbar spine to induce ectopic bone formation and support the fusion of two adjacent lumbar vertebrae. A similar principle can be used to fuse the thoracic vertebrae. The pore size of ceramic particles should be large enough to allow blood vessel ingrowth which will further facilitate the formation of new bone in an orthotopic (between bone ends) or ectopic site (away from the skeleton). Ceramic cylinders shall have a central core backbone for unique uniting of individual ceramics particles along such a core element to provide more biomechanically stable structure for segmental bone defects and spine fusion of two or more vertebrae in patients with lumbar back pain due to degenerative disc disease.

Reverse thermosensitive polymers are Poloxamers which can be nonionic triblock copolymers composed of a central hydrophobic chain of polyoxypropylene (poly (propylene oxide)) flanked by two hydrophilic chains of polyoxyethylene (poly (ethylene oxide)). See generally U.S. Pat. No. 3,740,421. Poloxamers include the products Synperonics (Croda Inc., Edison N.J.), particularly poloxamer 407; Pluronic (BASF Corporation, Florham Park, N.J.); and Kolliphor (BASF Corporation, Tarrytown, N.Y.), a polyethoxylated castor oil and LeGoo® endovascular occlusion gel, which is comprised of a 20% (weight percent in saline) of purified poloxamer 407. Poloxamer 407/Pluronic F-127 copolymer (ethylene oxide and propylene oxide blocks) was purchased from BASF (Mount Olive, N.J.) used in the present study. The polymer was solubilized in Phosphate Buffered Saline (PBS) for a final polymer concentration of 20-40% weight/volume. At this concentration the polymer shows thermo-reversible properties, fluid state at room temperature and gel state at body temperature. For example, 20% gels were prepared by adding 20 g of Pluronic F-127 to 100 ml of cold PBS and left under agitation overnight at 4° C. for proper solubilization. The solution was next filtered with a 0.22 µm filter for sterilization. Poloxamers are a family of biocompatible, water-soluble polymers that possess reverse, thermo-sensitive properties (i.e., as temperature increases, viscosity increases). In particular, the poloxamer used is non-toxic, biocompatible, water-soluble and its viscosity decreases with increasing temperature in a range of use. At room temperature the composition is injectable, but viscous. Upon heating to body temperature, it undergoes a temperature-induced phase change with no effective alteration in chemical composition—no curing—to form a polymeric plug or slab. At room temperature or below, the composition viscosity is suitable for injection by a syringe, e.g., the ABGS exhibits the syringe delivered from a 5-15 cc syringe with a needle size of 20 G-1.5". The autologous bone graft substitute composition can be a malleable putty. The composition has between 50 and 80% liquid by weight. The average particle size of the compression resistant matrix is in a range between 70 and 425 µm, or 1-5 mm as determined by particle sieve. The composition components are dissolved/suspended in autologous blood. The autologous bone graft substitute composition may include a radio-contrast agent.

The autologous bone graft substitute composition (Autologous Blood Coagulum/BMP-6/CRM or BMP6/CRM/Autologous Blood Coagulum or BMP6/CRM/Autologous or Allogenic Platelet Rich Plasma or Autologous Blood/BMP-6/CRM/Reverse Phase Thermosensitive Polymer) with or without autologous bone marrow aspirate, or with or without MSCs expanded from autologous bone marrow, or autologous adipose or autologous periosteum, or allogenic umbilical cord described herein provides a permissive microenvironment to induce robust new bone formation by overcoming an undesirable response that may occur using bone allograft or synthetic ceramics of high mineral (calcium phosphate or calcium carbonate or calcium sulfate) animal-derived collagen or collagen-compression resistant matrix composites scaffold that have been approved for use with BMP in humans. In particular, implantation of the ABGS described herein does not trigger rapid and robust inflammatory and immunological response ("inflammatory storm") and foreign-body reactions (formation of multinucleated giant cells) that may occur at the site (specifically at ectopic sites) of implantation for currently approved bone graft substitutes. The "inflammatory storm" comprises abundant infiltrating, inflammatory, cytokine-producing cells (e.g., monocytes, polymorphonuclear leukocytes, macrophages, myofibroblasts, fibrocytes), immunological responses or foreign body reaction (formation of multinucleated giant cells). To overcome an inflammatory storm elicited by CRM/CRM-collagen composites and an immune and fibrogenic response triggered by animal derived collagen, high concentrations of BMP are employed in the current device that posed unwanted safety issues ectopic bone formation away from the implant site. During the "inflammatory storm", the population of such inflammatory/immunological (non-progenitor) cells is significantly higher than the population of mesenchymal stem cells (osteoprogenitor cells) that respond to form new bone when brought into contact with an osteogenic BMP. The primary trigger for the "inflammatory storm" of non-progenitor cells appears due to be the presence of a compression resistant matrix component of currently used as scaffold in BMP bone graft substitutes.

According to this view, at ectopic sites multinucleated foreign-body giant cells are recruited by a compression resistant matrix of currently approved bone graft substitutes in numbers that are sufficiently large to interfere with or otherwise inhibit the ability of osteoprogenitor cells, which are either absent or present in significantly smaller numbers, to respond to osteogenic BMP and produce sufficient new bone growth required to treat bone defect. In contrast, the autologous bone graft substitute composition (ABGS) described herein containing the similar or comparable compression resistant matrix component found in currently approved bone graft substitutes does not elicit an inflammatory storm of cells when implanted into or otherwise applied to a site in need of new bone growth. Instead, the compression resistant matrix in the autologous bone graft substitute composition described herein provides an initial mineral-like structure (within the coagulum gel) that is absorbed and replaced in an orderly progression with new bone growth in the amount and kind required to achieve the desired treatment, such as repair of a bone defect or fusion of adjacent bone segments. This discovery of unexpected biology indicates that an autologous blood component of the autologous bone graft substitute composition described herein is responsible for suppressing or interrupting the triggering of an "inflammatory storm" by the compression resistant matrix component and suppression of foreign-body reaction by inhibiting the formation of multinucleated giant cells that would otherwise occur in the absence of the coagulum.

The generation of a robust "inflammatory storm" may likely be the reason why currently approved non-autologous blood coagulum bone graft substitutes, such as those approved for spinal fusion, employ relatively large amounts of osteogenic BMP (for example, more than 12-40 mg per level for spine indication) in order to promote new bone growth. The fact that use of such relatively large amounts of BMP can result in bone formation at sites distal from the local implant site draws concern from regulatory agencies for potential untoward side effects. In contrast, the autologous bone graft substitute composition described herein comprises the autologous blood coagulum gel containing the osteogenic bone morphogenetic protein and advantageously employs significantly lower amounts of BMP to promote new bone growth than the levels found in currently approved bone graft substitute devices. Typically, an amount of BMP present in the autologous bone graft substitute composition described herein will be five- to twenty-fold lower than the amount of BMP used in currently approved bone graft substitute devices. By way of non-limiting examples, the autologous bone graft substitute composition of the present invention may comprise 0.002 mg to 1 mg of BMP per ml of Autologous Blood. Preferably, the BMP is BMP-6, which does not bind to Noggin, a naturally BMP antagonist abundant in bone and spans across most of Type I and II BMP receptors.

Optionally, the autologous bone graft substitute composition described herein may further comprise an allogeneic demineralized bone matrix (or "demineralized bone matrix"), which is a gel composition derived from allogenic bone and which contains residual factors that can augment new bone growth. Owing to its gel state, the autologous bone graft substitute composition described herein may be administered to a site in need of new bone growth by implantation (placing the bone graft substitute in or at a site) or by injection (for example, using a syringe). Unless otherwise indicated, the terms "implanted" and "implantation" are also understood to encompass the application of a bone graft substitute described herein to a defect site by injection.

Optionally, the autologous bone graft substitute composition can be augmented with mesenchymal stem cells (osteoprogenitors) obtained or expanded from autologous or allogenic bone marrow or adipose tissue. In some incidents, the autologous bone graft substitute composition may be enriched with tissue fragments from local bone, muscle and fascia. This level of cell/tissue augmented ABGS is advantageous where the responding cells for BMP are minimized at the given site (e.g., distal tibia) and in rare genetic disorders (Hypophosphatasia, Neurofibromatosis Type I and Osteogenesis Imperfecta). In addition, the autologous bone graft substitute composition comprising reverse phase thermosensitive bioresorbable polymer will provide biocompatibility and handling property as injectable at room temperature and attain solid-gel like structure at the body temperature. The presence of autologous blood coagulum provides protection against the inflammatory storm elicited by the compression resistant matrix added to the autologous bone graft substitute composition as well as biocompatibility and it provides an "Autograft" tissue equivalent.

In some setting the autologous bone graft substitute composition may be prepared with an allogenic or autologous platelet-rich plasma (PRP) substituting autologous blood (AB). Owing to its various properties, the autologous bone graft substitute composition described herein may be advantageously used in place of "Autograft" in one or more of a variety of treatments that employ autograft harvested from an individual in need of treatment. Such treatments include, but are not limited to, spinal fusion, repair of skeletal bone fractures, high tibial osteotomy, dental repairs, periodontal repairs, pseudo-arthrosis, pseudo-fractures associated with rare skeletal disorders and maxillofacial augmentations. Particularly, the autologous bone graft substitute composition described herein for use in treating any of a variety of bone defects. Such bone defects may include, but are not limited to, diaphyseal fractures, distal radius fractures, tibial non-union fractures, osteoporotic fractures (such as vertebral compression fracture and atypical diaphyseal fracture), bone cysts (where bone must be generated to fill a void), bone tumors (where new bone must replace bone that has been lost by cancer or that has been removed by surgery), oral defects, periodontal defects and various maxillofacial anomalies. Use of the autologous bone graft substitute described herein advantageously extends the use of such procedures beyond the limitation of the amount of autograft that can be safely harvested from an individual in need of treatment thereof. Only pharmaceutically acceptable components are used in preparing an implantable composition of the invention.

The term "allograft" is a term of the art and refers to bone from a cadaver that has been prepared aseptically for implantation in a patient. Allograft may be commercially obtained from tissue bone banks.

The terms "disorder" and "disease" are synonymous and refer to any pathological condition, irrespective of cause or etiological agent. A "defect" in a bone or other tissue refers to a site of abnormal or deficient tissue growth. A "disease" or "disorder" may be characterized by one or more "defects" in one or more tissues. As used herein, the terms "treatment" and "treating" refer to any regimen that alleviates one or more symptoms or manifestations of a disease or disorder, that inhibits, arrests or reverses (causes regression) of a disease or disorder, or that prevents onsets of a disease or disorder. The term "treatment" includes prophylaxis (prevention) of one or more symptoms or manifestations of a disease, including ameliorating or inhibiting the extent of a symptom or manifestation, including pain, that would otherwise characterize the disease in the absence of the treatment.

A "therapeutically effective amount" is an amount of a compound (for example, osteogenic BMP protein) that promotes bone growth at a desired location and in an amount that is desired for achieving a desired endpoint, such as, but not limited to, a stabilized spinal fusion of adjacent vertebrae, filling of a bone defect with new bone, bridging of distal ends of a bone defect, or correction or rebuilding of an oral or maxillofacial injury or anomaly. Such an endpoint can be determined by following new bone growth through standard methodologies, such as X-rays or visual inspection by an attending surgeon or other skilled practitioner.

A composition or method described herein as "comprising" one or more named elements or steps is open-ended, meaning that the named elements or steps are essential, but other elements or steps may be added within the scope of the composition or method. To avoid prolixity, it is also understood that any composition or method described herein as "comprising" (or "which comprises").

Description of Ceramics Release Study

Coagulum formed in the presence of rhBMP6 without a calcium phosphate-carbonate composite, hereafter Ceramics, was used for comparison. It was found that the ABGS containing rhBMP6/ABC released initially larger amounts which steadily decreased to very low levels after 10 days.

In contrast, with the autologous bone graft substitute composition containing rhBMP6/ABC/Ceramics there was still a substantial release seen after 10 days. Therefore, the ceramic has a longer lasting action.

The particle sizes of tri-calcium phosphate (TCP)-hydroxyapatite (HA) TCP-HA have some effect but all sizes bind BMP.

With the BMP preloaded ceramics without the autologous blood coagulum (ABC) addition, it was observed that there was no early release until after at least 6 days. Release is than increasing by 10 days and likely beyond.

However, when preloaded ceramic was mixed with the autologous blood coagulum there was some release, followed by an interval of less release. It resulted in the combination of release curves of just preloaded ceramic and of the autologous blood coagulum without ceramics. Initial release was presumably due to the addition of the autologous blood coagulum containing some plasmin protease from the clotting reaction. This would have modified some of the BMP in a way to remove the binding ability to ceramic.

The likely modification of BMP6 to allow release is the removal of the arginine-rich N-terminal loop containing also a heparin binding site. This initial release was not seen without addition of the autologous blood coagulum. Thus, the release due to the autologous blood coagulum addition would be due to proteins and proteases present in the coagulum interacting with the BMP causing the release. However, not all BMP would be immediately converted in this way, which accounts for BMP that remained with ceramic. Eventually, this will also be released once residual protease has had more time to act.

This is claimed as an improvement: more delayed and longer lasting release.

Also, the binding to the compression resistant matrix is very tight (released by 100 mM phosphate, but will not occur in just saline/medium). It is concluded that the ceramic binds BMP very tightly via the ionic interactions such that there is almost no release during the first few days. This favors the tight localization of new bone formation.

And this tight binding is preventing exuberant release and spreading of bone formation.

Figure 16:
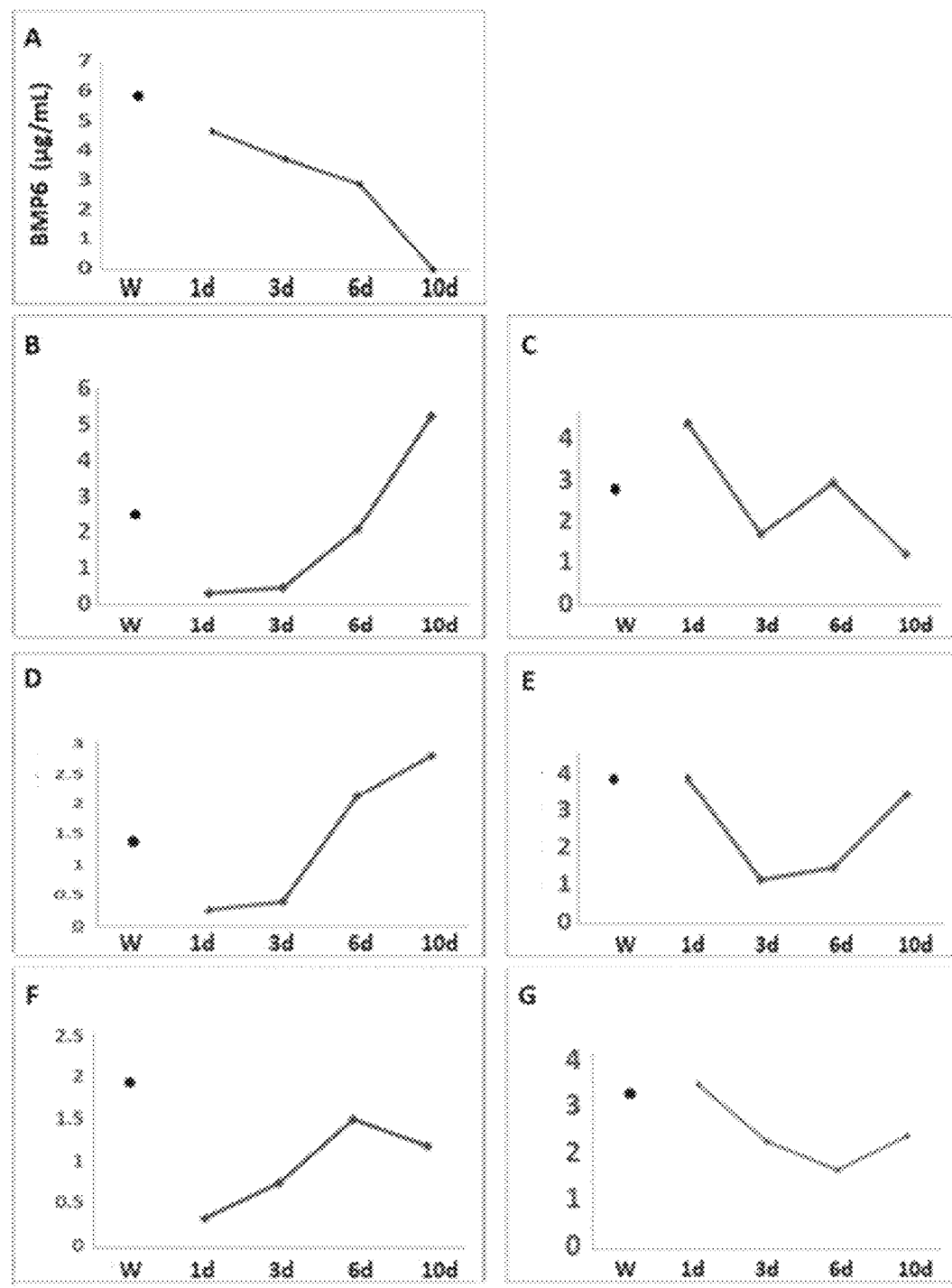
FIG. 16 shows release of BMP from BMP-loaded ceramics and the effect of ABC addition on the release, during 3-day intervals, as measured by Elisa assay.
Figure 17:
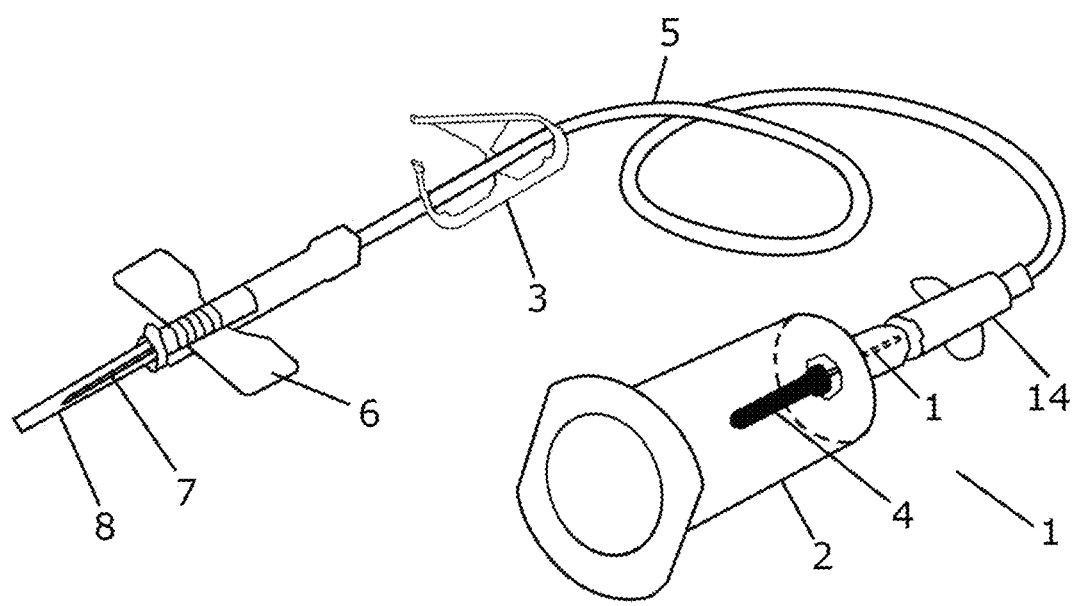
FIG. 17 illustrates a schematic perspective view of a kit for preparing an ABGS for inducing new bone formation.
Figure 18:
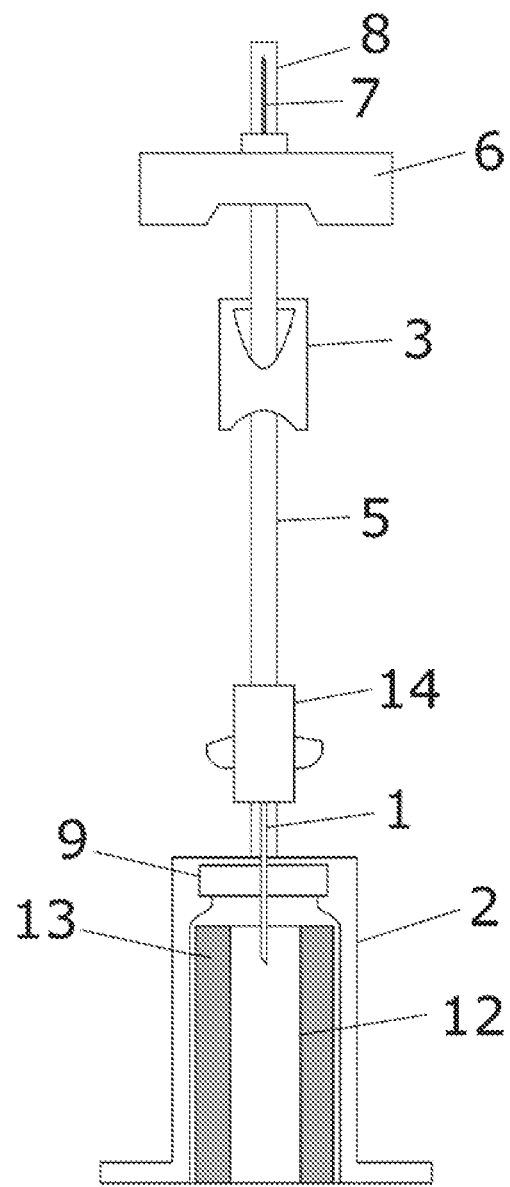
FIG. 18 illustrates a schematic side view of a kit for preparing an ABGS for inducing new bone formation.

FIG. 16 illustrates BMP6 release results obtained from Ceramics with particles of different sizes. Ceramics is made by CaP, Biomaterials LLC. Ceramic of different sizes were placed into Eppendorf tubes, 140 mg into each tube. Then 200 µl of a solution containing 50 µg BMP6 drug substance in 20 mM glycine buffer pH 6 were added to the dry ceramic, where it was immediately absorbed. It was and allowed to interact for 15 minutes at room temperature.

This volume of 200 µl liquid was rapidly absorbed by the finer grade ceramic particles, whereas the larger grain had notably less capacity for adsorbing of the liquid.

The tubes with wetted ceramic were put into a minus −80 Centigrade freezer for 30 minutes and then transferred to a GEA SL-2 lyophilizer with the shelf temperature at −18° C. and then freeze dried for 24 hours. By this time, materials were completely dry and the vacuum remained stable at 20 microbar remaining pressure.

This dry ceramic, preloaded with BMP6, was then evaluated in a BMP release study over 10 days using a BMP6 Elisa assay from RnD systems. In parallel, tubes with preloaded lyophilized matrix received blood, which was allowed to coagulate after gentle mixing with the ceramic particles. The serum was removed from the autologous blood coagulum and these samples were also evaluated for release of BMP over 10 days.

Also, for comparison of the release kinetics, a sample of "ABC+BMP6" i.e., 50 µg BMP and 200 µl of blood was set up to form a coagulum, from which the serum was also removed.

For measuring the release of BMP6 the described coagulum samples and BMP6-matrix samples without the autologous blood coagulum respectively were first rinsed once with 1 ml of tissue culture medium whereupon 1 ml fresh medium was added for 1 day. This 1 ml was collected for Elisa assay and replaced by fresh medium after 3 days. It was again collected and replaced on day 6 and again collected on day 10 for Elisa assay.

Results of the studies are shown in FIG. 16, panels A to G, illustrating a release of rhBMP6 from ABGS, in vitro, during the first 10 days, as measured by Elisa assay. Panel A shows release from ABC+BMP6 coagulum, panel B, D and E show release from ceramics of different grain size ranges, i.e. 1 to 4 mm (B), 0.5 to 2.5 mm (D), 0.5 to 1.5 mm (E). Panels C, F and G show corresponding release from ceramics with coagulum, again comparing coarse, medium and fine grain.

Seven different BMP carriers, 140 mg each, containing 50 ng of rhBMP6, are compared for the release of BMP6 over 10 days. The Y-axis shows micrograms of BMP6 released into 1 ml of serum-free cell culture medium used to soak the carriers, with medium being replaced every few days (X-axis) and assayed by Elisa.

Panel A: 0.14 ml ABC+BMP6, no ceramic. Panels B, D, F show ceramic with BMP6 but without the ABC. Panels C, E, and G show ceramic with BMP6 and addition of the ABC. Panel B: ceramic of large particles size (1000-4000 µm); Panel C: same as B, but with the ABC added; Panel D: ceramic of medium sized particles (500-2500 µm); E: same as D, but with the ABC added; F: ceramic of small sized particles (500-1500 µm) and G: same as F, but with the ABC added. The first data point (W) in each panel represents BMP6 obtained from an initial wash (1 ml) of the carriers.

The conclusions were that BMP6 preloaded ceramic without the ABC showed a delayed BMP release whereas the ceramic plus the ABC show a biphasic release, initially similar to ABC+BMP6 but then lasting much longer than ABC+BMP6. Thus, the combination gives a more even and extended release.

Example 1: Preparation of Autologous Bone Graft Substitute Composition (ABGS)

Autologous Bone Graft Substitute (ABGS) is composed of the following:
1) Recombinant human BMP6 (rhBMP6);
2) Autologous blood; and
3) Calcium or Strontium or Magnesium salt (at low mM) being in a form of aqueous solution, or nanoparticles or microspheres or
1) Recombinant human BMP6 (rhBMP6);
2) Autologous blood;
3) Calcium or Strontium or Magnesium salt (at low mM) being in a form of aqueous solution or nanoparticles or microspheres; and
4) Compression Resistance Matrix (CRM)

Methods of Preparation

Method #1: Comparative bone graft without Compression Resistance Matrix (CRM) component Comparative bone graft is composed of the following:
1) Recombinant human BMP6 (rhBMP6),
2) Autologous blood, and
3) Calcium or Strontium or Magnesium salt (at low mM) being in a form of aqueous solution, or nanoparticles, or microspheres.

Autologous Blood is drawn peripherally from patient or collected locally (local blood). For preclinical studies autologous blood can be collected from marginal ear veins as in case of rabbits or from jugular veins as in case of sheep respectively into tubes without any anticoagulant substance supplemented with 15 to of 50 mM/ml blood Calcium or Strontium or Magnesium salt (e.g., chloride, carbonate, bicarbonate, gluconate) either in solution or nanoparticles or microspheres solution in a specific volume of autologous blood. Lyophilized rhBMP6 was dissolved in a small volume (10-500 µL) of water for injection and then mixed with autologous blood (0.2 to 10 ml). Immediately after mixing rhBMP6 with autologous blood (within a minute) and then left in room temperature to coagulate with defined structure and rheological properties as determined by stiffness, elasticity and strain.

Method #2: Comparative bone graft with Compression Resistance Matrix (CRM) component Autologous Bone Graft Substitute (ABGS) is composed of the following:
1) Recombinant human BMP6 (rhBMP6),
2) Autologous blood,
3) Calcium or Strontium or Magnesium salt (at low mM) being in a form of aqueous solution, or nanoparticles, or microspheres, and
4) Compression Resistance Matrix (CRM).

Autologous blood is drawn peripherally from patient or collected locally (local blood). For preclinical studies autologous blood can be collected from marginal ear veins as in case of rabbits or from jugular veins as in case of sheep respectively into tubes without any anticoagulant substance supplemented with 0.1 ml of 50 mM $CaCl_2$) solution in a specific volume depending on indication. Lyophilized rhBMP6 was dissolved in a small volume (10-200 µL) of water for injection and then mixed with autologous blood. Immediately after mixing rhBMP6 with autologous blood, the compression resistant matrix in particulate form was added and then left at room temperature to coagulate with defined structure and rheological properties as determined by stiffness, elasticity and strain (ref).

Method #3: Autologous Bone Graft Substitute Composition with the Compression Resistance Matrix (CRM) component The compression resistant matrix (in particulate or cylinder or slab or mesh form) is soaked or sufficiently wet in rhBMP6 dissolved in a small volume (10-1000 µL) of water for injection and subjected to lyophilizing under vacuum. To the lyophilized compression resistant matrix-rhBMP6 composite, autologous blood was added sufficiently without any anticoagulant substance supplemented with 0.1 ml of 50 mM $CaCl_2$) and then left in room temperature to coagulate with defined structure and rheological properties as determined by stiffness, elasticity and strain.

Method #4 Autologous Bone Graft Substitute Composition with the Compression Resistance Matrix (CRM) component A method of preparation an autologous bone graft substitute composition for inducing new bone formation, the preparation method comprising the steps of:
1) mixing:
   a. autologous blood;
   b. an osteogenic bone morphogenetic protein selected from BMP-6, BMP-2, BMP-7, BMP-4, BMP-5, BMP-8, BMP-9, BMP-12, and BMP-13, analogs thereof or heterodimers thereof, and combinations thereof, in a range of from 0.002 mg per ml to 1 mg per ml of autologous blood, preferably the osteogenic bone morphogenetic protein is a recombinant human osteogenic bone morphogenetic protein BMP-6 (rhBMP-6); and
   c. a compression resistant matrix 12 (CRM) selected from the group consisting of a bone allograft, bone autograft, hydroxyapatite, tri-calcium phosphate, and combinations thereof;
2) incubating components of step (1) for a period sufficient to form a coagulum gel comprising a fibrin-meshwork reinforced with the compression resistant matrix, the coagulum gel containing the osteogenic bone morphogenetic protein, whereby the coagulum gel and the compression resistant matrix provide a sustained release of the osteogenic bone morphogenetic protein;
3) mixing the osteogenic bone morphogenetic protein in aqueous solution with the compression resistant matrix 12 in a sterile lyophilization container 10 wherein a volume of rhBMP-6 aqueous solution added to the compression resistant matrix is optimized for complete wetting of the compression resistant matrix;
4) lyophilization of the osteogenic bone morphogenetic protein and the compression resistant matrix 12;
5) adding autologous blood; and
6) incubating the lyophilized osteogenic bone morphogenic protein and the compression resistant matrix composite 12 in autologous blood for a period sufficient to form a biomechanically stable blood clot 13 around the lyophilized osteogenic bone morphogenetic protein and the compression resistant matrix 12.

First, the osteogenic bone morphogenetic protein in aqueous solution is mixed with the compression resistant matrix 12 in the sterile lyophilization container 10 that may be sealed under vacuum by rubber stopper 9 and secured by crimping with an aluminum cap or an additional screw cap. The volume of the osteogenic bone morphogenetic protein aqueous solution which is added to selected the compression resistant matrix 12 is optimized for complete wetting of the compression resistant matrix. The volume of the osteogenic bone morphogenetic protein aqueous solution for wetting may just be sufficient or equal to the volume of the compression resistant matrix 12 depending on the geometry of the compression resistant matrix (porous versus non-porous; particulate versus cylinder). If the aqueous volume exceeds beyond the wetting volume it may result in some dry osteogenic bone morphogenetic protein along the surface of the lyophilization container 10. The freeze drying is performed until complete dryness. BMP/CRM, upon lyophilizing, the lyophilization container 10 is closed under vacuum (rubber stoppers being pushed all the way down), preferably be stored refrigerated at −20° C. or 4° C.

Figure 19:
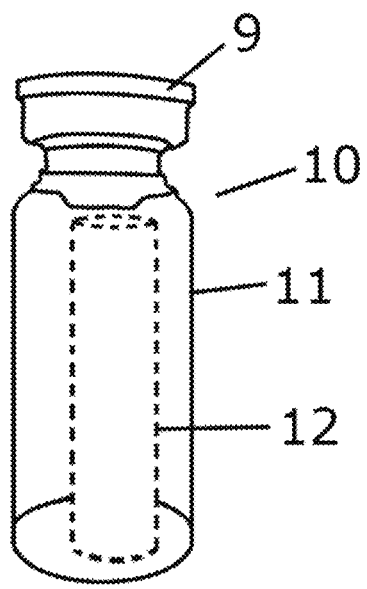
FIG. 19 illustrates a lyophilization container comprising a lyophilized content (BMP+CRM)
Figure 20:
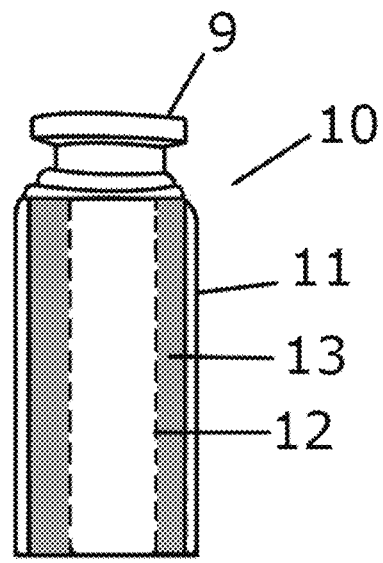
FIG. 20 illustrates a lyophilization container comprising a mechanically stable blood clot formed around the lyophilized rhBMP-6 and the compression resistant matrix.

Second, the autologous blood is collected from the patient's vein, like a typical phlebotomy into a vacutainer that contains the freeze-dried BMP-CRM (as illustrated in the FIG. 19). A longer line of a sterile tubing 5 with a clamp 3 may likely facilitate the processing blood to the lyophilization container 10. The lyophilization container 10 with lyophilized contents (BMP+CRM) 12 is placed into a lyophilization container holder 2 to insure safe puncture of the rubber stopper 9 of the lyophilization container 10 insuring sterile insertion of the needle 1 through the septum. The needle 1 may be protected by another rubber sleeve 4 also to further ensure sterility. The lyophilization container holder 2 is connected by the sterile tubing 5 to a needle 7 for phlebotomy, and initially is clamped off by a small plastic hose clamp.

FIGS. 17 to 20 illustrate a kit for preparing an ABGS of implant for inducing new bone formation. For example, in the kit for preparing the ABGS of implant for inducing new bone formation comprises: a butterfly needle set 6, 7, 8 for an autologous blood collection;

A sterile lyophilization container holder 2 comprising a needle 1 protected with a rubber sleeve 9;

a sterile tubing 5 connecting the butterfly needle set 6, 7, 8 and the sterile lyophilization container holder 2;

a tubing clamp 3 for releasing vacuum or to stop flow of blood;

a sterile lyophilization container 10 with a rubber stopper 9 containing a lyophilized osteogenic bone morphogenetic protein mixed with the compression resistant matrix 12;

The compression resistant matrix 12 is selected from the group consisting of a bone allograft, bone autograft, hydroxyapatite, tri-calcium phosphate, and combinations thereof.

The sterile lyophilization container 10 may have any shape suitable for receiving the compression resistant matrix 12, where the compression resistant matrix 12 may have the shape of any one selected from cylinder, slab, sheet, mesh, or any other shape depending on a bone defect.

Example #2 Methods of CRM Evaluation (Rat Subcutaneous Implants)

The following CRMs are used in the preparation of the ABGS.
Allograft
Autograft
TCP
HA
TCP/HA conjugates
Calcium sulfate
Calcium-phosphate-carbonate composite (ceramics)
Bioresorbable polymers
Bioresorbable Hydrogels The following geometry of a given CRM used in the fabrication of the autologous bone graft substitute composition:

Particle size is in a range from 74 µm to 8 mm; and
CRM may be in a form of particles or may have a shape of any one selected from cylinder, slab, sheet, mesh, or any other shape depending on a bone defect.

The compression resistant matrixes with varying physical properties are formulated with rhBMP6 using either method #2 or #3 as described in Example #1. The cellular response and bone-inducing activity of the autologous bone graft substitute composition, the autologous bone graft substitute composition was assessed by implanting at subcutaneous sites or by injecting percutaneously into abdominal fascia or skeletal muscle pouches of rodents. At 1, 3, 7 and 12-35 days after implantation/injections, the implants were harvested, and assayed for cellular response and bone forming activity by histology as described (Sampath, T K. and Reddi, A H. PNAS 1981).

The autologous bone graft substitute composition was prepared from 0.25-0.5 ml of rat full blood which was mixed with an appropriate amount of BMP (example 2 to 200 µg recombinant BMP-6 per ml blood) and then added the compression resistant matrix (Allograft, Allogenic bone from donor (ALLO) or Tri-calcium Phosphate (TCP) or TCP and Hydroxyapatite (HA) composite) left for 60 minutes to coagulate in a 1 ml syringe. After removing the serum, the ABC with a volume of approximately 125-300 µl was implanted. Most of rhBMP-6 (>95%) was bound to ABC. The osteogenic response of each rhBMP-6 doses was tested in 4 to 8 implants in two to four rats each. A small pocket was created under the skin in the abdominal under arm-pit regions to implant the ABGS prepared with Autologous Blood/rhBMP-6/CRM. The ABGS (approx. 125-300 µl without serum) was implanted and sealed with a single suture to the fascia and 3 stitches for the skin. To analyze ectopic bone formation, animals were scanned using a 1076 micro CT device (SkyScan, Belgium) at 28 days after implantation. Ectopic bone formation was observed in all groups of animals and was quantified by micro CT analysis. Quantification of the ectopic bone showed a dose dependence. The cellular response and bone formation are assessed by histology at various time intervals following creeping substitution more evident at higher magnification.

Figure 2A:
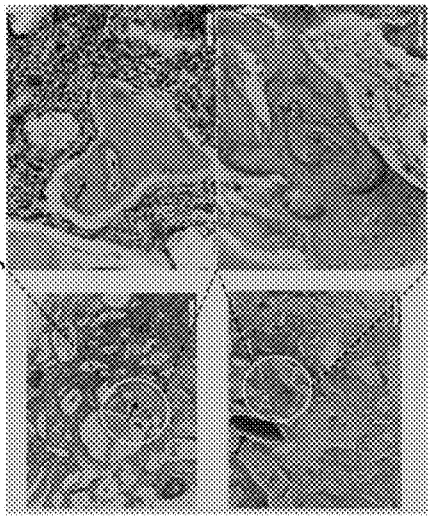
FIGS. 2A and 2B show histological observations of the implants of (Autologous Blood Coagulum containing Allograft/Allogenic bone from donor) ALLO plus ABC implants and ABC+ALLO+rhBMP6 implants on day 7 and day 35.
Figure 2B:
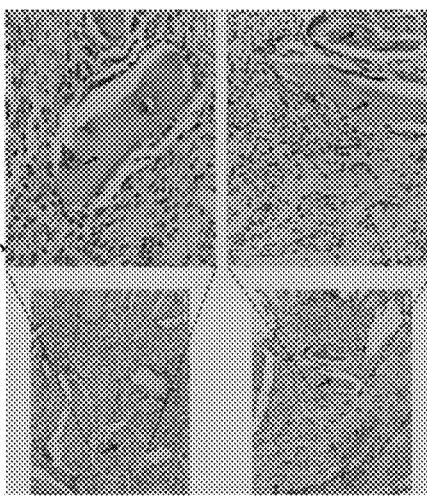
Figure 2D:
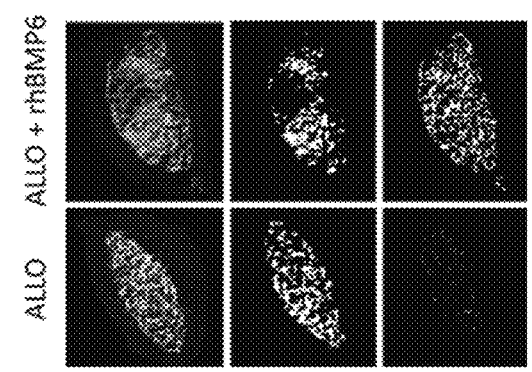
FIGS. 2C and 2D show micro-CT analysis of ABC/ALLO and ABGS (ABC/ALLO/rhBMP6) from Day-7 and Day-35 implants.
Figure 2E:
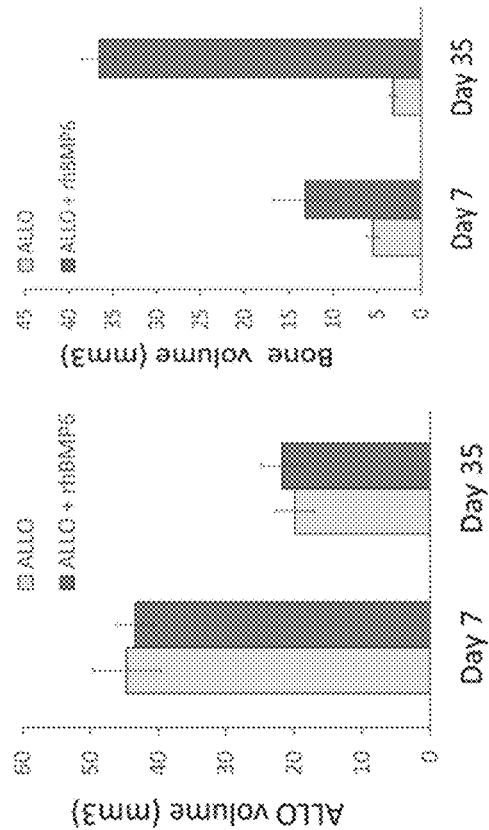
FIGS. 2E and 2F are graphs illustrating the Allograft Volume and Bone Volume quantified using micro-CT analysis for ABC plus ALLO and ABC+ALLO+rhBMP6 on day 7 and day 35 in the rat subcutaneous implants.
Figure 2F:
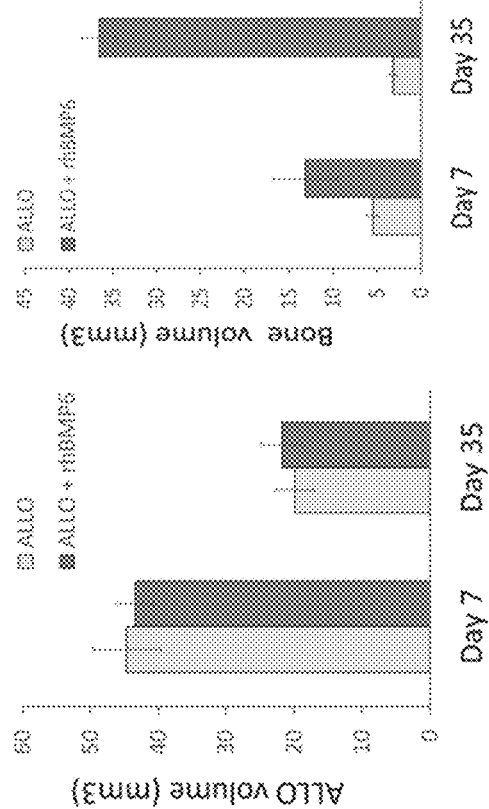
Figure 2C:
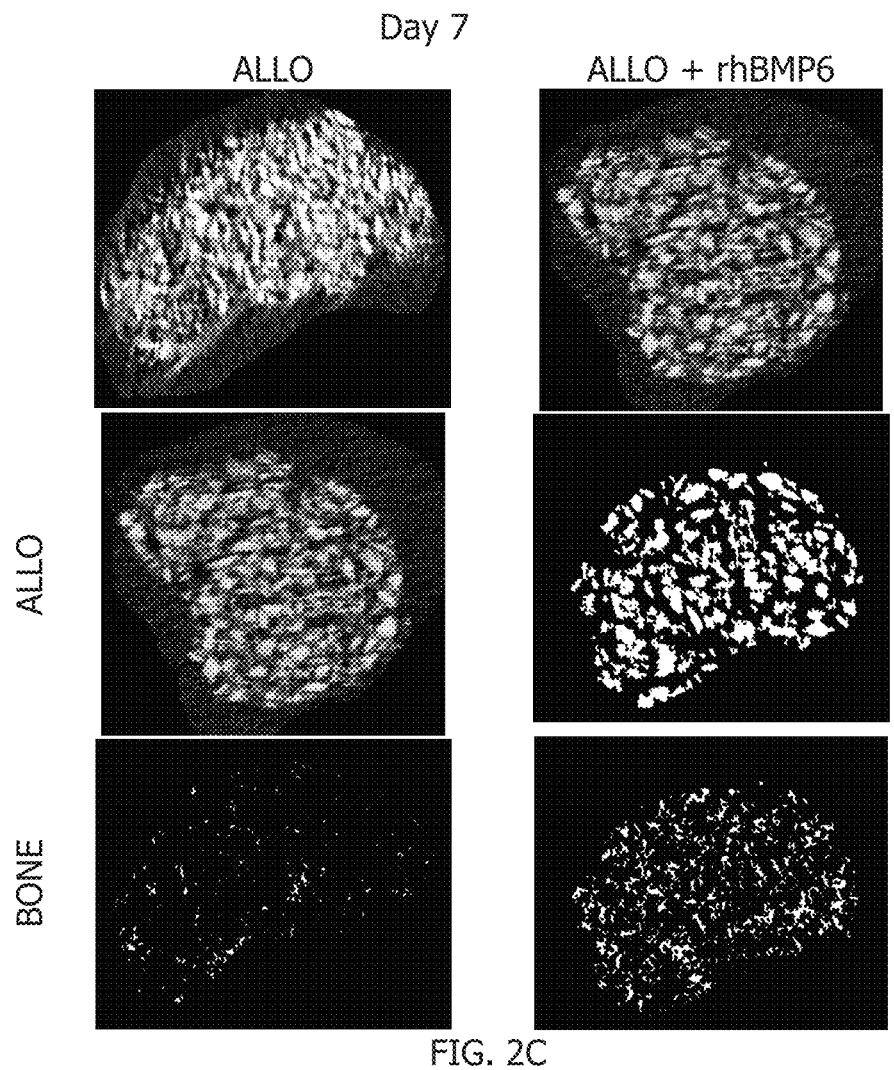

Subcutaneous implantation of autologous blood coagulum (ABC) alone recruits migrating mesenchymal stem cells (osteoprogenitors) within day 1-3 and forms a tissue capsules which then undergo a dissolution by day 7-9, whereas the ABC containing rhBMP6 implants induced the differentiation of MSCs into endochondral bone by day 7, newly formed bone then undergoes remodeling by day 21-35 filled with ossicles containing functional bone marrow elements. Histological observation of the implants of ALLO plus ABC implants and ABC+ALLO+rhBMP6 implants on day 7 and day 35 are shown in FIGS. 2A and 2B. There are already signs of endochondral bone formation in rhBMP6 containing implants by day 7. In day 35 implants, a robust bone formation has occurred in ABC/ALLO/rhBMP6 implants in between and in apposition with ALLO particles that underwent a typical bone remodeling via creeping substitution (allograft resorption replaced with newly formed bone). Micro-CT analysis of ABC/ALLO and ABGS (ABC/ALLO/rhBMP6) from Day-7 and Day-35 implants, visualized as overall micro-CT, specifically ALLO particles and the newly formed remodeled bone without ALLO particles are shown in FIGS. 2C and 2D. ALLO and ABC implants by alone did not induce bone and formed the fibrous-tissue like capsules around the implants, and then resorbed by day 18-21. In ABC/ALLO implants that contained rhBMP6, osteogenesis was observed with a gradual resolution of allograft. FIGS. 2E and 2F represents the Allograft Volume and Bone Volume quantified using micro-CT analysis for ABC plus ALLO and ABC+ALLO+rhBMP6 on day 7 and day 35 in the rat subcutaneous implants.

Example #3: Unexpected Biological Activity of Autologous Blood

Rat Subcutaneous Implant assay was used to assess the role of autologous blood in overcoming the inflammatory and foreign-body reaction in the autologous bone graft substitute composition (ABGS) that contained the compression resistant matrix (Allograft and/or Synthetic Ceramics (Tri-calcium phosphate or Hydroxyapatite or combination thereof) has been used in generating the ABGS using the method #2 or #3. rhBMP6 osteogenic activity was tested at different doses. ABC/rhBMP6/ALLO implants, rat allograft particles of 74-420 µm were added at 0.1 to 0.5 g/ml autologous blood.

To identify inflammation and foreign body rejection in allograft containing implants, implants are harvested from day 1, 3 and 7 and sections were stained by H&E/or Toluidine blue staining and acid phosphatase detection by histochemistry on paraffin embedded sections. Groups examined included allograft only, allograft mixed with the autologous blood coagulum (ABC) or allograft with the ABC and 25 µg rhBMP6 per ml of autologous blood, the implants were removed from animals on days 7 or 14 and subjected to analysis of foreign body giant cells.

Figure 3A:
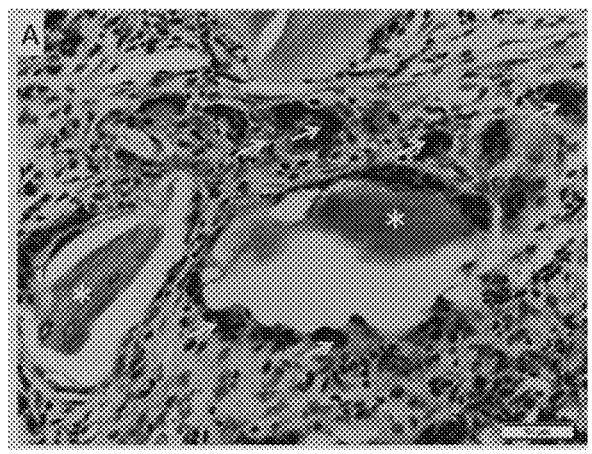
FIG. 3A shows photomicrographs of histology from Autologous Blood Coagulum containing Allograft (ALLO) implanted at rat subcutaneous sites.
Figure 3B:
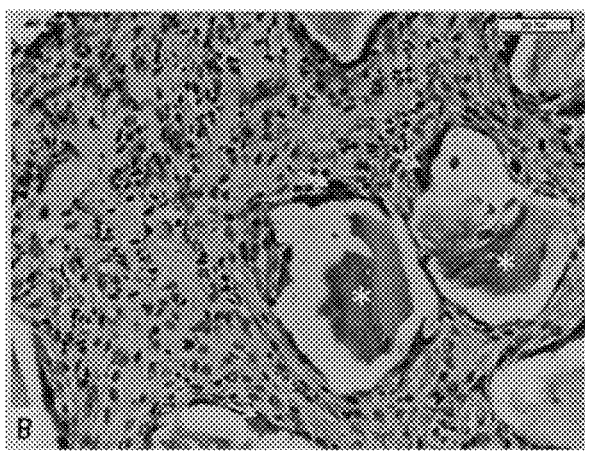
FIG. 3B shows photomicrographs of histology when ALLO particles were formulated within ABC implanted at rat subcutaneous sites.
Figure 3C:
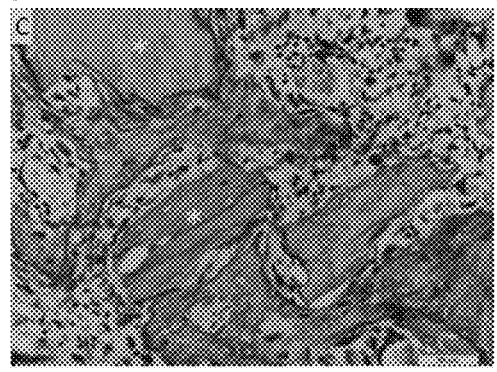
FIG. 3C shows photomicrographs of histology when implants containing ABC+ALLO+rhBMP6, ALLO particles were formulated and implanted at rat subcutaneous sites.
Figure 3D:
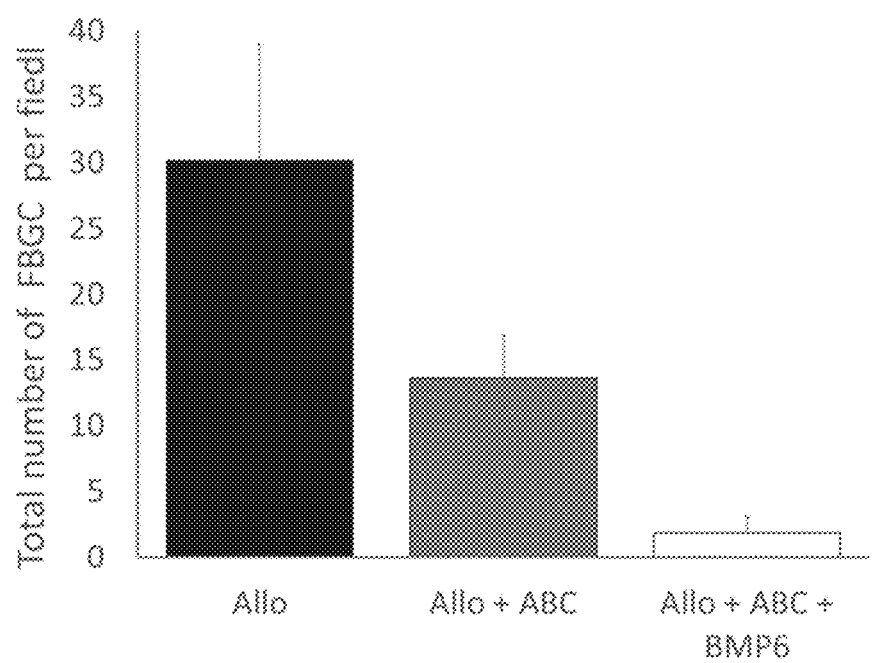
FIG. 3D shows a graph illustrating the average number of multinucleated FBGCs counted morphometrically from three representative histology sections from ALLO, ALLO+ABC and ALLO+ABC+rhBMP6 implants.
Figure 3E:
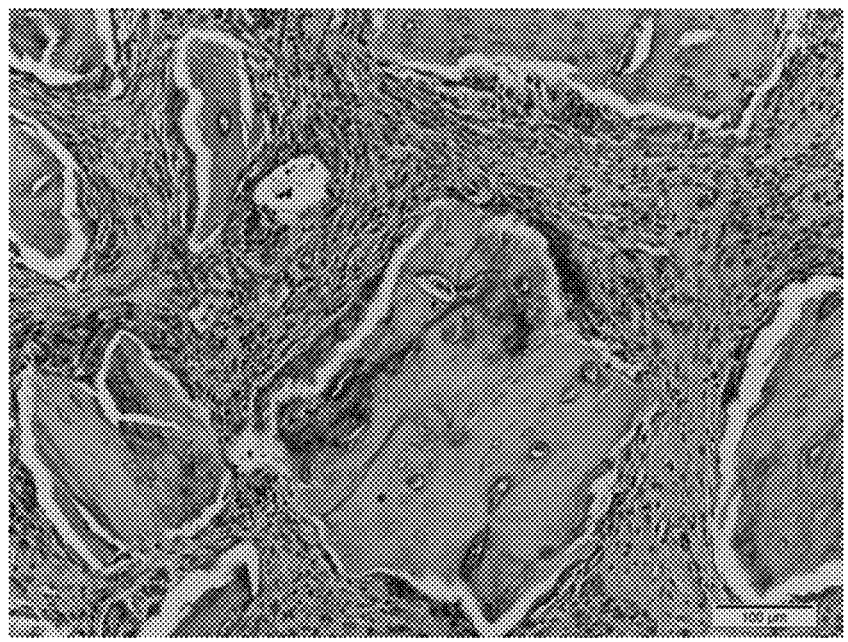
FIGS. 3E and 3F show photomicrographs of histology characterized by immunohistochemistry for acid phosphatase staining.
Figure 3F:
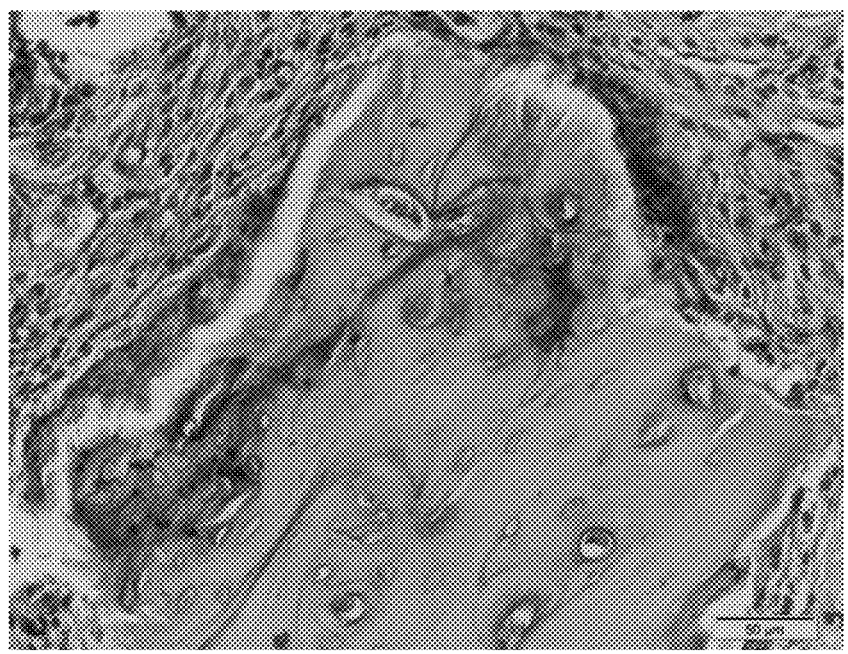
Figure 21:
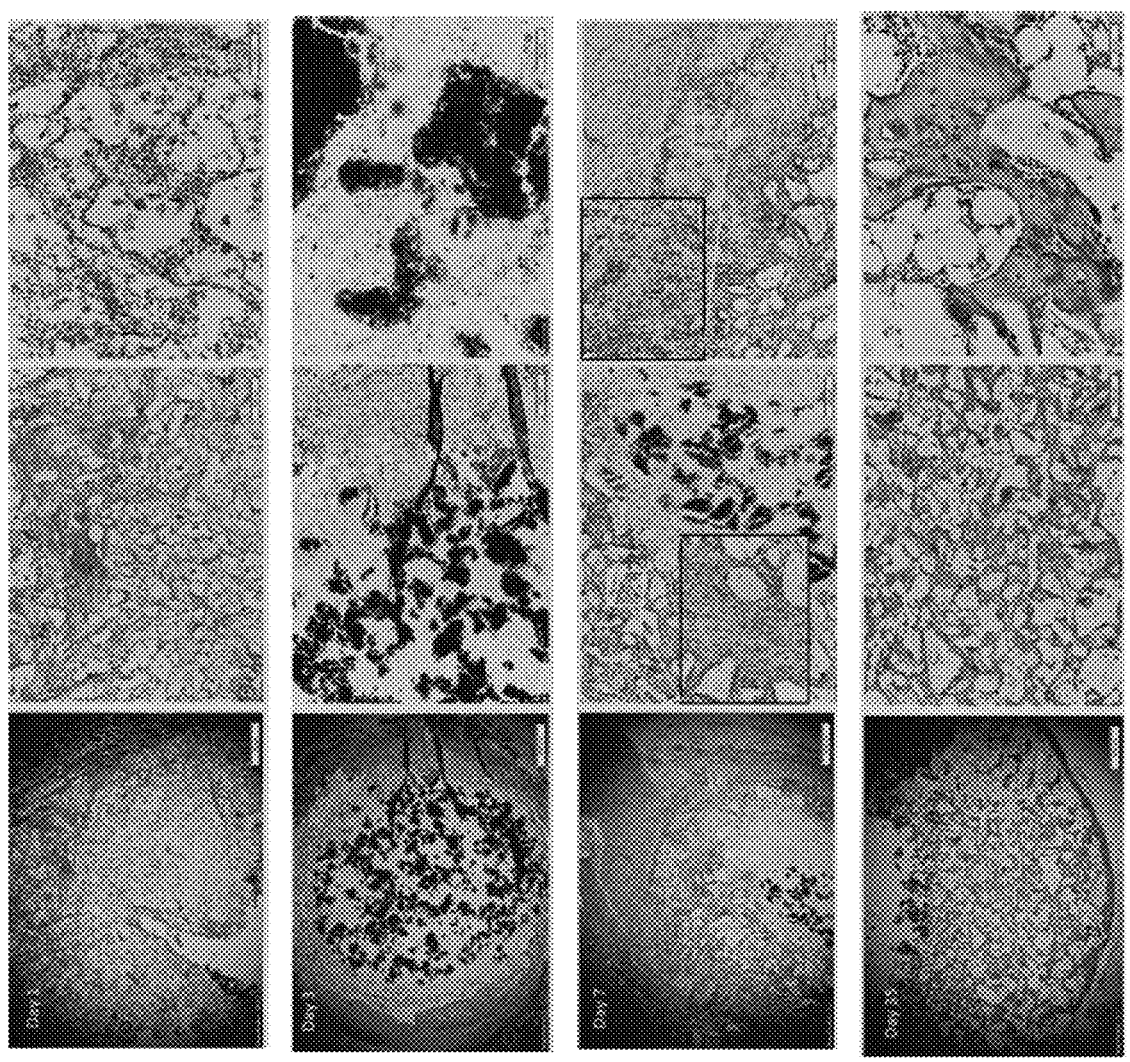
FIG. 21 shows tricalcium phosphate (TCP) implanted in ABC with rhBMP6 at subcutaneous site in rat and analyzed on days 1, 3, 7, and 35. On day 35 new bone has formed between TCP particles (last row).

The results demonstrate that allograft (ALLO) particles when implanted at rat subcutaneous sites induced inflammation and foreign-body reaction due to high mineral content at ectopic sites by recruiting mononuclear phagocytes by day 1-3 which then fused to form multinucleated foreign body giant cells (FBGCs) by day 7-14 (FIG. 3A). The inflammatory insult and fusion of multinucleated FBGCs were significantly reduced in numbers when ALLO particles were formulated within ABC (FIGS. 3B and 3D). In the ABGS implants that contained ABC+ALLO+rhBMP6, there were fewer or no FBGCs with endochondral bone formation (FIGS. 3C and 3D) in apposition to ALLO particles. FIG. 3D represents the average number of multinucleated FBGCs counted morphometrically from three representative histology sections from ALLO, ALLO+ABC and ALLO+ABC+rhBMP6 implants. The multinucleated FBGCs cells recruited by ALLO implants were further characterized by immunohistochemistry for acid phosphatase staining, which were reduced by addition of ABC (FIGS. 3E and 3F). Similar findings were observed when Ceramic (Tri-Calcium Phosphate or Hydroxyapatite or combination thereof) was used as the compression resistant matrix (see FIG. 21).

Example #4: Pharmacokinetics and Cumulative Release of rhBMP6 from ABGS In Vitro and Retention of rhBMP6 in the Implant The autologous bone graft substitute composition containing human blood and allograft was formulated as described in either method #2 or #3. Blood samples from healthy human volunteers were collected from the cubital vein into tubes without anticoagulants. Upon withdrawal, blood was mixed with allograft (particle sizes 2-5 mm or 5-8 mm) and rhBMP6 in two concentrations (either 62.5 or 125 µg per ml of blood). After the coagulation was completed (60 min), ABC+rhBMP6 plus allograft was rinsed with 1 ml of the basal medium. Each implant was placed in a falcon tube containing 3 ml of Dulbecco's modified Eagle medium. Tubes were incubated at 37° C. during 10 days and the medium was replaced on days 1, 3, 6, 8 and 10. The amount of rhBMP6 released from the autologous blood coagulum plus allograft in the medium was determined by rhBMP6-specific ELISA (R&D systems, DY507).

Figure 4A:
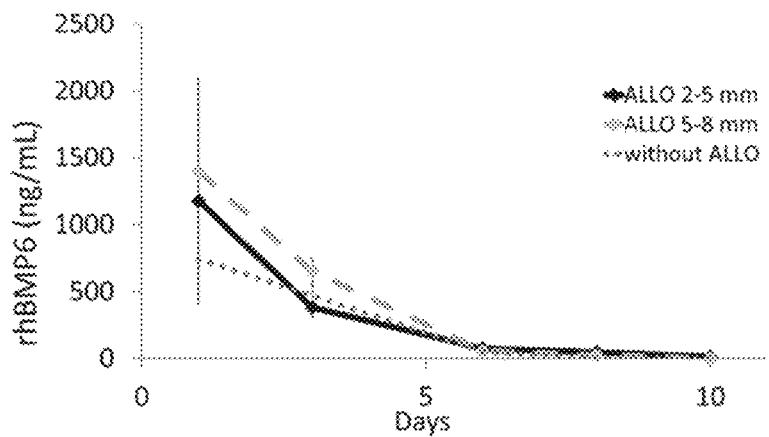
FIG. 4A is a graph illustrating amount of rhBMP6 released from an ABGS without allograft and with allograft of two different particle sizes.
Figure 4B:
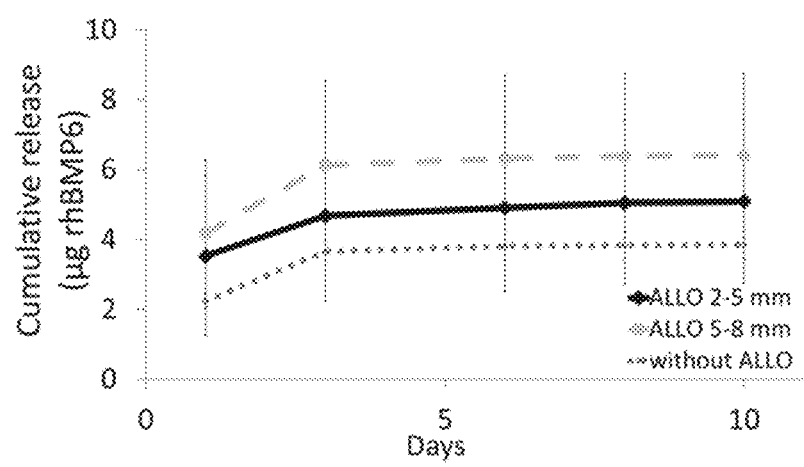
FIGS. 4B and 4C are graphs illustrating cumulative release of rhBMP6 from an ABGS without allograft and with allograft of two different particle sizes.
Figure 4C:
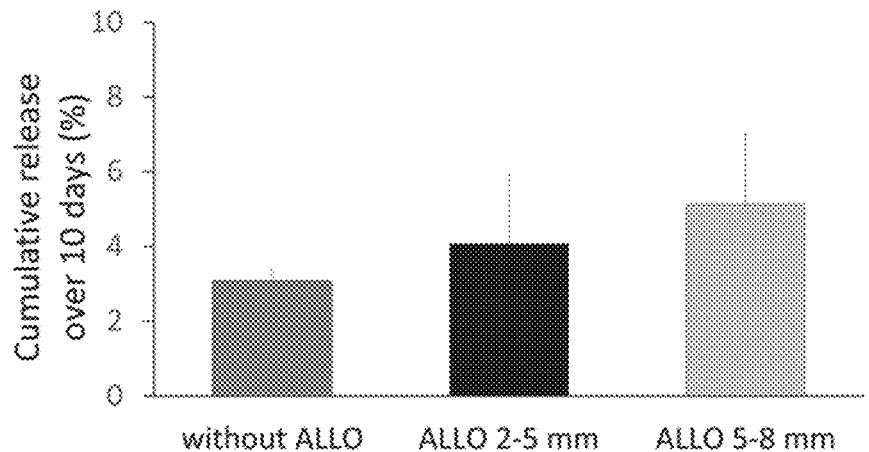

The amount of rhBMP6 released from the autologous bone graft substitute composition without allograft and with allograft of two different particle sizes are shown in FIG. 4A. The autologous bone graft substitute composition was prepared using human blood from volunteers and the compression resistant matrix is human allograft from Bone Tissue Bank in the clinic used for patients. rhBMP6 was released readily in the first 3-6 days, after that it became steady. Though the autologous bone graft substitute composition containing allograft showed a bit more of rhBMP6 release, it was not statistically significant. The cumulative release as measured on days 1, 3, 6, 8 and 10 and the calculated total release (%) from the autologous bone graft substitute composition was about 3-9% of total rhBMP6 dose (FIGS. 4B-4C). Addition of allograft seemed to have slightly more cumulative release. rhBMP6 is mainly bound to plasma proteins in the autologous bone graft substitute composition with or without allograft as examined in vitro. The pharmacokinetics of rhBMP6 is likely to be changed at the implant site as the protein is taken up by the responding cells to trigger endochondral bone differentiation.

RhBMP6 Binding and Release Characteristics with the Autologous Bone Graft Substitute composition (ABGS) containing Ceramics or ALLO:

The added RhBMP6 binds tightly and specifically to ceramics at the surface as well as inside the pores via ionic and hydrophobic interactions and that required 100 mM phosphate to elute the bound protein. The binding of rhBMP6 to coagulum is protein-protein based with plasma proteins and cell membrane at the surface of erythrocytes with hydrophobic interactions and may also likely involve a high affinity binding to heparin-like glycosoaminoglycans as BMP6 is known to bind heparin sulfate. Thus, there are two (orthogonal) mechanisms by which rhBMP6 retained in the CERAMIC-rhBMP6-ABC containing ABGS.

Figure 15:
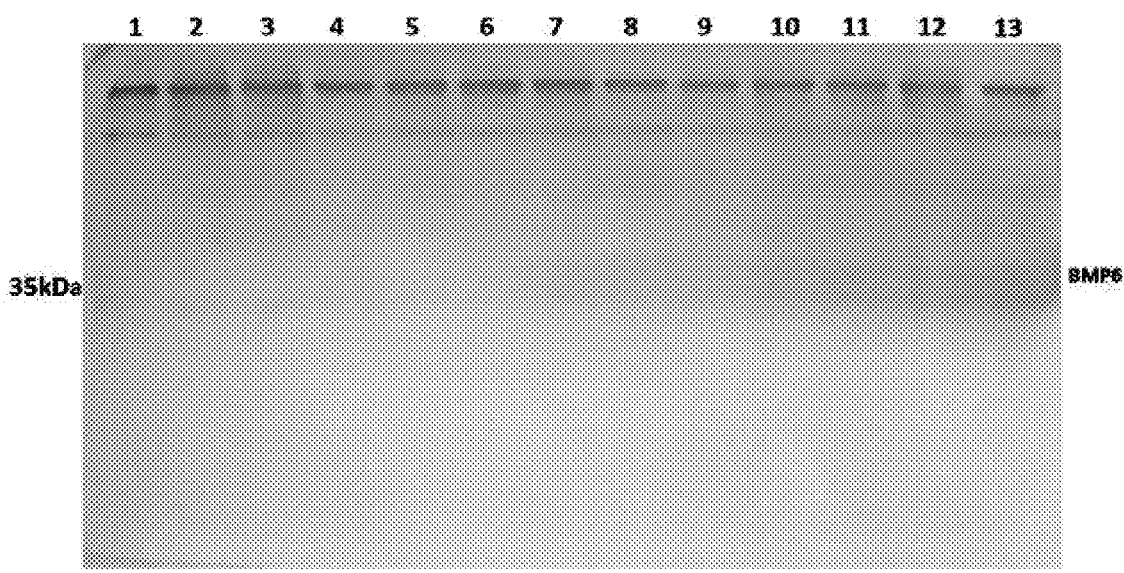
FIG. 15 shows a Blood Coagulum capacity for BMP6 binding.

The very high binding capacity of the coagulum is illustrated by SDS-PAGE and Immunoblot with anti BMP6. (note: Some high MW background is seen at the top in all lanes due to cross-reaction of antibodies.) The Coagulum capacity for BMP6 binding is shown in FIG. 15. Lanes 2-13 show increasing amounts of BMP which had been added for BMP binding in coagulum and could subsequently be quantitatively released by solubilization with SDS sample buffer. Even at 800 µg per ml blood no significant amounts of BMP6 have appeared in serum supernatant and no sign of saturation of the coagulum. This is important as the exuberant bone formation will not occur since there is no extensive release of the BMP. FIG. 16 shows release of BMP from preloaded ceramics during 3-day intervals, as measured by Elisa assay.

Example #5: Target Product Profile of Autologous Bone Graft Substitute Composition: An Autograft Mimetic We present that the autologous bone graft substitute composition (ABGS) that contains recombinant human BMP6 (rhBMP6) dispersed within autologous blood coagulum (ABC), with allograft (ALLO) particles, is capable of inducing new bone formation. BMP6 was chosen as the preferred morphogenetic protein as it does not bind avidly to Noggin, a natural BMP antagonist present in abundance in bone. BMP6 also binds to most of the type I and II BMP receptors and exhibits a high specific alkaline phosphatase activity in osteoblastic cell cultures, hence permitting the use of lower doses as compared to BMP2 or BMP7. The autologous blood coagulum (ABC) was chosen as a carrier as it 1) decreases inflammation, 2) provides circulating osteoprogenitors, 3) promotes rhBMP6 binding with plasma proteins tightly within the fibrin mesh-work and releases slowly as an intact protein, 4) reduces immune responses and avoids generation of antibodies to rhBMP6, and 5) finally provides a permissive environment for endochondral bone differentiation. The ALLO particles were added uniformly across the ABC to provide biocompatibility, good handing properties and compressive resistance.

Figure 22:
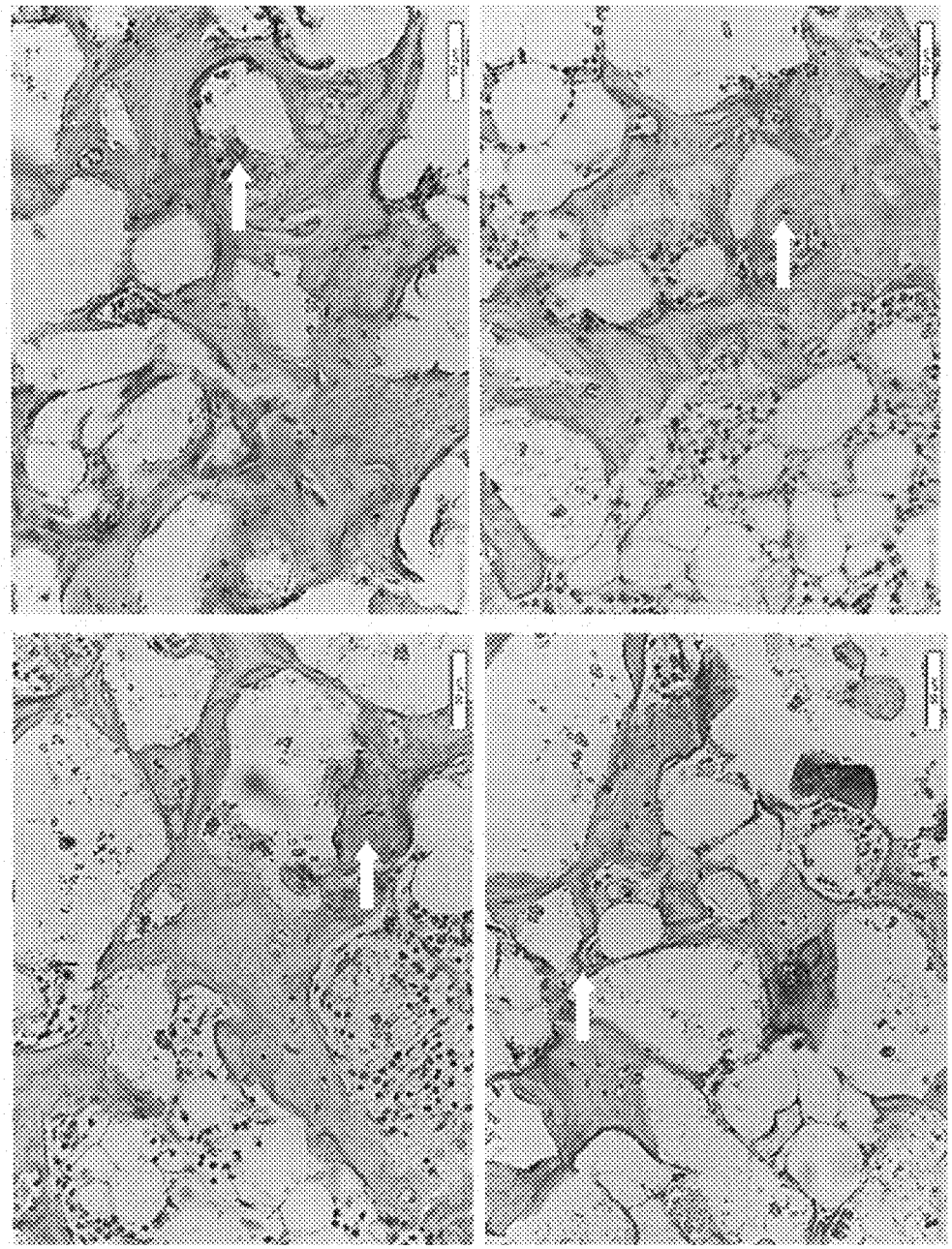
FIG. 22 shows high magnification of implants from FIG. 21 on day 35 indicating that newly formed bone has surrounded TCP particles with signs of substitution of TCP with bone (creeping substitution) (white arrows)

The autologous bone graft substitute composition containing the autologous blood coagulum plus ALLO particles is fabricated with defined rheological properties. The addition of allograft particles reduces the time needed to achieve the autologous blood coagulum and improves handling properties. We observed for the first time that the autologous blood coagulum has an unexpected inherent biological property as it overcomes foreign body responses elicited by high Ca/P-containing mineral (ALLO) at ectopic sites. The autologous blood coagulum reduces significantly the formation of multinucleated foreign-body giant cells around allograft particles and allows the recruitment of mesenchymal stem cells which then, in response to rhBMP6, undergo endochondral bone differentiation. The binding and release characteristic of rhBMP6 and the dose of rhBMP6 required to induce optimal bone formation are comparable in the autologous bone graft substitute composition with or without allograft. The newly formed bone in the autologous bone graft substitute composition containing allograft is compact and undergoes a typical bone remodeling as examined by micro-CT analysis and histology in rat subcutaneous implants, which mimics that of autograft assimilation observed in orthotropic site. The autologous bone graft substitute composition (ABC/Allograft/rhBMP6) induced endochondral bone and the ALLO particles were assimilated with newly formed bone via a creeping substitution (FIG. 22). The autologous bone graft substitute composition (ABC/TCP/rhBMP6) that contained synthetic ceramics is represented in FIG. 22. The autologous bone graft substitute composition induces bone in a dose-dependent manner with an effective rhBMP6 dose at 100 µg/ml in the autologous blood coagulum.

Bovine sourced collagens are used as carriers to deliver the BMP; Bovine Achilles tendon derived acid soluble reconstituted type I collagen mesh as in InFuse®[31] or as a slab-shaped composite with synthetic ceramics as in Amplify®[38] is used to deliver rhBMP2. Bovine diaphysis bone derived insoluble type I collagen as particulate and/or combined with additive CM-cellulose as injectable putty are used for rhBMP7/OP1 as in OP1-Implants®[39] and OP1-Putty®[40]. Sterilization of these bovine sourced collagens by chemical methods or gamma-radiation for clinical uses added unwanted modifications to collagenous carrier as well[40]. Here, we present the autologous blood coagulum as a native carrier to deliver rhBMP6 with allograft (ALLO) as the compression resistant matrix to promote posterolateral lumbar fusion and minimizes adverse events examples like 1) generation of antibody to a BMP when delivered with animal sourced collagen serving as an adjuvant, 2) nerve inflammation[41] as a result of high doses of BMP used and readily released away from the implant sites and 3) nerve compression due to functional impairment of biomechanical bone support.

Example #6: Autologous Bone Graft Substitute Composition (Autologous Blood Vs Autologous Platelet Rich Plasma)

Figure 23:
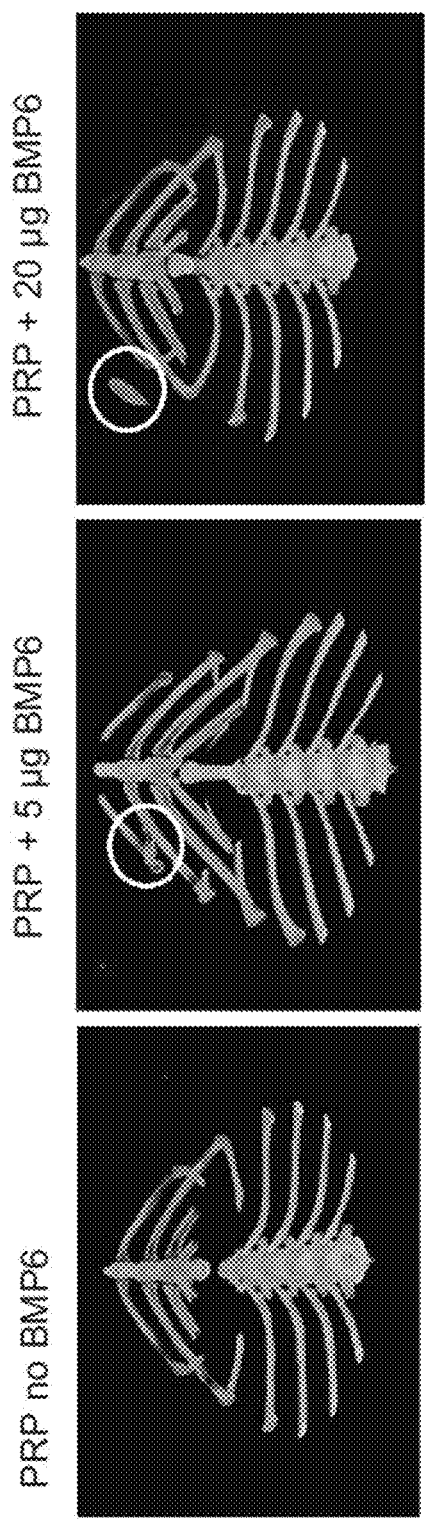
FIG. 23 shows platelet rich plasma (PRP) gel prepared from 2 ml of rat blood and implanted under the rat skin without BMP6, with 5 or 20 µg BMP6. Newly formed bone in BMP6 enriched PRP samples is marked by white circles.

The autologous bone graft substitute composition (ABGS) was formulated using autologous blood (AB) derived platelet rich plasma (PRP) proteins with rhBMP6 and compared it with the autologous bone graft substitute composition formulated with the autologous blood coagulum (ABC). In addition, the autologous bone graft substitute composition was formulated with ABC and PRP. ABGS-ABC (formulated with ABC), ABGS-PRP (formulated with PRP) and ABGS-ABC/PRP (formulated with both ABC and PRP) were examined in rat subcutaneous implant assay. FIG. 23 shows that autologous PRP prepared from rat and implanted under the rat's skin did not form a bone 14 days later, while 5 and 20 μg of BMP-6 added to autologous PRP induced dose dependently new bone (indicated in white circle).

Example #7: Preclinical Studies Performed to Predicting Clinical Outcome

Diaphysis Segmental Defect Model in Rabbits:
The efficacy of the autologous bone graft substitute composition in abridgement of critical bone size defects was tested in the rabbit ulna segmental defect model. The autologous blood was collected from rabbit marginal ear veins in a volume of 1.5 ml. rhBMP6 was added into the autologous blood in amounts of 25 μg, 50 μg and 100 μg with 50 mM concentration of calcium chloride and mixed by rotating the tubes. The autologous blood+rhBMP6 were prepared in a syringe and left on the room temperature to coagulate for 60-90 min. The liquid portion (serum) was removed and the homogeneous, cohesive, injectable and malleable autologous bone graft substitute composition gel was ready for use.

Study protocols were conducted in male laboratory rabbits (*Oryctolagus cuniculus*), New Zealand strain, 10 weeks old (2.3-2.5 kg body weight). Animals were randomly divided into four groups (n=5 each): A) control, defect filled with the autologous blood coagulum (ABC) only; B) defect filled with the ABC+rhBMP6 (25 μg/ml); C) defect filled with the ABC+rhBMP6 (50 μg/ml) and D) defect filled with the ABC+rhBMP6 (100 μg/ml). In another experiment (n=5 per group), the autologous bone graft substitute composition (1.5 mL ABC+rhBMP6 (100 μg/ml) was compared with collagen (150 mg)+rhBMP7 (100 μg/100 mg;) at week 2 and 8 after implantation.

A segment of the ulna measuring 17 mm (large defect) was removed and the autologous bone graft substitute composition was implanted into the defect site, with the radius left intact for mechanical stability, without using of internal or external fixation devices. Radiological images of the right forelimb were taken immediately after surgery and during 23-week bone healing period. During the experiment there were no adverse effects. The healing outcome was analyzed by radiography, micro-CT quantification and histology.

Figure 5:
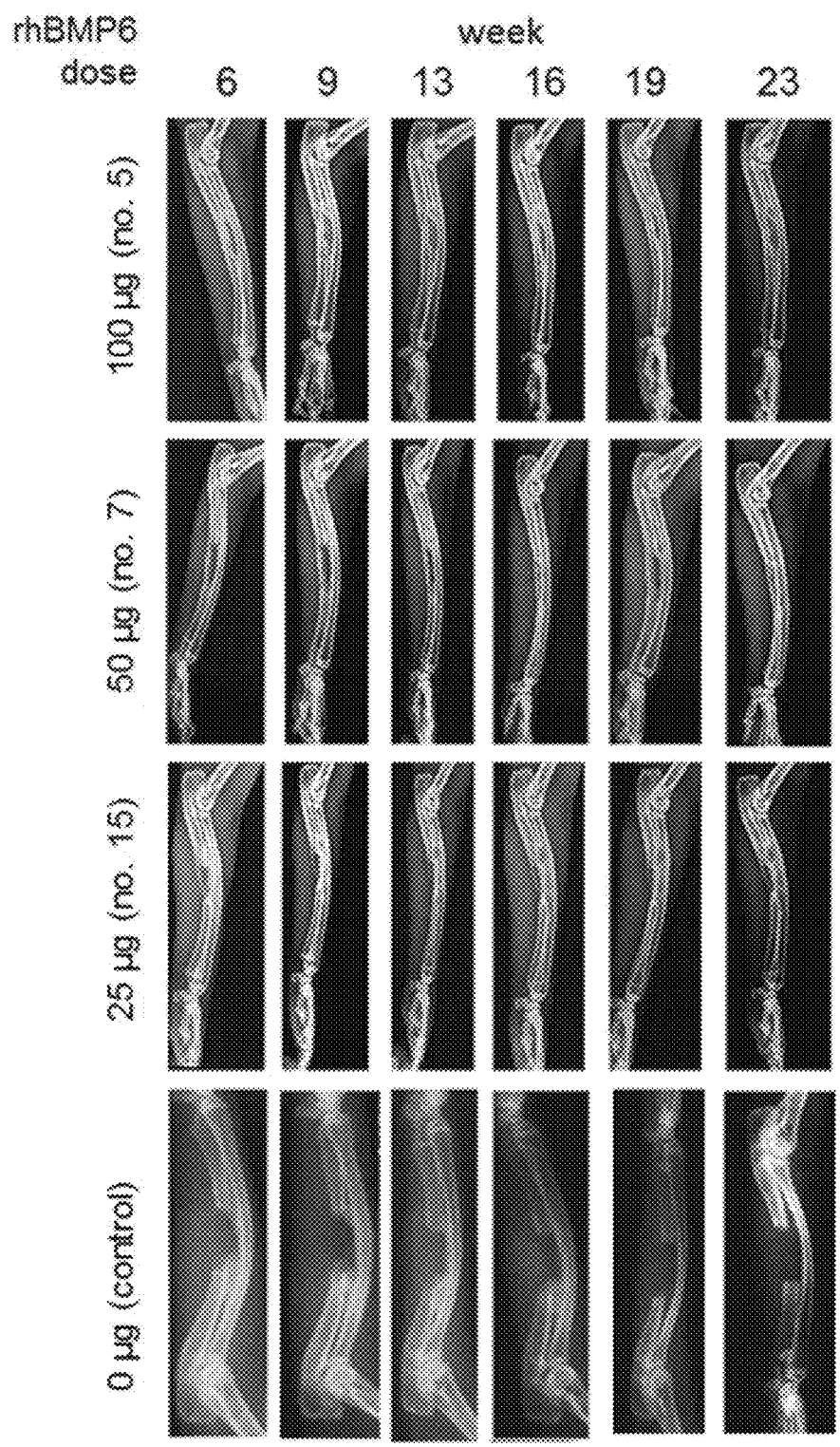
FIG. 5 shows reproducibly induced new bone formation in rabbit ulna and the restored critical size defect assessed by radiography in a dose dependent manner as represented at weeks 6, 9, 13, 16, 19 and 23.
Figure 7:
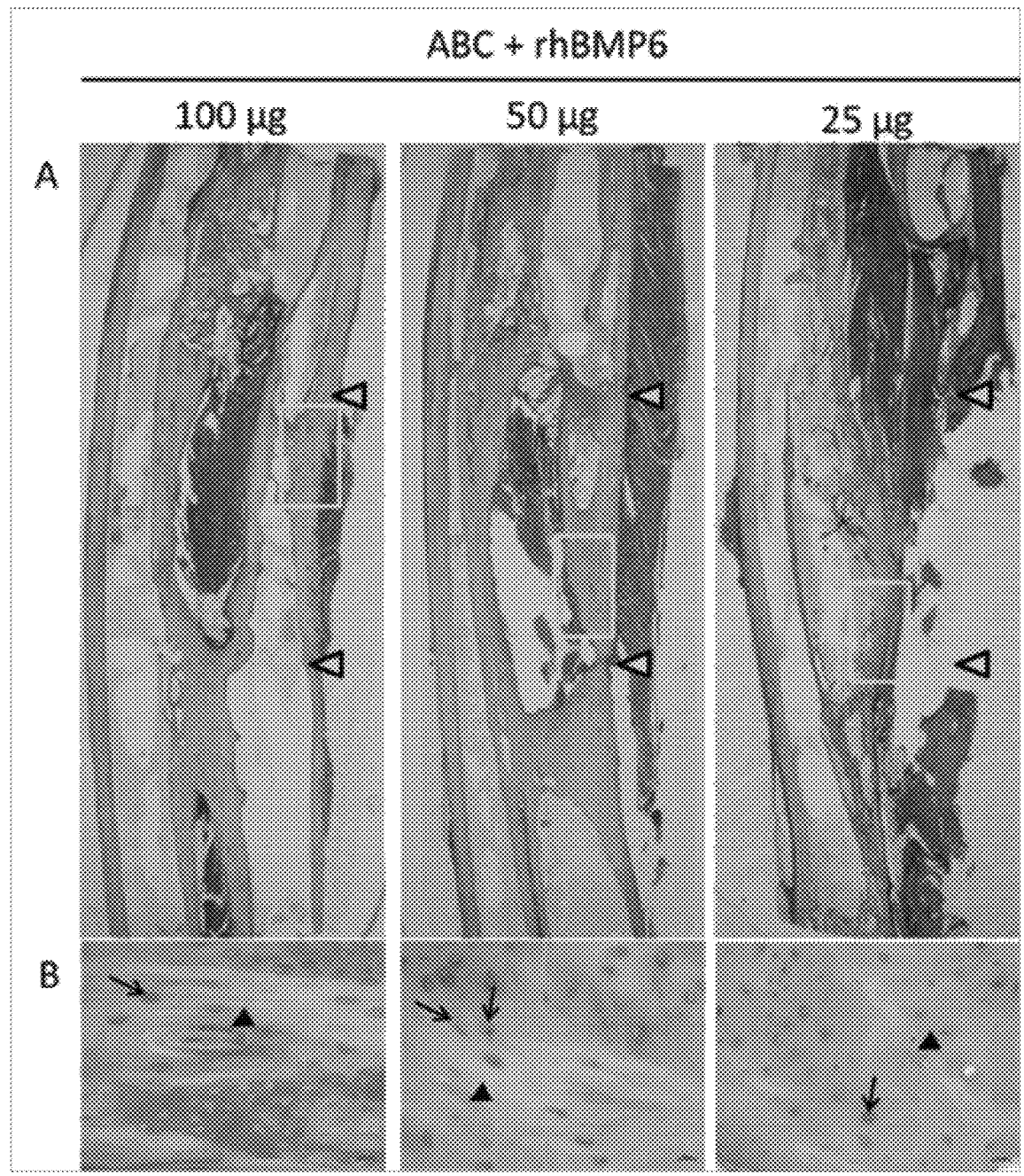
FIG. 7 shows histology sections of rabbit ulna defects at different rhBMP6 doses.

The autologous blood coagulum implanted alone did not result in the formation of new bone and failed to achieve bridgement of the defect (FIG. 5). The autologous blood coagulum (ABC) containing rhBMP6 (ABGS), however, reproducibly induced new bone formation and restored the defect as assessed by radiography. The new bone formation was induced in a dose dependent manner as represented at weeks 6, 9, 13, 16, 19 and 23 (FIG. 5), and all rabbit ulna are shown at the week 23 (FIGS. 6A and 6C). Micro CT analyses showed a dose-dependent increase in bone quantity as examined by bone volume (BV) and medullary volume (MV), which are comparable to the intact bone of the contralateral side (FIG. 6D). The bone quality was further confirmed by histology, as shown in a representative sample from each group (FIG. 7). The dose of 100 μg rhBMP6/ml ABC resulted in the complete restoration with fully established cortices and remodeled medullar canal. Histological evaluation confirmed the full bridgement of ulna critical size defects in rabbits treated with 100 μg rhBMP6/ml ABC (FIG. 7).

Figure 8A:
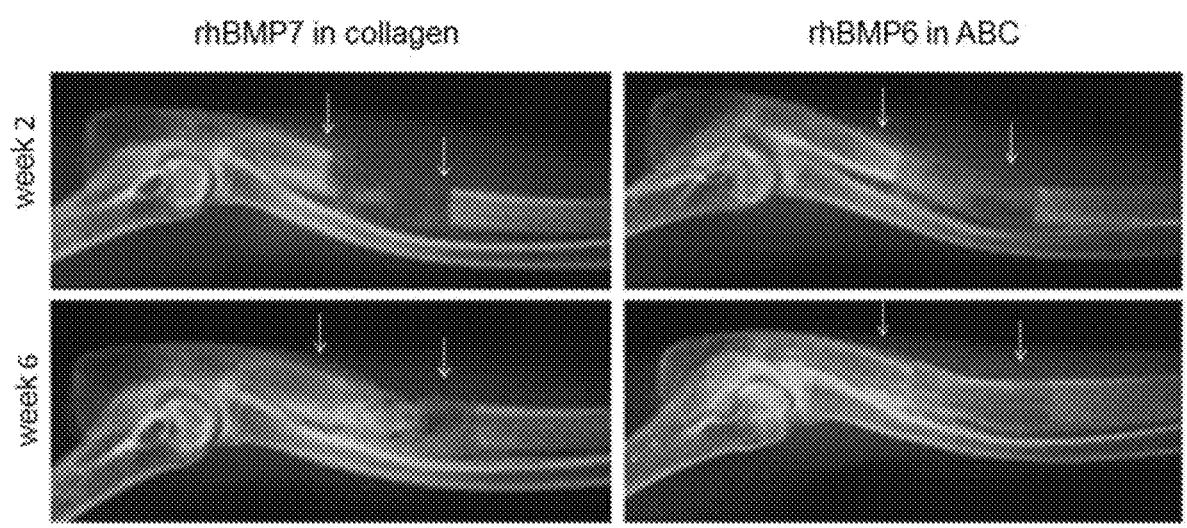
FIG. 8A shows x-ray of rabbit ulna treated with rhBMP7 in collagen and rhBMP6 in an Autologous Blood Coagulum (ABC) as represented at weeks 6 and 2.

In the same model we compared side by side rhBMP7/bovine bone collagen device with the ABGS (rhBMP6/ABC). Collagen alone did not induce bone formation, but rhBMP7 containing collagen induced new bone formation (FIG. 8A). The rhBMP7/bovine bone collagen commercial device contains 3.5 mg rhBMP7/g of collagen, and to fill the rabbit ulna defect we used 300 mg that accounts for the total amount of 1.06 mg rhBMP7 in a collagen carrier. This rhBMP7/collagen induced bridgement of the ulna defect was compared to the ABGS (100 μg rhBMP6 in 1.5 ml blood) as shown in FIG. 8A. ABGS induced, at week 2 and 6, a formation of a new uniform bone and underwent a remodeling to rebridge new cortices with adjacent host bone, while the bone formation with rhBMP7/collagen was delayed. Micro CT analysis confirmed that the ABGS containing rhBMP6 induced on week 8 following surgery around 2× more bone volume (FIG. 8B-C).

The outcome from this preclinical study allowed us to evaluate the First-in-Human (FIH) randomized, placebo controlled and double blinded Phase I safety study in patients with Distal Radius Fractures (DRF) (1) and Phase I/II efficacy and safety study in patients with High Tibial Osteotomy (HTO) (2)

Posterolateral Lumbar Fusion (PLF) Study in Rabbits:
The autologous bone graft substitute composition was evaluated for bone inducing activity for spinal fusion in posterolateral lumbar fusion (PLF) rabbit model. Study protocols were conducted in Male New Zealand White laboratory rabbits (*Oryctolagus cuniculus*), New Zealand strain, 14 weeks old, body weight between 3-5 kg. 28 skeletally mature rabbits underwent bilateral posterior intertransverse process fusion between lumbar vertebrae L5-L6. Animals were divided into 7 experimental groups of four each as follows: the autologous blood coagulum (ABC) alone served as control; the ABC with 50 μg (0.05 mg/ml; 125 μg per device) rhBMP6; the ABC with 100 μg (0.1 mg/ml; 250 μg per device) rhBMP6; the ABC with 200 μg (0.2 mg/ml; 500 μg per device) rhBMP6; the ABC with 200 μg (0.2 mg/ml; 500 μg per device) rhBMP6 and devitalized rabbit bone allograft (0.3 g/ml); the ABC with 400 μg (0.4 mg/ml; 1000 μg per device) rhBMP6 and devitalized rabbit bone allograft (0.3 g/ml); the ABC and devitalized rabbit bone allograft (0.3 g/ml) without rhBMP6 served as a control. A volume of the ABC for device preparation was 2.5 ml per implantation side.

Figure 9:
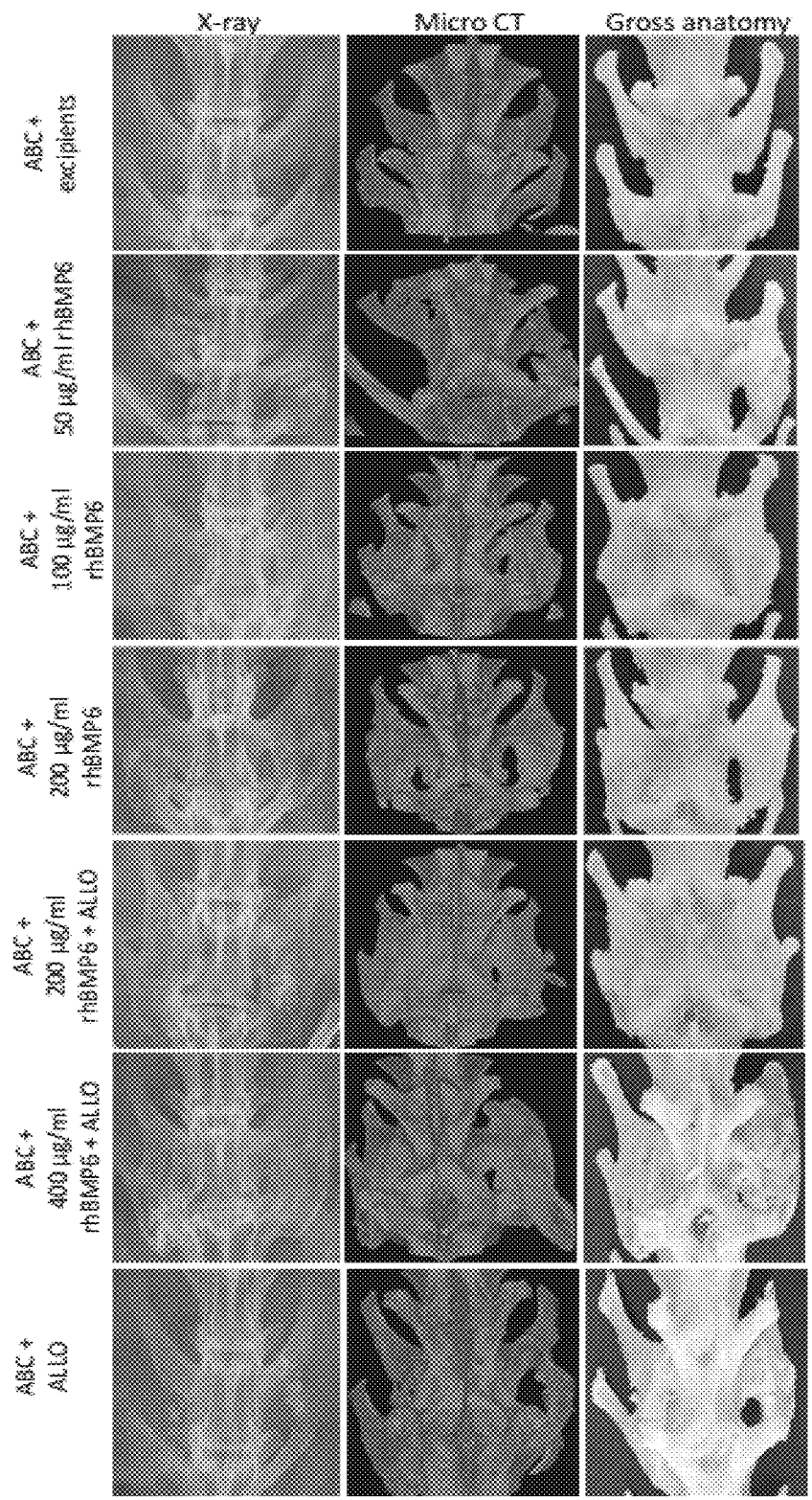
FIG. 9 shows X-ray, Micro-CT and Gross Anatomy photographs of an ABGS with and without ALLO at varying doses of rhBMP6 per ml ABC as compared to ABC alone and ABC plus ALLO groups for spinal fusion in posterolateral lumbar fusion (PLF) of rabbit.
Figure 10A:
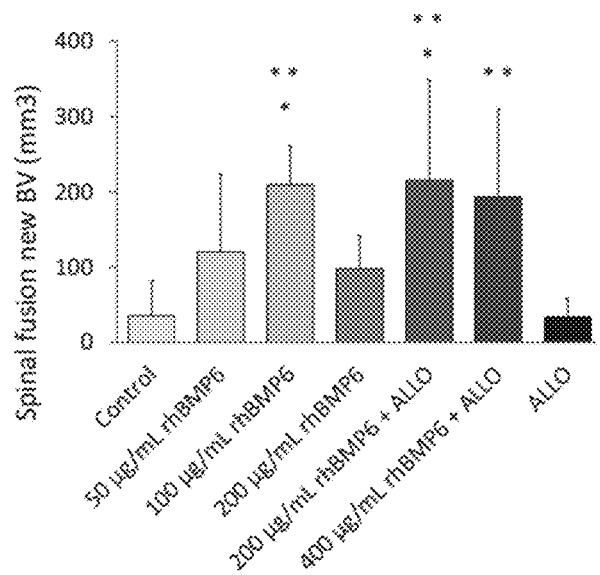
FIGS. 10A to 10D show graphs illustrating the quantitative measurements on bone volume, trabecular number and trabecular inter-connectivity, as determined by micro-CT analyses.
Figure 10B:
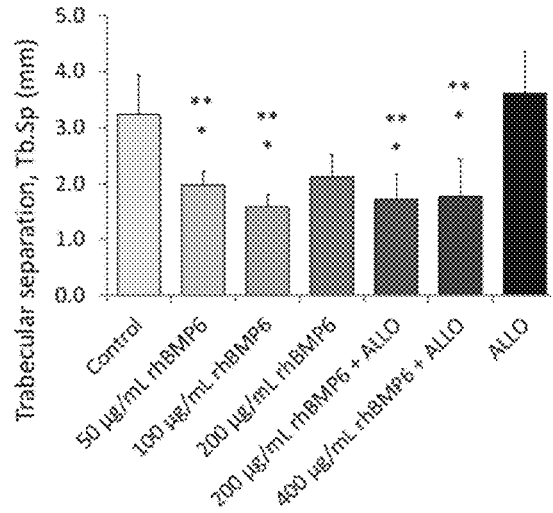
Figure 10C:
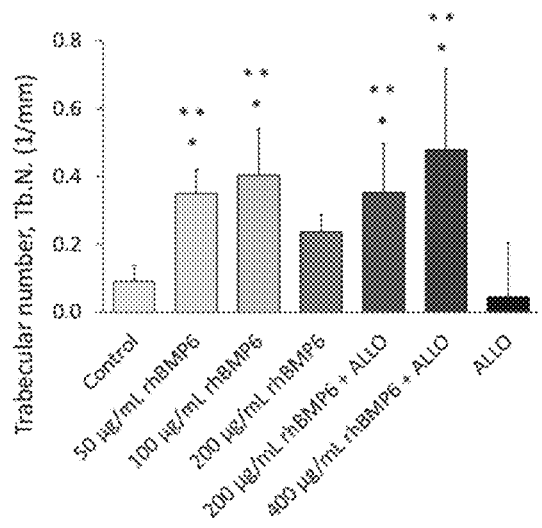
Figure 10D:
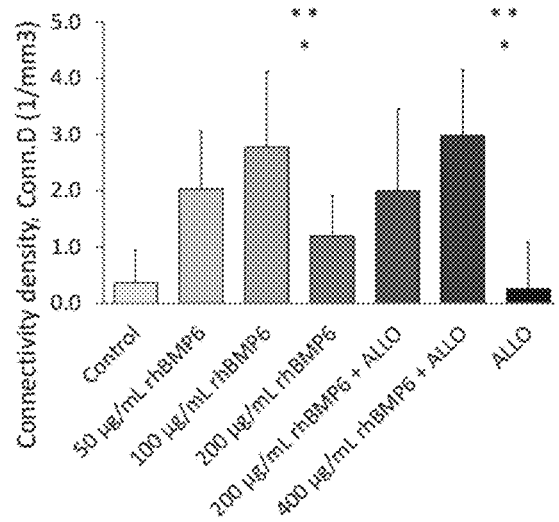

FIG. 9 shows X-ray, Micro-CT and Gross Anatomy photographs of the autologous bone graft substitute composition with and without ALLO at varying doses of rhBMP6 per ml of autologous blood coagulum (ABC) as compared to the ABC alone and the ABC plus ALLO groups. The newly formed bone in between two transfer processes by the autologous bone graft substitute composition is compact and uniformly distributed within the implant and separated from periphery of the soft tissue surrounding the implant as examined at 14-weeks. The group that contained rhBMP6 at 50 µg/ml ABC (125 µg/implant) demonstrated new bone formation but achieved fusion in two out of 4 rabbits, suggesting that the amount of rhBMP6 might not have been sufficient. At rhBMP6 100 µg/ml ABC (250 µg/implant), a complete fusion was observed in all the rabbits. At rhBMP6 200 µg/ml ABC (500 µg/implant), again all rabbits showed fusion on both sides but not more than the amount observed in the 100 µg/ml ABC group. Since ALLO is capable of inducing inflammation and forming multinucleated FBGCs, we have formulated autologous bone graft substitute composition implants that contained 2×rhBMP6 at 200 or 4×rhBMP6 at 400 µg/ml ABC (500 or 1000 µg/implant). The autologous bone graft substitute composition plus ALLO that contained 200 µg/ml ABC (500 µg/implant) induced a complete fusion with bone volume comparable to that of the autologous bone graft substitute composition that had 100 µg/ml ABC (250 µg/implant) and an increase amount of rhBMP6 to 400 µg/ml ABC (1000 µg/Implant) did not further increase the bone volume. The groups that had the ABC alone or the ABC plus ALLO did not fuse at all although the ABC contained endogenous circulating osteoprogenitors and growth factors within ALLO particles and ALLO can release endogenous BMPs upon resorption. The contact area between the transverse processes and the newly formed bone was indistinguishable and fused into one continuous bone segment. The quantitative measurements on bone volume, trabecular number and trabecular interconnectivity, as determined by micro-CT analyses are shown in FIGS. 10A-10D. The autologous bone graft substitute composition at rhBMP6 100 µg/ml ABC appears to be the optimal dose and doubling the dose not necessarily increased the bone formation parameters. The autologous bone graft substitute composition plus ALLO implants that contained either 200 or 400 µg/mL ABC also resulted in new bone formation comparable to the autologous bone graft substitute without ALLO at 100 µg/mL ABC.

Figure 11A:
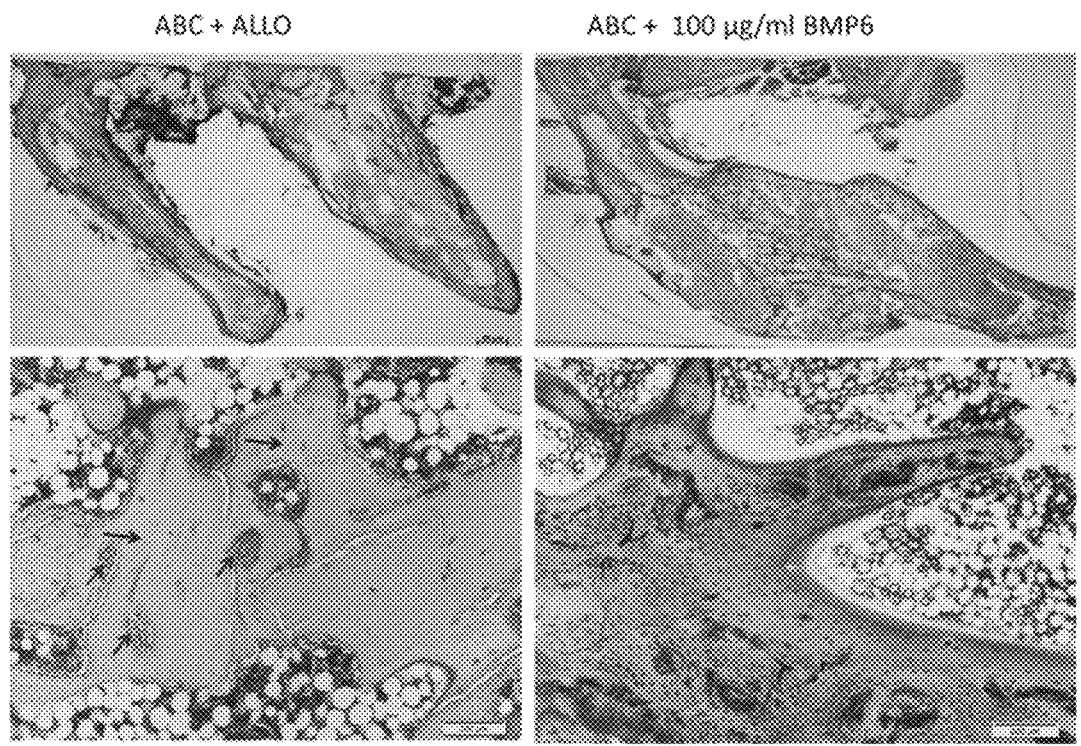
FIG. 11A shows the histology of an ABGS implant. It shows new bone formation with a typical remodeling and osteointegration at the interface in between the newly formed bone and the native transverse processes.
Figure 11B:
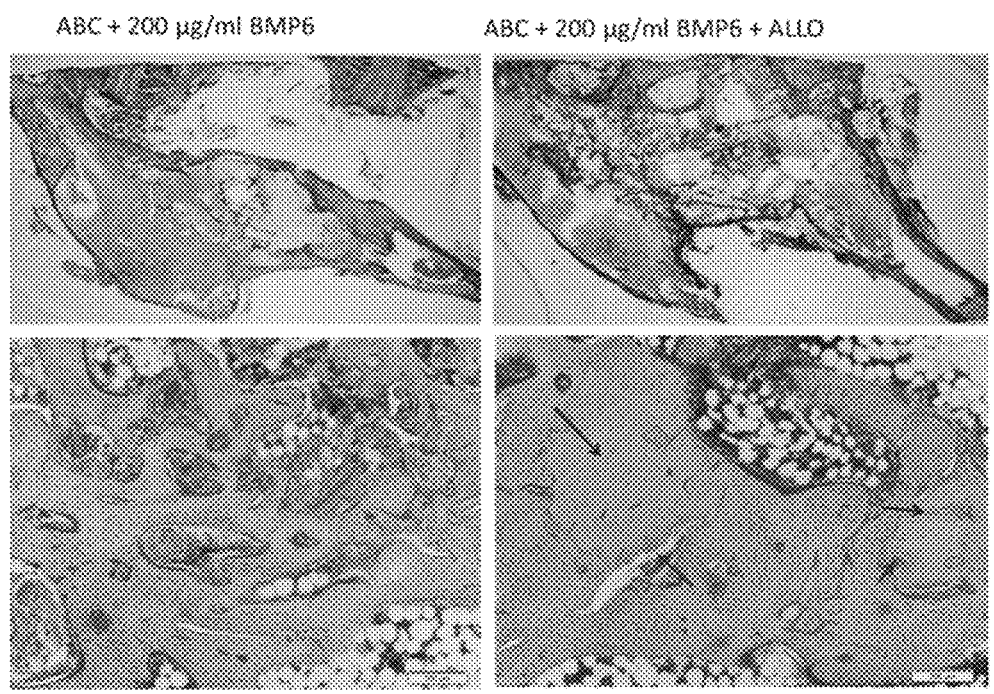
FIG. 11B shows the histology of sera of rabbit treated with ABC/rhBMP6 implants at day 21 after ABGS implantation as compared to day 0.
Figure 11C:
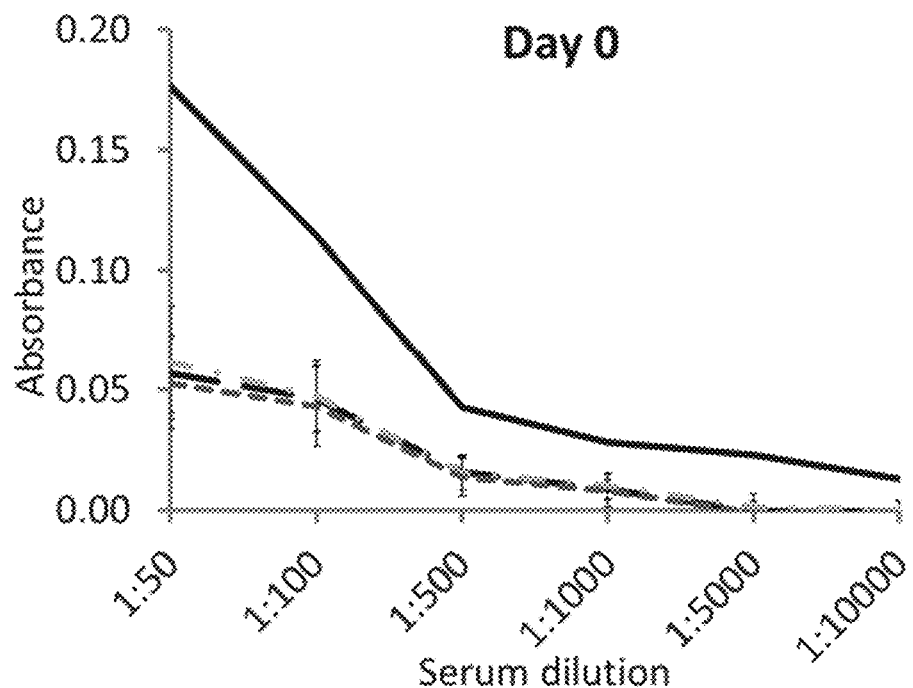
FIG. 11C shows absorbance in dependence on serum dilution at day 0 at 1 and 2 mg rhBMP6.
Figure 11D:
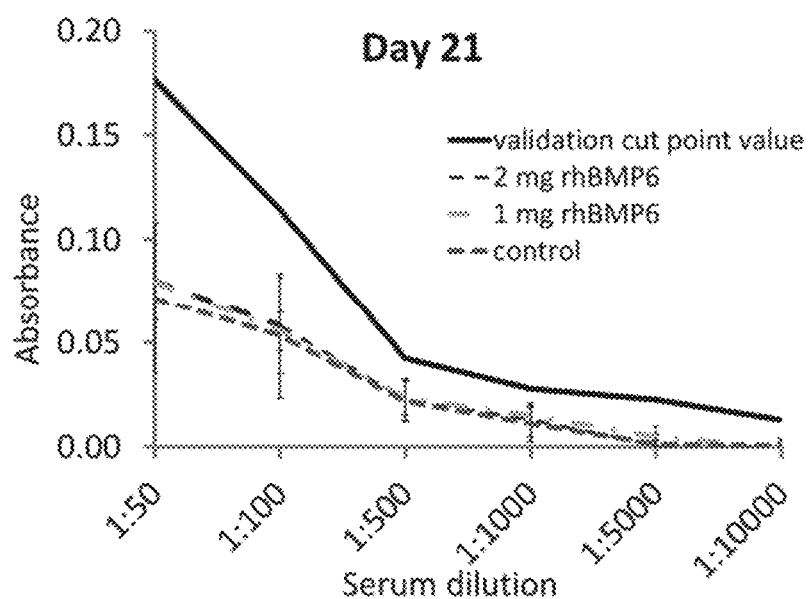
FIG. 11D shows absorbance in dependence on serum dilution at day 21 at 1 and 2 mg rhBMP6.

The histology of the autologous bone graft substitute composition implants showed new bone formation with a typical remodeling and osteointegration at the interface in between the newly formed bone and the native transverse processes (FIG. 11A). In the autologous bone graft substitute composition containing ALLO implants, the newly formed bone undergoes a rapid bone remodeling and fully assimilated with ALLO particles and are eventually replaced by creeping substitution as shown in ABC/rhBMP6/ALLO at 200 µg/ml (500 µg/implant) at low and high magnification (FIG. 11A). The histology of ABC/ALLO showed absence of new bone except the formation of fibrous tissue. Furthermore, it is noteworthy to mention there were no anti-rhBMP6 antibodies detected in sera of rabbit treated with ABC/rhBMP6 implants at day 21 after an autologous bone graft substitute composition implantation as compared to day 0 (FIG. 11B). FIGS. 11C and 11O illustrate absorbance in dependence of serum dilution at day 0 and day 21 at 1 and 2 mg rhBMP6.

Posterolateral Lumbar Fusion (PLF) Study in Sheep

Study protocols were conducted in female sheep (*Ovis* spp.), mixed breed, aged 2 to 3 years, with health certificate, body weight between 60 to 70 kg.

Two separate PLF experiments have been performed in sheep. In the first experiment, 8 female sheep were surgically treated with the autologous blood coagulum (ABC) alone (n=2) and with the ABC containing 62.5 µg/ml (0.5 mg total) rhBMP6 (n=6) without instrumentation. In the second experiment, 14 sheep were administered with the ABC containing 187.5 µg/ml (1.5 mg total) rhBMP6. Animals were assigned to three groups: group A, the ABC alone (n=2), group B, the ABC/rhBMP6 with instrumentation (n=6) and group C, the ABC/rhBMP6/and devitalized sheep allograft (2 g/implant) with instrumentation (n=6). The surgeries were carried out under general anesthesia and were performed for all animals by the same surgical team. Autologous blood sample for implant preparation (16 mL) was collected from the jugular vein of the animal and two implants (8 mL each) bilaterally per animal were prepared and implanted following decortication of the lateral aspect of transverse processes until bleeding was apparent. Sheep were randomly assigned to the group, and received appropriate implants placed bilaterally at the transverse process and the lamina. Clinical and radio-graphical supervision was conducted by a veterinarian immediately after surgery, at weeks 8 and 27 when the study was terminated. During the experiment, no adverse effects in any experimental group were observed.

Figures 12C, 12D:
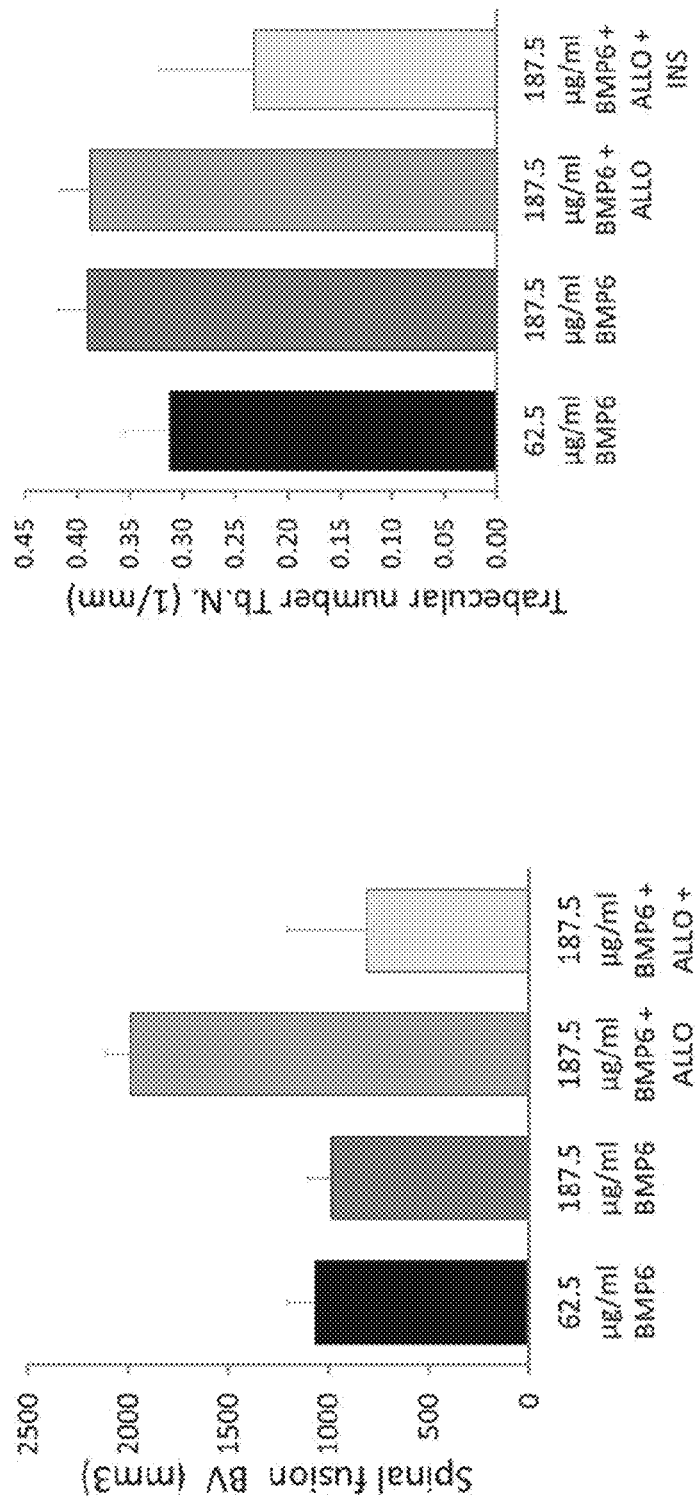
FIGS. 12C to 12F show µCT quantitative analysis of spinal fusion bone volume (C), trabecular number (D), trabecular separation (E) and connectivity density (F)
Figures 12E, 12F:
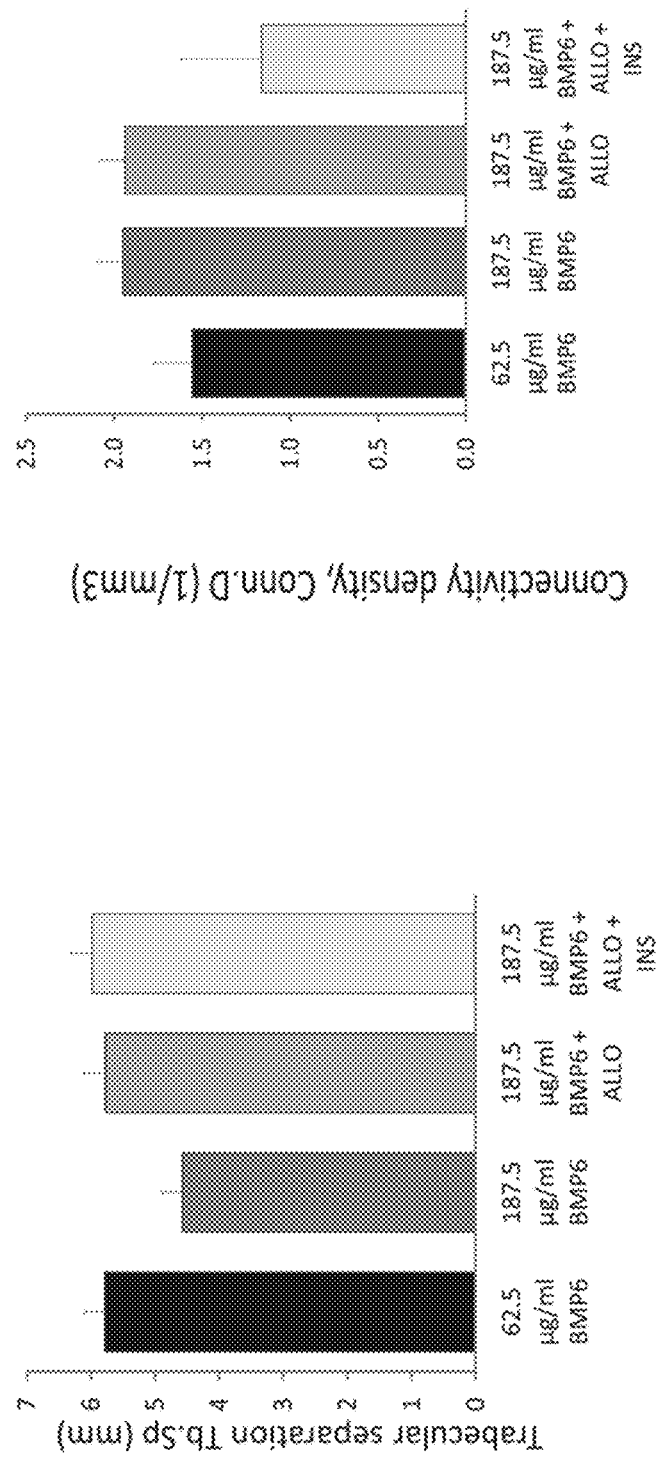

We evaluated the autologous bone graft substitute composition without ALLO at a dose of rhBMP6 62.5 µg/ml ABC (0.5 mg/implant) or rhBMP6 187.5 µg/ml ABC (1.5 mg/implant). Both groups induced new bone formation and achieved a complete fusion harvested at 6-months post implantation as examined by X-ray (FIG. 12A) and micro-CT (FIG. 12B). There is no apparent difference in the amount of bone formed between the two doses, suggesting rhBMP6 in the range of approximately 100 µg/mL ABC appeared to be an effective dose and there is not much difference among the effective doses both in rabbit and sheep PLF studies. Examination of the autologous bone graft substitute composition with ALLO at rhBMP6 187.5 µg/mL ABC (1.5 mg/implant) with and without instrumentation also induced new bone formation and showed significantly more than the autologous bone graft substitute composition without ALLO (FIGS. 12C-12F). Sheep treated with the autologous bone graft substitute composition and instrumentation had a success of bilateral new bone formation of approximately 83% (2/12 implants did not fully fuse), while addition of allograft bone to the autologous bone graft substitute composition increased the success rate of fusion to approximately 93% (1/12 implants did not fully fuse) (see, FIG. 12)

Figure 13A:
FIG. 13A shows a gross anatomy sheep spinal fusion specimen with newly formed bone fully integrated with lumbar vertebrae transverse processes (white arrows)
Figure 13B:
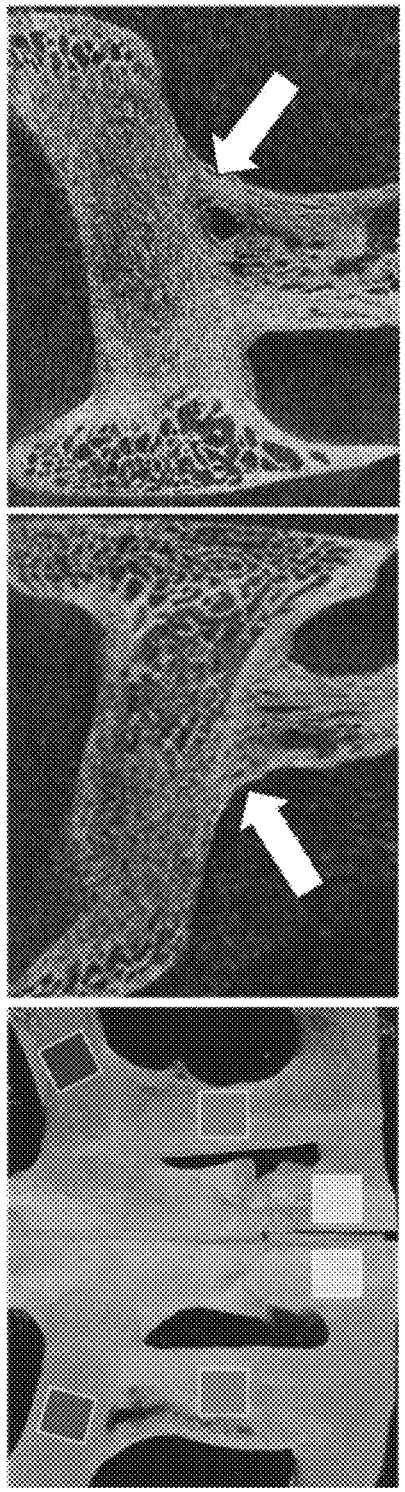
FIG. 13B shows bilateral quadrangular areas of lumbar vertebrae (white boxes), transverse processes (black boxes) and newly formed bone between transverse processes (gray boxes) in which morphometric parameters in FIGS. 13C to 13E have been measured. More precise transverse section of full integration of transverse processes with newly formed bone is shown in the right panel of FIG. 13B (white arrows)

Photomicrographs of gross anatomy of spinal fusion from sheep PLF study bilateral and at the inter-space between transverse processes with newly formed bone are shown in FIG. 13A and micro-CT analysis of the same in FIG. 13B from a representative sheep. The osteointegration between newly formed bone at ectopic sites and native transverse processes was indistinguishable and the fusion was compact and strong. The quantitative measurements of bone volume, structure model index and bone thickness of newly fused bone and the adjacent native transverse process and lumbar vertebrae, as examined by micro-CT analysis, are presented in FIGS. 13C to 13E. The newly formed bone had an increased bone volume, trabecular number and trabecular inter-connectivity as compared to the native transverse bone and the adjacent lumbar vertebrae Studies are in progress to define the dose and the physical characteristics of ALLO particles and the required amount (mass per volume of ABC) that are required for successful long-lasting lumbar fusion in between two transverse processes of a single level and multi-levels in sheep. The outcome from rabbit and sheep PLF studies allowed us to evaluate in randomized and double-blind controlled Phase II efficacy posterolateral lumbar inter-body fusion (PLIF) against autograft (3)

Anterior Lumbar Inter-body Fusion Study in Sheep

The efficacy of the autologous bone graft substitute composition with rhBMP6 was tested in the anterior lumbar spinal fusion in sheep after implantation of the DePuy Cervical CFRP I/F cage. 10 female sheep (Merinolandschaf breed), aged 3-4 years, weighing 50-60 kg, were used for the experiment and divided into 2 experimental groups, namely, control: cage filled with the autologous blood coagulum (ABC) without rhBMP6 (n=4) and experimental: cage filled with the autologous blood coagulum with 250 µg/ml of rhBMP6 (n=5).

The surgeries were carried out under general anesthesia and were performed for all animals by the same surgical team. Blood sample for implant preparation (2 ml) was collected from the jugular vein. Cages are made from carbon fiber reinforced polymer and measure (width/depth/height) 15 mm×12 mm×5 mm. Upon excision of the intervertebral disc (L5-L6) and rasping the cartilage of the end plate the cervical cage was implanted and filled with approximately 1 cc of blood coagulum, while another 1 cc was distributed bilaterally around the cage. Sheep were clinically and radiographically supervised immediately after surgery, 7 and 11 weeks later.

The time course of fusion maturation was assessed by surgical examination, radiography and µCT analysis. Anteroposterior and lateral plain radiographs were made of the spines under consistent conditions. The status of the fusion was evaluated on the plain radiographs. The radiographs were assessed independently by three orthopedic surgeons who were blinded. Computerized tomography scans were made to assess the fusion in cross section and in three dimensions.

The experiment was terminated at week 11 following surgery and all animals survived, except one sheep from the control group which died due to respiratory infection. No side effects regarding mobility, partial or total paralysis, nerve irritation and/or pain, decreased food intake and weight loss were recorded. No ectopic ossifications, edema, or any other visible morphological change were observed. In sheep that received rhBMP6, newly formed bone was present in and outside the cage (n=5), and the bone was fused with both vertebral bodies. Some bone was formed in the cage of control animals, but the fusion was not complete. The bone volume and thickness of newly formed bone were significantly higher in the ABGS with rhBMP6 treated sheep, as compared to control animals. The results of anterior interbody spinal fusion (ALIF) model in sheep after 11 weeks are presented in FIG. 14.

Figure 14:
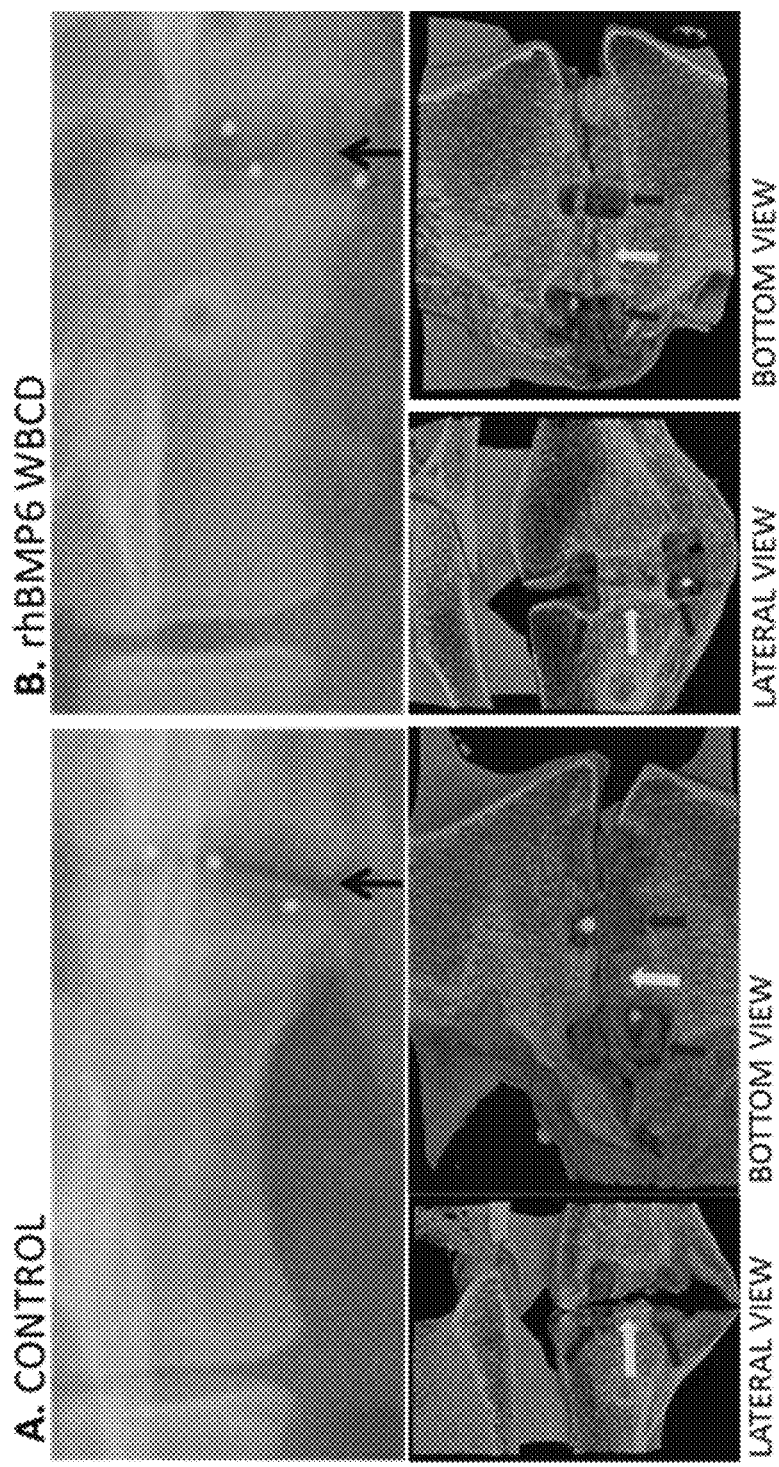
FIG. 14 shows x-ray and µCT scans of anterior interbody spinal fusion (ALIF) model in sheep after 11 weeks of surgery.

With reference to FIG. 14, the x-ray of the control sheep the space in between two vertebrae (black arrow) is not fused by newly formed bone, as also evidenced on µCT scans by white arrows pointing to the bone inside the cage and red arrows indicating the space outside the cage (lateral and bottom views). In the x-ray of the sheep treated with the autologous bone graft substitute composition and rhBMP6 there is newly formed bone between two adjacent vertebrae which is confirmed on µCT scans by a continuous bone (white arrow on the lateral and bottom views) and empty space outside the cage (dark arrows on the lateral and bottom views). This sheep experiment using cervical cage (human) for ALIF demonstrated that the autologous bone graft substitute composition with rhBMP6 (250 µg/ml) resulted in a full fusion of the two adjacent lumbar vertebrae, as compared to incomplete fusion in control animals.

REFERENCES

Asahina, I., Sampath, T. K., Nishimura, I. and Hauschka, P. V. (1993). Human Osteogenic Protein-1 induces both chondroblastic and osteoblastic differentiation of osteoprogenitor cells derived from newborn rat calvaria. *J. Cell. Biol.* 123:921-933.

Cahill, K. S., Chi, J. H., Day, A., Claus, E. B. (2009) Prevalence, complications, and hospital charges associated with use of bone-morphogenetic proteins in spinal fusion procedures. JAMA 302:58-66

Carragee, E. J., Hurwitz, E. L., Weiner, B. K. (2011) A critical review of recombinant human bone morphogenetic protein-2 trials in spinal surgery: emerging safety concerns and lessons learned. Spine J 11:471-491

Executive Summary for P050036 Medtronic's AMPLIFY™ rhBMP-2 and analogs Matrix Orthopedic and Rehabilitation Devices Advisory Panel (2010) Food and Drug Administration.

Gupta S, M. V., Gupta M C (2017) Biology of spine fusion and application of osteobiologics in spine surgery. In: Vukicevic S, Sampath. KT. (ed) Bone Morphogenetic Proteins: Systems Biology Regulators. Springer International Publishing Griffith, D. L., Oppermann, H., Rueger, D. C., Sampath, T. K., Tucker, R. F. and Carlson, W. D. (1994). Crystallization and preliminary crystallographic data of recombinant human Osteogenic Protein-1 (hOP-1). *J. Mol. Biol.* 244: 657-8.

Kim D H, Rhim R, Li L, Martha J, Swaim B H, Banco R J, et al. Prospective study of iliac crest bone graft harvest site pain and morbidity. Spine J. 9:886-92, (2009)

Massagué J (1998) TGF-β signal transduction. *Annu Rev Biochem* 67: 753-791

Medtronic Sofamor Danek USA, Inc. INFUSE Bone Graft product information: Oral/Facial. Memphis, Tenn.; 2006.

Mobbs, R. J. et al. (2015) Lumbar interbody fusion: techniques, indications and comparison of interbody fusion options including PLIF, TLIF, MI-TLIF, OLIF/ATP, LLIF and ALIF. J Spine Surg 1:2-18

Sampath T K. The Systems Biology of Bone Morphogenetic Proteins. In: Vukicevic S, Sampath, K T, editor. Bone Morphogenetic Proteins: Systems Biology Regulators. Springer International Publishing; 2017. p. 15-38

Sampath T K, Reddi A H. Dissociative extraction and reconstitution of extracellular matrix components involved in local bone differentiation. Proc Natl Acad Sci USA. 1981; 78(12):7599-603.

Sampath, T. K., Muthukumaran, N. and Reddi, A. H. 1987. Isolation of osteogenin, an extracellular matrix-associated, bone-inductive protein, by heparin affinity chromatography. *Proc. Natl. Acad. Sci. USA* 84: 7109-7113.

Sampath, T. K., Coughlin, J. E., Whetstone, R. M., Banach, D., Corbett, C., Ridge, R. J., Ozkaynak, E., Oppermann, H. and Rueger, D. C. 1990. Bovine osteogenic protein is composed of dimers of OP-1 and BMP-2A, two members of the Transforming Growth Factor-ß superfamily. *J. Biol. Chem.* 265: 13198-13205.

Sampath T K, Maliakal J C, Hauschka P V, Jones W K, Sasak H, Tucker R F, et al. (1992) Recombinant human osteogenic protein-1 (hOP-1) induces new bone formation in vivo with a specific activity comparable with natural bovine osteogenic protein and stimulates osteoblast proliferation and differentiation in vitro. J Biol Chem. 267(28):20352-62.

Sampath T K, Rueger D C (1994) Structure, function and orthopedic application of osteogenic protein-1 (OP-1) Complications in Orthopedics 9:101-107

Song K, Krause C, Shi S, Patterson M, Suto R, Grgurevic L, et al. (2010) Identification of a key residue mediating bone morphogenetic protein (BMP)-6 resistance to noggin inhibition allows for engineered BMPs with superior agonist activity. J Biol Chem. 285(16):12169-80

Stryker Biotech: OP-1 Implant® product information (2009).

Vukicevic S, Sampath T K, editors. Bone Morphogenetic Proteins: from Laboratory to Clinical Practice. Basel: Birkhauser Verlag, 2002.

Vukicevic, S., Basic, V., Rogic, D., Basic, N., Shih, M-S., Shepard, A., Jin, D., Dattatreyamurty, B., Jones, W., Dorai, H., Ryan, S., Griffiths, D., Maliakal, J., Jelic, M., Pastorcic, M., Stavljenic, A. and Sampath, T. K. (1998). Osteogenic Protein-1 reduces severity of injury in ischemic acute renal failure. *J. Clin. Invest.* 102: 202-214.

Vukicevic S, Sampath, T K, editors, Bone Morphogenetic Proteins: Systems Biology Regulators. Springer International Publishing; 2017.

Wang E A, Rosen V, D'Alessandro J S, Bauduy M, Cordes P, Harada T, et al. (1990) Recombinant human bone morphogenetic protein induces bone formation. Proc Natl Acad Sci USA. 87(6):2220-4.

Wozney J M, Rosen V, Celeste A J, Mitsock L M, Whitters M J, Kriz R W, et al. (1988) Novel regulators of bone formation: molecular clones and activities. Science. 242 (4885):1528-34.

Sampath T K, Rashka K E, Doctor J S, Tucker R F, Hoffmann F M (1993) *Drosophila* transforming growth factor superfamily proteins induce endochondral bone formation in mammals. Proc Natl Acad Sci USA 90:6004-6008.

What is claimed is:

1. An autologous bone graft substitute composition for inducing new bone formation, promoting bone growth and treating bone defect, wherein the composition comprises:
   (i) autologous blood;
   (ii) one or more analogs of BMP-6, BMP-2, BMP-7, BMP-4, BMP-5, BMP-8, BMP-9, BMP-12, and BMP-13, and combinations thereof, in a range of from 0.002 mg per ml to 1 mg per ml of autologous blood, wherein the one or more analogs are protein dimers having 7 cysteines and an inter disulfide bridge at the 4th cysteine and lack affinity for naturally occurring BMP antagonist, Noggin and N-terminal amino acid introduction; and
   (iii) a compression resistant matrix selected from the group consisting of a bone autograft, bone allograft, hydroxyapatite, tri-calcium phosphate, and combinations thereof;
   wherein the autologous blood forms a coagulum gel comprising a fibrin-meshwork reinforced with the compression resistant matrix, the coagulum gel containing the one or more analogs of BMP-6, BMP-2, BMP-7, BMP-4, BMP-5, BMP-8, BMP-9, BMP-12, and BMP-13, whereby the coagulum gel provides a sustained release of the one or more analogs of BMP-6, BMP-2, BMP-7, BMP-4, BMP-5, BMP-8, BMP-9, BMP-12, and BMP-13
   whereby the autologous bone graft substitute composition induces ectopic bone formation.

2. The composition according to claim 1, wherein the compression resistant matrix has a shape of any one selected from cylinder, slab, sheet, mesh, particulate or any other shape depending on a bone defect.

3. The composition according to claim 1, wherein a solubilized form of the one or more analogs of BMP-6, BMP-2, BMP-7, BMP-4, BMP-5, BMP-8, BMP-9, BMP-12, and BMP-13 is contained in a lyophilized form in the compression resistant matrix.

4. The composition according to claim 1, wherein the sustained release of the one or more analogs of BMP-6, BMP-2, BMP-7, BMP-4, BMP-5, BMP-8, BMP-9, BMP-12, and BMP-13 continues for 7 to 10 days after forming the coagulum gel.

5. The composition according to claim 1, wherein the sustained release of the one or more analogs of BMP-6, BMP-2, BMP-7, BMP-4, BMP-5, BMP-8, BMP-9, BMP-12, and BMP-13 is provided during a time period 10 days or more after forming the coagulum gel.

6. The composition according to claim 1, wherein the composition further comprises a blood clotting agent,
   wherein the blood clotting agent is selected from the group consisting of pharmacologically acceptable calcium, strontium or magnesium salts in ionic solution or nanoparticles and Ca++microsphere conjugates; and
   wherein the blood clotting agent is present in a range from above 15 to 50 mM per ml of autologous blood.

7. The composition according to claim 1, wherein the one or more analogs is an analog of BMP-6 provided in a range of 2 to 200 µg per ml of autologous blood.

8. The composition according to claim 7, wherein the analog of BMP-6 is provided in the amount of 100 µg per ml of autologous blood.

9. The composition according to claim 1, wherein the composition is injectable, extrudable or implantable.

10. A method of preparation of an autologous bone graft substitute composition, comprising the steps of:
    (1) mixing:
       a) autologous blood;
       b) one or more analogs of BMP-6, BMP-2, BMP-7, BMP-4, BMP-5, BMP-8, BMP-9, BMP-12, and BMP-13, and combinations thereof, in a range of from 0.002 mg per ml to 1 mg per ml of autologous blood, wherein the one or more analogs are protein dimers having 7 cysteines and an inter disulfide bridge at the 4th cysteine and lack affinity for naturally occurring BMP antagonist, Noggin and N-terminal amino acid introduction; and
       c) a compression resistant matrix selected from the group consisting of a bone allograft, bone autograft, hydroxyapatite (HA), tri-calcium phosphate (TCP), and combinations thereof;
    (2) incubating components of step (1) for a period sufficient to form a coagulum gel comprising a fibrin-meshwork reinforced with the compression resistant matrix, the coagulum gel containing the one or more analogs of BMP-6, BMP-2, BMP-7, BMP-4, BMP-5, BMP-8, BMP-9, BMP-12, and BMP-13, whereby the coagulum gel and the compression resistant matrix provide a sustained release of the one or more analogs of BMP-6, BMP-2, BMP-7, BMP-4, BMP-5, BMP-8, BMP-9, BMP-12, and BMP-13.

11. The method according to claim 10, further comprising:
    a. mixing the one or more analogs of BMP-6, BMP-2, BMP-7, BMP-4, BMP-5, BMP-8, BMP-9, BMP-12, and BMP-13 in an aqueous solution with the compression resistant matrix in a sterile lyophilization container wherein a volume of an aqueous solution containing the one or more analogs of BMP-6, BMP-2, BMP-7, BMP-4, BMP-5, BMP-8, BMP-9, BMP-12, and BMP-13 added to the compression resistant matrix is optimized for complete wetting of the compression resistant matrix;
    b. lyophilization of the one or more analogs of BMP-6, BMP-2, BMP-7, BMP-4, BMP-5, BMP-8, BMP-9, BMP-12, and BMP-13 in aqueous solution and the compression resistant matrix;
c. adding autologous blood; and
d. incubating the lyophilized form of the one or more analogs of BMP-6, BMP-2, BMP-7, BMP-4, BMP-5, BMP-8, BMP-9, BMP-12, and BMP-13 and the compression resistant matrix composite in autologous blood for a period sufficient to form a biomechanically stable blood clot around the lyophilized form of the one or more analogs of BMP-6, BMP-2, BMP-7, BMP-4, BMP-5, BMP-8, BMP-9, BMP-12, and BMP-13 and the compression resistant matrix.

12. The method according to claim 11, wherein the sustained release of the one or more analogs of BMP-6, BMP-2, BMP-7, BMP-4, BMP-5, BMP-8, BMP-9, BMP-12, and BMP-13 continues for 7 to 10 days after forming the coagulum gel.

13. The method according to claim 11, wherein the sustained release of the one or more analogs of BMP-6, BMP-2, BMP-7, BMP-4, BMP-5, BMP-8, BMP-9, BMP-12, and BMP-13 is provided during a time period 10 days or more after forming the coagulum gel.

14. The method according to claim 10, further comprising adding in step (1) a blood clotting agent.

15. The method according to claim 14, wherein:
the blood clotting agent is selected from the group consisting of:
pharmacologically acceptable calcium, strontium or magnesium salts in ionic solution or nanoparticles and Ca++microsphere conjugates; and
the blood clotting agent is added in a range from above 15 to 50 mM per ml of autologous blood.

16. The method according to claim 15, wherein the one or more analogs is BMP-6 provided in a range of 2 µg per ml to 200 µg per ml of autologous blood.

17. The method according to claim 16, wherein the analog of BMP-6 is provided in the amount of 100 µg per ml of autologous blood.

18. The method according to claim 10, wherein the period sufficient to form the coagulum gel is 60 minutes.

19. A method of inducing or promoting bone growth by treatment of a bone with an autologous bone graft substitute composition comprising:
(i) autologous blood;
(ii) one or more analogs of BMP-6, BMP-2, BMP-7, BMP-4, BMP-5, BMP-8, BMP-9, BMP-12, and BMP-13, and combinations thereof, in a range of from 0.002 mg per ml to 1 mg per ml of autologous blood, wherein the one or more analogs are protein dimers having 7 cysteines and an inter disulfide bridge at the 4th cysteine and lack affinity for naturally occurring BMP antagonist, Noggin and N-terminal amino acid introduction; and
(iii) a compression resistant matrix selected from the group consisting of a bone autograft, bone allograft, hydroxyapatite, tri-calcium phosphate, and combinations thereof;
wherein the autologous blood forms a coagulum gel comprising a fibrin-meshwork reinforced with the compression resistant matrix, the coagulum gel containing the one or more analogs of BMP-6, BMP-2, BMP-7, BMP-4, BMP-5, BMP-8, BMP-9, BMP-12, and BMP-13, whereby the coagulum gel provides a sustained release of the one or more analogs of BMP-6, BMP-2, BMP-7, BMP-4, BMP-5, BMP-8, BMP-9, BMP-12, and BMP-13, whereby the autologous bone graft substitute composition induces ectopic bone formation.

20. The method of claim 19, wherein the inducing or promoting bone growth is provided for the purposes of Posterolateral Lumbar Fusion; Anterior Lumbar Interbody Fusion, Adult Scoliosis, Trauma (Spine Reconstruction), Maxilla-cranial reconstruction or High Tibial Osteotomy.

21. An autologous bone graft substitute composition for inducing new bone formation, promoting bone growth and treating of bone defect, wherein the composition comprises:
(i) autologous blood;
(ii) one or more analogs of BMP-6, BMP-2, BMP-7, BMP-4, BMP-5, BMP-8, BMP-9, BMP-12, and BMP-13, and combinations thereof, in a range of from 0.002 mg per ml to 1 mg per ml of autologous blood, wherein the one or more analogs are protein dimers having 7 cysteines and an inter disulfide bridge at the 4th cysteine and lack affinity for naturally occurring BMP antagonist, Noggin and N-terminal amino acid introduction;
(iii) a compression resistant matrix selected from the group consisting of a bone autograft, bone allograft, hydroxyapatite, tri-calcium phosphate, and combinations thereof; and
(iv) a blood clotting agent in a range from above 15 mM to 50 mM per ml of autologous blood; the blood clotting agent being selected from the group consisting of: pharmacologically acceptable calcium, strontium or magnesium salts in ionic solution or nanoparticles and Ca++microsphere conjugates; wherein the autologous blood forms a coagulum gel comprising the one or more analogs of BMP-6, BMP-2, BMP-7, BMP-4, BMP-5, BMP-8, BMP-9, BMP-12, and BMP-13 and the autologous blood clotting agent, said coagulum gel having a structure and rheological properties that provide a sustained release of the one or more analogs of BMP-6, BMP-2, BMP-7, BMP-4, BMP-5, BMP-8, BMP-9, BMP-12, and BMP-13.

22. The composition according to claim 21, wherein the one or more analogs is an analog of BMP-6 provided in a range of 25 to 100 µg per 1.5 ml of autologous blood coagulum gel.

23. The composition according to claim 21, wherein the sustained release of the one or more analogs of BMP-6, BMP-2, BMP-7, BMP-4, BMP-5, BMP-8, BMP-9, BMP-12, and BMP-13 provided for 7 to 10 days after forming the coagulum gel.

24. A method of preparation of an autologous bone graft substitute composition, comprising the steps of:
(1) mixing:
a) autologous blood;
b) one or more analogs of BMP-6, BMP-2, BMP-7, BMP-4, BMP-5, BMP-8, BMP-9, BMP-12, BMP-13, and combinations thereof, in a range of from 0.002 mg per ml to 1 mg per ml of autologous blood, wherein the one or more analogs are protein dimers having 7 cysteines and an inter disulfide bridge at the 4th cysteine and lack affinity for naturally occurring BMP antagonist, Noggin and N-terminal amino acid introduction;
c) a compression resistant matrix selected from the group consisting of a bone autograft, bone allograft, hydroxyapatite, tri-calcium phosphate, and combinations thereof; and
d) a blood clotting agent in a range from above 15 mM to 50 mM per ml of autologous blood; the blood clotting agent being selected from the group consisting of: pharmacologically acceptable calcium, strontium or magnesium salts in ionic solution or nanoparticles and Ca++microsphere conjugates;
(2) incubating components of step (1) for a period sufficient to form a coagulum gel, said coagulum gel having a structure and rheological properties resulting in a sustained release of the one or more analogs of BMP-6, BMP-2, BMP-7, BMP-4, BMP-5, BMP-8, BMP-9, BMP-12, and BMP-13.

25. The method according to claim 24, wherein the one or more analogs is an analog of BMP-6 provided in a range of 25 to 100 μg per 1.5 ml of autologous blood coagulum gel.

26. The method according to claim 24, wherein the period sufficient to form the coagulum gel is 60-90 minutes.

27. A method of inducing or promoting bone growth by treatment of a bone with an autologous bone graft substitute composition comprising:
   (i) autologous blood;
   (ii) one or more analogs of BMP-6, BMP-2, BMP-7, BMP-4, BMP-5, BMP-8, BMP-9, BMP-12, BMP-13, and combinations thereof, in a range of from 0.002 mg per ml to 1 mg per ml of autologous blood, wherein the one or more analogs are protein dimers having 7 cysteines and an inter disulfide bridge at the 4th cysteine and lack affinity for naturally occurring BMP antagonist, Noggin and N-terminal amino acid introduction;
   (iii) a compression resistant matrix selected from the group consisting of a bone autograft, bone allograft, hydroxyapatite, tri-calcium phosphate, and combinations thereof; and
   (iv) a blood clotting agent in a range from above 15 mM to 50 mM per ml of autologous blood; the blood clotting agent being selected from the group consisting of: pharmacologically acceptable calcium, strontium or magnesium salts in ionic solution or nanoparticles and Ca++microsphere conjugates; wherein the autologous blood forms a coagulum gel comprising the one or more analogs of BMP-6, BMP-2, BMP-7, BMP-4, BMP-5, BMP-8, BMP-9, BMP-12, and BMP-13 and the autologous blood clotting agent, said coagulum gel having a structure and rheological properties that provide a sustained release of the one or more analogs of BMP-6, BMP-2, BMP-7, BMP-4, BMP-5, BMP-8, BMP-9, BMP-12, and BMP-13, whereby the autologous bone graft substitute composition induces ectopic bone formation.

28. The method of claim 27, wherein the inducing or promoting bone growth is provided for the purposes of Pseudo-arthrosis associated with Long Bone and Spine, Tibial Non-Union Fracture, Hypophosphatasia, Osteogenesis Imperfecta, Neurofibromatosis Type I, Atypical Osteoporotic Fractures, Dental Indications, Periodontal Repair, Dental/Bone Implants, Alveolar-ridge Augmentation, Osteoporotic Fractures, Atypical femoral fracture, Vertebral bone fracture or Distal radial fracture.

* * * * *